US008895301B2

(12) United States Patent
Zhang et al.

(10) Patent No.: US 8,895,301 B2
(45) Date of Patent: Nov. 25, 2014

(54) EXOGENOUS PAX6 NUCLEIC ACID EXPRESSION IN PRIMATE NEURAL STEM CELLS MAINTAINS PROLIFERATION WITHOUT DIFFERENTIATION

(75) Inventors: Su-Chun Zhang, Middleton, WI (US); Xiaoqing Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/360,326

(22) Filed: Jan. 27, 2012

(65) Prior Publication Data

US 2012/0157510 A1 Jun. 21, 2012

Related U.S. Application Data

(63) Continuation of application No. 12/849,249, filed on Aug. 3, 2010, now Pat. No. 8,133,731.

(60) Provisional application No. 61/273,373, filed on Aug. 3, 2009, provisional application No. 61/273,690, filed on Aug. 6, 2009.

(51) Int. Cl.
| | | |
|---|---|---|
| *C12N 5/071* | (2010.01) | |
| *C12N 15/02* | (2006.01) | |
| *C12N 5/0797* | (2010.01) | |
| *C12N 15/86* | (2006.01) | |
| *C12N 5/074* | (2010.01) | |
| *C12N 5/079* | (2010.01) | |

(52) U.S. Cl.
CPC .............. *C12N 5/0623* (2013.01); *C12N 15/86* (2013.01); *C12N 2501/60* (2013.01); *C12N 5/0696* (2013.01); *C12N 2502/99* (2013.01); *C12N 5/0618* (2013.01); *C12N 2501/40* (2013.01); *C12N 2506/02* (2013.01); *C12N 2506/08* (2013.01); *C12N 2510/00* (2013.01)
USPC ............ 435/368; 435/375; 435/384; 435/455

(58) Field of Classification Search
CPC .... C12N 5/073; C12N 5/0735; C12N 5/0789; C12N 5/10; C12N 5/12; C12N 15/09; C12N 15/63; C12N 5/0623; C12N 2501/60; C12N 5/0696; C12N 2502/99; C12N 15/86; C12N 2506/08; C12N 5/0618
See application file for complete search history.

(56) References Cited

U.S. PATENT DOCUMENTS

| | | | |
|---|---|---|---|
| 7,588,937 B2 | 9/2009 | Zhang et al. | |
| 7,972,850 B2 | 7/2011 | Zhang et al. | |
| 8,133,731 B2 | 3/2012 | Zhang et al. | |
| 8,153,424 B2 | 4/2012 | Zhang et al. | |

FOREIGN PATENT DOCUMENTS

KR 1020070084750 A 8/2007

OTHER PUBLICATIONS

Dimos et al. Induced Pluripotent Stem Cells Generated from Patients with ALS Can Be Differentiated into Motor NeuronsScience, published online Jul. 31, 2008, vol. 321, pp. 1218-1221.*
Cartier, et al., Pax6-Induced Alteration of Cell Fate: Shape Changes, Expression of Neuronal a Tubulin, Postmitotic Phenotype, and Cell Migration, Journal of Neurobiology, 2006, 66(5):421-436.
Duparc, et al., Pax6 Controls the Proliferation Rate of Neuroepithelial Progenitors from the Mouse Optic Vesicle, Developmental Biology, 2007, 301:374-387.
Gerrard, et al., Differentiation of Human Embryonic Stem Cells to Neural Lineages in Adherent Culture by Blocking Bone Morphogenetic Protein Signaling, Stem Cells, 2005, 23:1234-1241.
Hack, et al., Regionalization and Fate Specification in Neurospheres: The Role of Olig2 and Pax6, Mol. Cell. Neurosci., 2004, 25:664-678.
Heins, et al., Glial Cells Generate Neurons: The Role of the Transcription Factor Pax6, Nature Neuroscience, 2002, 5(4):308-315.
Kallur, et al., Human Fetal Cortical and Striatal Neural Stem Cells Generate Region-Specific Neurons in Vitro and Differentiate Extensively to Neurons After Intrastriatal Transplantation in Neonatal Rats, Journal of Neuroscience Research, 2006, 84:1630-1644.
Kallur, et al., Pax6 Promotes Neurogenesis in Human Neural Stem Cells, Molecular and Cellular Neuroscience, 2008, 38:616-628.
Li, et al., Specification of Motoneurons from Human Embryonic Stem Cells, Nature Biotechnology, 2005, 23(2):215-221.
Ma, et al., High-Level Sustained Transgene Expression in Human Embryonic Stem Cells Using Lentiviral Vectors, Stem Cells, 2003, 21:111-117.
Pankratz, et al., Directed Neural Differentiation of Human Embryonic Stem Cells Via an Obligated Primitive Anterior Stage, Stem Cells, 2007, 25:1511-1520.
Pells, et al., Multipotentiality of Neuronal Cells After Spontaneous Fusion with Embryonic Stem Cells and Nuclear Reprogramming In Vitro, Cloning and Stem Cells, 2002, 4(4):331-340.
Perrier, et al., Derivation of Midbrain Dopamine Neurons From Human Embryonic Stem Cells, PNAS, 2004, 101 (34):12543-12548.
Spitere, et al., TAT-PAX6 Protein Transduction in Neural Progenitor Cells: A Novel Approach for Generation of Dopaminergic Neurones In Vitro, Brain Research, 2008, 1208:25-34.
Suter, et al., A Sox1 to Pax6 Switch Drives Neuroectoderm to Radial Glia Progression During Differentiation of Mouse Embryonic Stem Cells, Stem Cells, 2009, 27:49-58.
Ueno, et al., Experimental Transplantation of Corneal Epithelium-Like Cells Induced by Pax6 Gene Transfection of Mouse Embryonic Stem Cells, Cornea, 2007, 26(10):1220-1227.
Von Holst, et al., Neural Stem/Progenitor Cells Express 20 Tenascin C Isoforms That Are Differentially Regulated by Pax6, Journal of Biological Chemistry, 2007, 282(12):9172-9181.
Wu, et al., Dynamic Transcriptomes During Neural Differentiation of Human Embryonic Stem Cells Revealed by Short, Long, and Paired-End Sequencing, PNAS, 2010, 107(11):5254-5259.

(Continued)

*Primary Examiner* — Deborah Crouch
(74) *Attorney, Agent, or Firm* — Quarles & Brady LLP

(57) ABSTRACT

A transcription factor both necessary and sufficient for human neuroectoderm specification, Pax6, as well as applications thereof, is disclosed.

11 Claims, 34 Drawing Sheets

(56) References Cited

OTHER PUBLICATIONS

Yan, et al., Protein Phosphatase-1 Modulates the Function of Pax-6, A Transcription Factor Controlling Brain and Eye Development, Journal of Biological Chemistry, 2007, 282(19):13954-13965.

Zhang, et al., In Vitro Differentiation of Transplantable Neural Precursors from Human Embryonic Stem Cells, Nature Biotechnology, 2001, 19:1129-1133.

Zhang, et al., Pax6 is a Human Neuroectoderm Cell Fate Determinant, Cell Stem Cell, 2010, 7:90-100.

Zhou, et al., Inducible and Reversible Transgene Expression in Human Stem Cells After Efficient and Stable Gene Transfer, Stem Cells, 2007, 25:779-789.

PCT International Search Report and Written Opinion, PCT/US2010/044268, Apr. 15, 2011.

* cited by examiner

Protein sequence of Pax6a (SEQ ID NO:112)

MQNSHSGVNQLGGVFVNGRPLPDSTRQKIVELAHSGARPCDISRILQVSNGCVSKILGRYY
ETGSIRPRAIGGSKPRVATPEVVSKIAQYKRECPSIFAWEIRDRLLSEGVCTNDNIPSVSSIN
RVLRNLASEKQQMGADGMYDKLRMLNGQTGSWGTRPGWYPGTSVPGQPTQDGCQQQE
GGGENTNSISSNGEDSDEAQMRLQLKRKLQRNRTSFTQEQIEALEKEFERTHYPDVFARE
RLAAKIDLPEARIQVWFSNRRAKWRREEKLRNQRRQASNTPSHIPISSSFSTSVYQPIPQPT
TPVSSFTSGSMLGRTDTALTNTYSALPPMPSFTMANNLPMQPPVPSQTSSYSCMLPTSPS
VNGRSYDTYTPPHMQTHMNSQPMGTSGTTSTGLISPGVSVPVQVPGSEPDMSQYWPRL
Q

Fig. 9 mRNA sequence of Pax6 transcription variant 1 (SEQ ID NO:113, coding Pax6a)

```
   1 ggtgcatttg catgttgcgg agtgattagt gggtttgaaa agggaaccgt ggctcggcct
  61 catttcccgc tctggttcag gcgcaggagg aagtgttttg ctggaggatg atgacagagg
 121 tcaggcttcg ctaatgggcc agtgaggagc ggtggaggcg aggccgggcg ccggcacaca
 181 cacattaaca cacttgagcc atcaccaatc agcataggaa tctgagaatt gctctcacac
 241 accaacccag caacatccgt ggagaaaact ctcaccagca actcctttaa acaccgtca
 301 tttcaaacca ttgtggtctt caagcaacaa cagcagcaca aaaaacccca accaaacaaa
 361 actcttgaca gaagctgtga caaccagaaa ggatgcctca taaggggga agactttaac
 421 taggggcgcg cagatgtgtg aggcctttta ttgtgagagt ggacagacat ccgagatttc
 481 agagccccat attcgagccc cgtggaatcc cgcggccccc agccagagcc agcatgcaga
 541 acagtcacag cggagtgaat cagctcggtg gtgtctttgt aacgggcgg ccactgccgg
 601 actccacccg gcagaagatt gtagagctag ctcacagcgg ggcccggccg tgcgacattt
 661 cccgaattct gcaggtgtcc aacggatgtg tgagtaaaat tctgggcagg tattacgaga
 721 ctggctccat cagacccagg gcaatcggtg gtagtaaacc gagagtagcg actccagaag
 781 ttgtaagcaa aatagcccag tataagcggg agtgcccgtc catctttgct tgggaaatcc
 841 gagacagatt actgtccgag ggggtctgta ccaacgataa cataccaagc gtgtcatcaa
 901 taaacagagt tcttcgcaac ctggctagcg aaaagcaaca gatgggcgca gacggcatgt
 961 atgataaact aaggatgttg aacgggcaga ccggaagctg ggcacccgc cctggttggt
1021 atccggggac ttcggtgcca gggcaaccta cgcaagatgg ctgccagcaa caggaaggag
1081 ggggagagaa taccaactcc atcagttcca acggagaaga ttcagatgag gctcaaatgc
1141 gacttcagct gaagcggaag ctgcaaagaa atagaacatc ctttacccaa gagcaaattg
1201 aggccctgga gaaagagttt gagagaaccc attatccaga tgtgtttgcc cgagaaagac
1261 tagcagccaa aatagatcta cctgaagcaa gaatacaggt atggttttct aatcgaaggg
1321 ccaaatggag aagagaagaa aaactgagga atcagagaag acaggccagc aacacaccta
1381 gtcatattcc tatcagcagt agtttcagca ccagtgtcta ccaaccaatt ccacaaccca
1441 ccacaccggt ttcctccttc acatctggct ccatgttggg ccgaacagac acagccctca
1501 caaacaccta gcgctctg ccgcctatgc ccagcttcac catggcaaat aacctgccta
1561 tgcaacccc agtccccagc cagacctcct catactcctg catgctgccc accagccctt
```

Fig. 10

```
1621  cggtgaatgg gcggagttat gatacctaca ccccccaca tatgcagaca cacatgaaca
1681  gtcagccaat gggcacctcg ggcaccactt caacaggact catttcccct ggtgtgtcag
1741  ttccagttca agttcccgga agtgaacctg atatgtctca atactggcca agattacagt
1801  aaaaaaaaaa aaaaaaaaa aaaggaaagg aaatattgtg ttaattcagt cagtgactat
1861  ggggacacaa cagttgagct ttcaggaaag aaagaaaaat ggctgttaga gccgcttcag
1921  ttctacaatt gtgtcctgta ttgtaccact ggggaaggaa tggacttgaa acaaggacct
1981  ttgtatacag aaggcacgat atcagttgga acaaatcttc attttggtat ccaaactttt
2041  attcattttg gtgtattatt tgtaaatggg catttgtatg ttataatgaa aaaagaaca
2101  atgtagactg gatggatgtt tgatctgtgt tggtcatgaa gttgttttt tttttttaa
2161  aaagaaaacc atgatcaaca agctttgcca cgaatttaag agttttatca agatatatcg
2221  aatacttcta cccatctgtt catagtttat ggactgatgt tccaagtttg tatcattcct
2281  ttgcatataa ttaaacctgg aacaacatgc actagattta tgtcagaaat atctgttggt
2341  tttccaaagg ttgttaacag atgaagttta tgtgcaaaaa agggtaagat ataaattcaa
2401  ggaagaaaaa aagttgatag ctaaaaggta gagtgtgtct tcgatataat ccaatttgtt
2461  ttatgtcaaa atgtaagtat ttgtcttccc tagaaatcct cagaatgatt tctataataa
2521  agttaatttc atttatattt gacaagaata tagatgtttt atacacattt tcatgcaatc
2581  atacgtttct tttttggcca gcaaaagtta attgttctta gatatagttg tattactgtt
2641  cacggtccaa tcatttgtg catctagagt tcattcctaa tcaattaaaa gtgcttgcaa
2701  gagttttaaa cttaagtgtt ttgaagttgt tcacaactac atatcaaaat taaccattgt
2761  tgattgtaaa aaaccatgcc aaagcctttg tatttccttt attatacagt tttctttta
2821  accttatagt gtggtgttac aaatttatt tccatgttag atcaacattc taaaccaatg
2881  gttactttca cacacactct gttttacatc ctgatgatcc ttaaaaaata atccttatag
2941  ataccataaa tcaaaaacgt gttagaaaaa aattccactt acagcagggt gtagatctgt
3001  gcccatttat acccacaaca tatatacaaa atggtaacat ttcccagtta gccatttaat
3061  tctaaagctc aaagtctaga aataattta aaatgcaaca agcgattagc taggaattgt
3121  tttttgaatt aggactggca ttttcaatct gggcagattt ccattgtcag cctatttcaa
3181  caatgatttc actgaagtat attcaaaagt agatttctta aaggagactt tctgaaagct
3241  gttgcctttt tcaaataggc cctctccctt ttctgtctcc ctcccctttg cacaagaggc
```

Fig. 10 (continued)

```
3301 atcatttccc attgaaccac tacagctgtt cccatttgaa tcttgctttc tgtgcggttg 3361 tggatggttg gagggtggag gggggatgtt gcatgtcaag gaataatgag cacagacaca 3421 tcaacagaca acaacaaagc agactgtgac tggccggtgg gaattaaagg ccttcagtca 3481 ttggcagctt aagccaaaca ttcccaaatc tatgaagcag ggcccattgt tggtcagttg 3541 ttatttgcaa tgaagcacag ttctgatcat gtttaaagtg gaggcacgca gggcaggagt 3601 gcttgagccc aagcaaagga tggaaaaaaa taagcctttg ttgggtaaaa aaggactgtc 3661 tgagactttc atttgttctg tgcaacatat aagtcaatac agataagtct tcctctgcaa 3721 acttcactaa aaagcctggg ggttctggca gtctagatta aaatgcttgc acatgcagaa 3781 acctctgggg acaaagacac acttccactg aattatactc tgctttaaaa aaatccccaa 3841 aagcaaatga tcagaaatgt agaaattaat ggaaggattt aaacatgacc ttctcgttca 3901 atatctactg ttttttagtt aaggaattac ttgtgaacag ataattgaga ttcattgctc 3961 cggcatgaaa tatactaata attttattcc accagagttg ctgcacattt ggagacacct 4021 tcctaagttg cagttttgt atgtgtgcat gtagttttgt tcagtgtcag cctgcactgc 4081 acagcagcac atttctgcag gggagtgagc acacatacgc actgttggta caattgccgg 4141 tgcagacatt tctacctcct gacattttgc agcctacatt ccctgagggc tgtgtgctga 4201 gggaactgtc agagaagggc tatgtgggag tgcatgccac agctgctggc tggcttactt 4261 cttccttctc gctggctgta atttccacca cggtcaggca gccagttccg gcccacggtt 4321 ctgttgtgta gacagcagag actttggaga cccggatgtc gcacgccagg tgcaagaggt 4381 gggaatggga gaaaaggagt gacgtgggag cggagggtct gtatgtgtgc acttgggcac 4441 gtatatgtgt gctctgaagg tcaggattgc cagggcaaag tagcacagtc tggtatagtc 4501 tgaagaagcg gctgctcagc tgcagaagcc ctctggtccg gcaggatggg aacggctgcc 4561 ttgccttctg cccacaccct agggacatga gctgtccttc caaacagagc tccaggcact 4621 ctcttgggga cagcatggca ggctctgtgt ggtagcagtg cctggagtt ggcctttac 4681 tcattgttga ataattttt gtttattatt tatttaacga tacatatatt tatatattta 4741 tcaatggggt atctgcaggg atgttttgac accatcttcc aggatggaga ttatttgtga 4801 agacttcagt agaatcccag gactaaacgt ctaaattttt tctccaaact tgactgactt 4861 gggaaaacca ggtgaataga ataagagctg aatgttttaa gtaataaacg ttcaaactgc 4921 tctaagtaaa aaaatgcatt ttactgcaat gaatttctag aatattttc ccccaaagct
```

Fig. 10 (continued)

```
4981 atgcctccta acccttaaat ggtgaacaac tggtttcttg ctacagctca ctgccatttc
5041 ttcttactat catcactagg tttcctaaga ttcactcata cagtattatt tgaagattca
5101 gctttgttct gtgaatgtca tcttaggatt gtgtctatat tcttttgctt atttcttttt
5161 actctgggcc tctcatacta gtaagatttt aaaaagcctt ttcttctctg tatgtttggc
5221 tcaccaaggc gaaatatata ttcttctctt tttcatttct caagaataaa cctcatctgc
5281 ttttttgttt ttctgtgttt tggcttggta ctgaatgact caactgctcg gttttaaagt
5341 tcaaagtgta agtacttagg gttagtactg cttatttcaa taatgttgac ggtgactatc
5401 tttggaaagc agtaacatgc tgtcttagaa atgacattaa taatgggctt aaacaaatga
5461 ataggggggt cccccccactc tcctttttgta tgcctatgtg tgtctgattt gttaaaagat
5521 ggacagggaa ttgattgcag agtgtcgctt ccttctaaag tagttttatt ttgtctactg
5581 ttagtatttta aagatcctgg aggtggacat aaggaataaa tggaagagaa aagtagatat
5641 tgtatggtgg ctactaaaag gaaattcaaa aagtcttaga acccgagcac ctgagcaaac
5701 tgcagtagtc aaaatattta tctcatgtta aagaaaggca aatctagtgt aagaaatgag
5761 taccatatag ggttttgaag ttcatatact agaaacactt aaaagatatc atttcagata
5821 ttacgtttgg cattgttctt aagtatttat atctttgagt caagctgata attaaaaaaa
5881 atctgttaat ggagtgtata tttcataatg tatcaaaatg gtgtctatac ctaaggtagc
5941 attattgaag agagatatgt ttatgtagta agttattaac ataatgagta acaaataatg
6001 tttccagaag aaaggaaaac acattttcag agtgcgtttt tatcagagga agacaaaaat
6061 acacacccct ctccagtagc ttattttttac aaagccggcc cagtgaatta gaaaaacaaa
6121 gcacttggat atgattttttg gaaagcccag gtacacttat tattcaaaat gcacttttac
6181 tgagtttgaa aagtttcttt tatatttaaa ataagggttc aaatatgcat attcaatttt
6241 tatagtagtt atctatttgc aaagcatata ttaactagta attggctgtt aattttatag
6301 acatggtagc cagggaagta tatcaatgac ctattaagta ttttgacaag caatttacat
6361 atctgatgac ctcgtatctc ttttttcagca agtcaaatgc tatgtaattg ttccattgtg
6421 tgttgtataa aatgaatcaa cacggtaaga aaaggttag agttattaaa ataataaact
6481 gactaaaata ctcatttgaa tttattcaga atgttcataa tgctttcaaa ggacatagca
6541 gagcttttgt ggagtatccg cacaacatta tttattatct atggactaaa tcaattttttt
6601 gaagttgctt taaaatttaa aagcaccttt gcttaatata aagccctttta attttaactg
```

Fig. 10 (continued)

```
6661 acagatcaat tctgaaactt tattttgaaa agaaaatggg gaagaatctg tgtctttaga
6721 attaaaagaa atgaaaaaaa taaacccgac attctaaaaa aatagaataa gaaacctgat
6781 ttttagtact aatgaaatag cgggtgacaa aatagttgtc tttttgattt tgatcacaaa
6841 aaataaactg gtagtgacag gatatgatgg agagatttga catcctggca aatcactgtc
6901 attgattcaa ttattctaat tctgaataaa agctgtatac agtaaaa
```

Fig. 10 (continued)

Protein sequence of Pax6b (SEQ ID NO:114)

MQNSHSGVNQLGGVFVNGRPLPDSTRQKIVELAHSGARPCDISRILQTHADAKVQVLDNQ
NVSNGCVSKILGRYYETGSIRPRAIGGSKPRVATPEVVSKIAQYKRECPSIFAWEIRDRLLSE
GVCTNDNIPSVSSINRVLRNLASEKQQMGADGMYDKLRMLNGQTGSWGTRPGWYPGTSV
PGQPTQDGCQQQEGGGENTNSISSNGEDSDEAQMRLQLKRKLQRNRTSFTQEQIEALEK
EFERTHYPDVFARERLAAKIDLPEARIQVWFSNRRAKWRREEKLRNQRRQASNTPSHIPIS
SSFSTSVYQPIPQPTTPVSSFTSGSMLGRTDTALTNTYSALPPMPSFTMANNLPMQPPVPS
QTSSYSCMLPTSPSVNGRSYDTYTPPHMQTHMNSQPMGTSGTTSTGLISPGVSVPVQVP
GSEPDMSQYWPRLQ

Fig. 11 mRNA sequence of Pax6 transcription variant 2 (SEQ ID NO:115, coding Pax6b)

```
   1 ggtgcatttg catgttgcgg agtgattagt gggtttgaaa agggaaccgt ggctcggcct
  61 catttcccgc tctggttcag gcgcaggagg aagtgttttg ctggaggatg atgacagagg
 121 aatctgagaa ttgctctcac acaccaaccc agcaacatcc gtggagaaaa ctctcaccag
 181 caactccttt aaaacaccgt catttcaaac cattgtggtc ttcaagcaac aacagcagca
 241 caaaaaaccc caaccaaaca aaactcttga cagaagctgt gacaaccaga aaggatgcct
 301 cataaagggg gaagacttta actagggcg cgcagatgtg tgaggccttt tattgtgaga
 361 gtggacagac atccgagatt tcagagcccc atattcgagc ccgtggaat cccgcggcc
 421 ccagccagag ccagcatgca gaacagtcac agcggagtga atcagctcgg tggtgtcttt
 481 gtcaacgggc ggccactgcc ggactccacc ggcagaaga ttgtagagct agctcacagc
 541 ggggccggc cgtgcgacat tcccgaatt ctgcagaccc atgcagatgc aaaagtccaa
 601 gtgctggaca atcaaaacgt gtccaacgga tgtgtgagta aaattctggg caggtattac
 661 gagactggct ccatcagacc cagggcaatc ggtggtagta accgagagt agcgactcca
 721 gaagttgtaa gcaaaatagc ccagtataag cgggagtgcc cgtccatctt tgcttgggaa
 781 atccgagaca gattactgtc cgaggggtc tgtaccaacg ataacatacc aagcgtgtca
 841 tcaataaaca gagttcttcg caacctggct agcgaaaagc aacagatggg cgcagacggc
 901 atgtatgata aactaaggat gttgaacggg cagaccggaa gctgggcac cgcctggt
 961 tggtatccgg ggacttcggt gccagggcaa cctacgcaag atggctgcca gcaacaggaa
1021 ggagggggag agaataccaa ctccatcagt tccaacggag aagattcaga tgaggctcaa
1081 atgcgacttc agctgaagcg gaagctgcaa agaaatagaa catcctttac ccaagagcaa
1141 attgaggccc tggagaaaga gttgagaga accattatc agatgtgtt gcccgagaa
1201 agactagcag ccaaaataga tctacctgaa gcaagaatac aggtatggtt ttctaatcga
1261 agggccaaat ggagaagaga agaaaactg aggaatcaga gaagacaggc cagcaacaca
1321 cctagtcata tccctatcag cagtagtttc agcaccagtg tctaccaacc aattccacaa
1381 cccaccacac cggttttcctc cttcacatct ggctccatgt gggcgaac agacacagcc
1441 ctcacaaaca cctacagcgc tctgcgcct atgccaget tcaccatggc aaataacctg
1501 cctatgcaac cccagtcc cagccagacc tcctcatact cctgcatgct gcccaccagc
1561 ccttcggtga atgggcggag ttatgatacc tacacccca cacatatgca gacacacatg
```

Fig. 12

```
1621 aacagtcagc caatgggcac ctcgggcacc acttcaacag gactcatttc cctggtgtg
1681 tcagttccag ttcaagttcc cggaagtgaa cctgatatgt ctcaatactg gccaagatta
1741 cagtaaaaaa aaaaaaaaaa aaaaaagga aaggaaatat tgtgttaatt cagtcagtga
1801 ctatggggac acaacagttg agctttcagg aaagaaagaa aaatggctgt tagagccgct
1861 tcagttctac aattgtgtcc tgtattgtac cactggggaa ggaatggact gaaacaagg
1921 acctttgtat acagaaggca cgatatcagt tggaacaaat cttcattttg gtatccaaac
1981 ttttattcat tttggtgtat tatttgtaaa tgggcatttg tatgttataa tgaaaaaag
2041 aacaatgtag actggatgga tgtttgatct gtgttggtca tgaagttgtt ttttttttt
2101 ttaaaaagaa aaccatgatc aacaagcttt gccacgaatt taagagtttt atcaagatat
2161 atcgaatact tctacccatc tgttcatagt ttatggactg atgttccaag tttgtatcat
2221 tcctttgcat ataattaaac ctggaacaac atgcactaga tttatgtcag aaatatctgt
2281 tggttttcca aaggttgtta acagatgaag tttatgtgca aaaagggta agatataaat
2341 tcaaggaaga aaaaagttg atagctaaaa ggtagagtgt gtcttcgata taatccaatt
2401 tgtttatgt caaatgtaa gtatttgtct tcctagaaa tcctcagaat gatttctata
2461 ataagttaa tttcatttat atttgacaag aatatagatg ttttatacac attttcatgc
2521 aatcatacgt ttctttttg gccagcaaaa gttaattgtt cttagatata gttgtattac
2581 tgttcacggt ccaatcattt tgtgcatcta gagttcattc ctaatcaatt aaaagtgctt
2641 gcaagagttt taaacttaag tgttttgaag ttgttcacaa ctacatatca aaattaacca
2701 ttgttgattg taaaaaacca tgccaaagcc tttgtatttc ctttattata cagttttctt
2761 ttaaccttaa tagtgtggtg ttacaaattt tatttccatg ttagatcaac attctaaacc
2831 aatggttact ttcacacaca ctctgtttta catcctgatg atccttaaaa aataatcctt
2881 atagatacca taaatcaaaa acgtgttaga aaaaaattcc acttacagca gggtgtagat
2941 ctgtgcccat ttatacccac aacatatata caaatggta acatttccca gttagccatt
3001 taattctaaa gctcaaagtc tagaaataat ttaaaaatgc aacaagcgat tagctaggaa
3061 ttgttttttg aattaggact ggcatttca atctgggcag atttccattg tcagcctatt
3121 tcaacaatga tttcactgaa gtatattcaa aagtagattt cttaaaggag acttctgaa
3181 agctgttgcc ttttcaaat aggccctctc cctttctgt ctccctaccc tttgcacaag
3241 aggcatcatt tcccattgaa ccactacagc tgttccaatt tgaatcttgc tttctgtgcg
```

Fig. 12 (continued)

```
3301 gttgtggatg gttggagggt ggaggggggga tgttgcatgt caaggaataa tgagcacaga
3361 cacatcaaca gacaacaaca aagcagactg tgactggccg gtgggaatta aaggcettca
3421 gtcattggca gcttaagcca aacattccca aatctatgaa gcaggccca ttgttggtca
3481 gttgttattt gaatgaagc acagttctga tcatgtttaa agtggaggca cgcagggcag
3541 gagtgcttga gcccaagcaa aggatggaaa aaataagcc tttgttgggt aaaaaggac
3601 tgtctgagac tttcatttgt tctgtgcaac ataaagtca atacagataa gtcttcctct
3661 gcaaacttca ctaaaaagcc tggggttct ggcagtctag attaaaatgc ttgcacatgc
3721 agaaacctct ggggacaaag acacacttcc actgaattat actctgcttt aaaaaaatcc
3781 ccaaaagcaa atgatcagaa atgtagaaat taatggaagg attaaacat gaccttctcg
3841 ttcaatatct actgtttttt agttaaggaa ttacttgtga acagataatt gagattcatt
3901 gctccggcat gaaatatact aataatttta ttccaccaga gttgctgcac atttggagac
3961 accttcctaa gttgcagttt ttgtatgtgt gcatgtagtt tgttcagtg tcagctgca
4021 ctgcacagca gcacatttct gcagggagt gagcacacat acgcactgtt ggtacaattg
4081 ccggtgcaga cattctacc tcctgacatt ttgcagccta cattcctga gggctgtgtg
4141 ctgagggaac tgtcagagaa gggctatgtg ggagtgcatg ccacagctgc tggctggctt
4201 acttcttcct tctcgctggc tgtaattcc accaggtca ggcagccagt tccggcccac
4261 ggttctgttg tgtagacagc agagactttg gagaccgga tgtcgcacgc caggtgcaag
4321 aggtgggaat gggagaaaag gagtgacgtg ggagcggagg gtctgtatgt gtgcacttgg
4381 gcacgtatat gtgtgctctg aaggtcagga ttgccagggc aaagtagcac agtctggtat
4441 agtctgaaga agcggctgct cagctgcaga agccctctgg tccggcagga tgggaacggc
4501 tgccttgcct tctgccaca cctagggac atgagctgtc cttccaaaca gagctccagg
4561 cactctcttg gggacagcat ggcaggctct gtgtggtagc agtgcctggg agttggcctt
4621 ttactcattg ttgaaataat tttgtttat tatttattta acgatacata tatttatata
4681 tttatcaatg gggtatctgc agggatgttt tgacaccatc ttccaggatg gagattattt
4741 gtgaagactt cagtagaatc ccaggactaa acgtctaaat tttttctcca aacttgactg
4801 acttgggaaa accaggtgaa tagaataaga gctgaatgtt ttaagtaata aacgttcaaa
4861 ctgctctaag taaaaaaatg catttactg caatgaattt ctagaatatt tttccccaa
4921 agctatgcct cctaaccctt aaatggtgaa caactggttt cttgctacag ctcactgcca
```

Fig. 12 (continued)

```
4981 ttctttctta ctatcatcac taggtttcct aagattcact catacagtat tatttgaaga
5041 ttcagctttg ttctgtgaat gtcatcttag gattgtgtct atattctttt gcttatttct
5101 ttttactctg ggcctctcat actagtaaga ttttaaaaag cttttcttc tctgtatgtt
5161 tggctcacca aggcgaaata tatattcttc tcttttcat ttctcaagaa taaacctcat
5221 ctgcttttt gttttctgt gttttggctt ggtactgaat gactcaactg ctcggtttta
5281 aagttcaaag tgtaagtact tagggttagt actgcttatt tcaataatgt tgacggtgac
5341 tatctttgga aagcagtaac atgctgtctt agaaatgaca ttaataatgg gcttaaacaa
5401 atgaataggg gggtccccc actctccttt tgtatgccta tgtgtgtctg attgtttaaa
5461 agatggacag ggaattgatt gcagagtgtc gcttccttct aaagtagttt tatttgtct
5521 actgttagta tttaaagatc ctggaggtgg acataaggaa taaatggaag agaaaagtag
5581 atattgtatg gtggctacta aaaggaaatt caaaaagtct tagaacccga gcacctgagc
5641 aaactgcagt agtcaaaata tttatctcat gttaagaaa ggcaaatcta gtgtaagaaa
5701 tgagtaccat atagggtttt gaagttcata tactagaaac acttaaaaga tatcatttca
5761 gatattacgt ttggcattgt tcttaagtat ttatatcttt gagtcaagct gataattaaa
5821 aaaaatctgt taatggagtg tatatttcat aatgtatcaa aatggtgtct atacctaagg
5881 tagcattatt gaagagagat atgtttatgt agtaagttat taacataatg agtaacaaat
5941 aatgtttcca gaagaaagga aaacacattt tcagagtgcg ttttatcag aggaagacaa
6001 aaatacacac ccctctccag tagcttattt ttacaaagcc ggcccagtga attagaaaaa
6061 caaagcactt ggatatgatt tttggaaagc ccaggtacac ttattattca aaatgcactt
6121 ttactgagtt tgaaagttt cttttatatt taaataagg gttcaaatat gcatattcaa
6181 ttttatagt agttatctat ttgcaaagca tatattaact agtaattggc tgttaatttt
6241 atagacatgg tagccaggga agtatatcaa tgacctatta agtatttga caagcaattt
6301 acatatctga tgacctcgta tctctttttc agcaagtcaa atgctatgta attgttccat
6361 tgtgtgttgt ataaaatgaa tcaacacggt aagaaaagg ttagagttat taaaataata
6421 aactgactaa aatactcatt tgaatttatt cagaatgttc ataatgcttt caaggacat
6481 agcagagctt tgtggagta tcgcacaac attatttatt atctatggac taaatcaatt
6541 ttttgaagtt gctttaaaat ttaaagcac ctttgcttaa tataaagccc tttaatttta
6601 actgacagat caattctgaa acttatttt gaaagaaaa tgggaagaa tctgtgtctt
```

Fig. 12 (continued)

```
6661  tagaattaaa agaaatgaaa aaaataaacc cgacattcta aaaaaataga ataagaaacc
6721  tgattttag  tactaatgaa atagcgggtg acaaaatagt tgtcttttg  attttgatca
6781  caaaaataa  actggtagtg acaggatatg atggagagat ttgacatcct ggcaaatcac
6841  tgtcattgat tcaattattc taattctgaa taaaagctgt atacagtaaa a
```

Fig. 12 (continued)

mRNA sequence of Pax6 transcription variant 3 (SEQ ID NO:116, coding Pax6a)

```
   1 acgctctttt cttatcattg acatttaaac tctggggcag gtcctcgcgt agaacgcggc
  61 tgtcagatct gccacttccc ctgccgagcg gcggtgagaa gtgtgggaac cggcgctgc
 121 aggctcacct gcctcccgc cctccgctcc caggaatctg agaattgctc tcacacacca
 181 acccagcaac atccgtggag aaaactctca ccagcaactc ctttaaaaca ccgtcattc
 241 aaaccattgt ggtcttcaag caacaacagc agcacaaaaa acccaacca aacaaaactc
 301 ttgacagaag ctgtgacaac cagaaaggat gcctcataaa ggggaagac tttaactagg
 361 ggcgcgcaga tgtgtgaggc cttttattgt gagagtggac agacatccga gatttcagag
 421 cccatattc gagcccgtg gaatcccgcg gcccccagcc agagccagca tgcagaacag
 481 tcagcggga gtgaatcagc tggtggtgt ctttgtcaac gggcggccac tgccggactc
 541 cacccggcag aagattgtag agctagctca cagcgggggcc cggccgtgcg acatttcccg
 601 aattctgcag gtgtccaacg gatgtgtgag taaaattctg ggcaggtatt acgagactgg
 661 ctccatcaga cccagggcaa tcggtggtag taaaccgaga gtagcgactc cagaagttgt
 721 aagcaaaata gccagtata agcgggagtg cccgtccatc tttgcttggg aaatccgaga
 781 cagattactg tccgaggggg tctgtaccaa cgataacata ccaagcgtgt catcaataaa
 841 cagagttctt cgcaacctgg ctagcgaaaa gcaacagatg ggcgcagacg gcatgtatga
 901 taaactaagg atgttgaacg ggcagaccgg aagctgggc accgccctg gttggtatcc
 961 ggggacttcg gtgccaggc aacctacgca agatggctgc agcaacagg aaggagggg
1021 agagaatacc aactccatca gttccaacgg agaagattca gatgaggctc aaatgcgact
1081 tcagctgaag cggaagctgc aagaaatag aacatccttt acccaagagc aaattgaggc
1141 cctggagaaa gagtttgaga gaacccatta tccagatgtg tttgcccgag aagactagc
1201 agccaaaata gatctacctg aagcaagaat acaggtatgg ttttctaatc gaaggggcaa
1261 atggagaaga gaagaaaaac tgaggaatca gagaagacag gccagcaaca cacctagtca
1321 tattcctatc agcagtagtt tcagcaccag tgtctaccaa cccattccac aaccaaccac
1381 accggttttcc tcttcacat ctggctccat gttgggccga acagacacag ccctcacaaa
1441 cacctacagc gctctgcgc ctatgccag cttcaccatg gcaaataacc tgcctatgca
1501 accccagtc ccagccaga cctcctcata tcctgcatg ctgcccacca gccttcggt
1561 gaatgggcgg agttatgata cctacacccc ccacatatg cagacacacc tgaacagtca
```

Fig. 13

```
1621 gcaatgggc acctgggca ccacttcaac aggactcatt tccctggtg tgtcagttcc
1681 agttcaagtt ccggaagtg aacctgatat gtctcaatac tggccaagat tacagtaaaa
1741 aaaaaaaaa aaaaaaaag gaaaggaaat attgtgttaa ttcagtcagt gactatgggg
1801 acacaacagt tgagctttca ggaaagaaag aaaaatggct gttagagccg cttcagttct
1861 acaattgtgt cctgtattgt accactgggg aaggaatgga cttgaaacaa ggacctttgt
1921 atacagaagg cacgatatca gttggaacaa atcttcattt tggtatccaa actttattc
1981 attttggtgt attatttgta aatgggcatt tgtatgttat aatgaaaaaa agaacaatgt
2041 agactggatg gatgtttgat ctgtgttggt catgaagttg ttttttttt tttaaaaag
2101 aaaaccatga tcaacaagct tgccacgaa tttaagagtt ttatcaagat atatcgaata
2161 cttctaccca tctgttcata gtttatggac tgatgttcca agtttgtatc attcctttgc
2221 atataattaa acctggaaca acatgcacta gatttatgtc agaaatatct gttggttttc
2281 caaaggttgt taacagatga agtttatgtg caaaaaaggg taagatataa attcaaggaa
2341 gaaaaaagt tgatagctaa aaggtagagt gtgtcttcga tataatccaa tttgttttat
2401 gtcaaaatgt aagtatttgt cttccctaga aatcctcaga atgatttcta taataaagtt
2461 aattcatttt atatttgaca agaatatatga tgttttatac acattttcat gcaatcatac
2521 gtttcttttt tggccagcaa aagttaattg ttcttagata tagttgtatt actgttcacg
2581 gtccaatcat tttgtgcatc tagagttcat tcctaatcaa ttaaaagtgc ttgcaagagt
2641 tttaaactta agtgtttga agttgttcac aactacatat caaaattaac cattgttgat
2701 tgtaaaaaac catgccaaag cctttgtatt tcctttatta tacagttttc ttttaacct
2761 tatagtgtgg tgttacaaat tttatttcca tgttagatca acattctaaa ccaatggtta
2821 cttcaacaca cactctgttt tacatcctga tgatccttaa aaaataatcc ttatagatac
2881 cataaatcaa aaacgtgtta gaaaaaatt ccacttacag cagggtgtag atctgtgcc
2941 atttataccc acaacatata tacaaaatgg taacatttcc cagttagcca tttaattcta
3001 aagctcaaag tctagaaata atttaaaaat gcaacaagcg attagctagg aattgttttt
3061 tgaattagga ctggcatttt caatctgggc agatttccat tgtcagccta tttcaacaat
3121 gatttcactg aagtatattc aaaagtagat ttcttaaagg agactttctg aaagctgttg
3181 ccttttcaa ataggccctc tccctttttct gtctccctcc ccttgcaca agaggcatca
3241 tttccattg aaccactaca gctgttccca tttgaatctt gctttctgtg cggttgtgga
```

Fig. 13 (continued)

```
3301 tggttggagg gtgagggggg gatgtgcat gtcaaggaat aatgagcaca gacacatcaa
3361 cagacaacaa caaagcagac tgtgactggc cggtgggaat taaaggcctt cagtcattgg
3421 cagcttaagc caaacattcc caaatctatg aagcagggcc cattgttggt cagtgttat
3481 ttgcaatgaa gcacagttct gatcatgttt aaagtggagg cacgcaggc aggagtgctt
3541 gagcccaagc aaaggatgga aaaaataag ccttgttgg gtaaaaagg actgtctgag
3601 actttcattt gttctgtgca acatataagt caatacagat aagtcttcct ctgcaaactt
3661 cactaaaaag cctggggtt ctggcagtct agattaaaat gcttgcacat gcagaaacct
3721 ctggggacaa agcacactt ccactgaatt atactctgct ttaaaaaat cccaaaagc
3781 aaatgatcag aaatgtagaa attaatggaa ggattaaac atgaccttct cgttcaatat
3841 ctactgtttt ttagttaagg aattacttgt gaacagataa ttgagattca ttgctccggc
3901 atgaaatata ctaataattt tattccacca gagttgctgc acatttggag acaccttcct
3961 aagttgcagt ttttgtatgt gtgcatgtag ttttgttcag tgtcagcctg cactgcacag
4021 cagcacattt ctgcagggga gtgagcacac atacgcactg ttggtacaat tgccggtgca
4081 gacatttcta cctcctgaca ttttgcagcc tacattccct gagggctgtg tgctgaggga
4141 actgtcagag aagggctatg tgggagtgca tgccacagct gctggctgga ttacttcttc
4201 cttctgctg gctgtaattt ccaccacggt caggcagcca gttccggcc acggttctgt
4261 tgtgtagaca gcagagactt tggagacccg gatgtgcac gccaggtgca agaggtggga
4321 atgggagaaa aggagtgacg tgggagcgga gggtctgtat gtgtgcactt gggcacgtat
4381 atgtgtgctc tgaaggtcag gattgccagg gcaaagtagc acagtctggt atagtctgaa
4441 gaagcggctg ctcagctgca gaagccctct ggtccggcag gatgggaacg gctgccttgc
4501 cttctgccca caccctaggg acatgagctg tccttccaaa cagagctcca ggcactctct
4561 tgggacagc atggcaggct ctgtgtggta gcagtgcctg ggagttggcc tttactcat
4621 tgttgaaata attttgttt attatttatt taacgataca tatatttata tacttatcaa
4681 tggggtatct gcagggatgt tttgacacca tcttccagga tggagattat ttgtgaagac
4741 ttcagtagaa tcccaggact aaacgtctaa attttttctc caaacttgac tgacttggga
4801 aaaccaggtg aatagaataa gagctgaatg tttaagtaa taaacgttca aactgctcta
4861 agtaaaaaaa tgcattttac tgcaatgaat ttctagaata ttttttcccc aaagctatgc
4921 ctcctaaccc ttaaatggtg aacaactggt ttcttgctac agctcactgc catttcttct
```

Fig. 13 (continued)

```
4981 tactatcatc actaggtttc ctaagattca ctcatacagt attatttgaa gattcagctt
5041 tgttctgtga atgtcatctt aggattgtgt ctatattctt ttgcttattt ctttttactc
5101 tgggctctc atactagtaa gattttaaaa agcctttct tctctgtatg tttggctcac
5161 caaggcgaaa tatatattct tctcttttc attttctcaag aataaactc atctgctttt
5221 ttgtttct gtgtttggc ttggtactga atgactcaac tgctcggtt taaagttcaa
5281 agtgtaagta cttagggtta gtactgctta tttcaataat gttgacggtg actatcttg
5341 gaaagcagta acatgctgtc ttagaaatga cattaataat gggcttaaac aaatgaatag
5401 gggggtcccc ccactctcct tttgtatgcc tatgtgtgtc tgatttgtta aagatggac
5461 agggaattga ttgcagagtg tcgcttcctt ctaaagtagt tttatttgt ctactgttag
5521 tatttaaaga tcctggaggt ggacataagg aataaatgga agagaaaagt agatattgta
5581 tggtggctac taaaaggaaa ttcaaaaagt cttagaaccc gagcacctga gcaaactgca
5641 gtagtcaaaa tatttatctc atgttaaaga aaggcaaatc tagtgtaaga aatgagtacc
5701 atataggggtt ttgaagttca tatactagaa acacttaaaa gatatcattt cagatattac
5761 gtttggcatt gttcttaagt atttatatct ttgagtcaag ctgataatta aaaaaaatct
5821 gttaatggag tgtatattc ataatgtatc aaaatggtgt ctataccttaa ggtagcatta
5881 ttgaagagag atatgttat gtagtaagtt attaacataa tgagtaacaa ataatgtttc
5941 cagaagaaag gaaaacacat ttcagagtg cgttttatc agaggaagac aaaaatacac
6001 accctctcc agtagctat tttacaaag ccggccagt gaattagaaa aacaaagcac
6061 ttggatatga ttttggaaa gcccaggtac acttattatt caaatgcac ttttactgag
6121 ttgaaaagt ttcttttata tttaaaataa gggttcaaat atgcatattc aatttttata
6181 gtagttatct atttgcaaag catatattaa ctagtaattg gctgttaatt ttatagacat
6241 ggtagccagg gaagtatatc aatgacctat taagtatttt gacaagcaat ttacatatct
6301 gatgacctcg tatctctttt tcagcaagtc aaatgctatg taattgttcc attgtgtgtt
6361 gtataaaatg aatcaacacg gtaagaaaaa ggttagagtt attaaaataa taaactgact
6421 aaaatactca tttgaattta ttcagaatgt tcataatgct ttcaaaggac atagcagagc
6481 ttttgtggag tatccgcaca acattattta ttatctatgg actaaatcaa ttttttgaag
6541 ttgctttaaa atttaaaagc acctttgctt aatataaagc ccttaatttt taactgacag
6601 atcaattctg aaactttatt ttgaaaagaa aatggggaag aatctgtgtc tttagaatta
```

Fig. 13 (continued)

```
6661 aaagaaatga aaaaaataaa cccgacattc taaaaaaata gaataagaaa cctgattttt
6721 agtactaatg aaatagcggg tgacaaaata gttgtctttt tgattttgat cacaaaaaat
6781 aaactggtag tgacaggata tgatggagag atttgacatc ctggcaaatc actgtcattg
6841 attcaattat tctaattctg aataaaagct gtatacagta aaa
```

Fig. 13 (continued)

Protein Sequence Pax6a ΔHD (SEQ ID NO:117)

MQNSHSGVNQLGGVFVNGRPLPDSTRQKIVELAHSGARPCDISRILQVSNGCV
SKILGRYYETGSIRPRAIGGSKPRVATPEVVSKIAQYKRECPSIFAWEIRDRLLSE
GVCTNDNIPSVSSINRVLRNLASEKQQMGADGMYDKLRMLNGQTGSWGTRPG
WYPGTSVPGQPTQDGCQQQEGGGENTNSISSNGEDSDEAQMRLQLKRKKLR
NQRRQASNTPSHIPISSSFSTSVYQPIPQPTTPVSSFTSGSMLGRTDTALTNTYS
ALPPMPSFTMANNLPMQPPVPSQTSSYSCMLPTSPSVNGRSYDTYTPPHMQT
HMNSQPMGTSGTTSTGLISPGVSVPVQVPGSEPDMSQYWPRLQ

Fig. 14 mRNA sequence of Pax6a ΔHD (SEQ ID NO:118)

```
   1   cccatattc gagccccgtg gaatccggcg gccccagcc agagccagca tgcagaacag
  61   tcacagcgga gtgaatcagc tcggtggtgt ctttgtcaac gggcggccac tgccggactc
 121   cacccggcag aagattgtag agctagctca cagcgggggcc cggccgtgcg acatttccg
 181   aattctgcag gtgtccaacg gatgtgtgag taaaattctg ggcaggtatt acgagactgg
 241   ctccatcaga cccaggcaa tggtggtag taaaccgaga gtagccgactc cagaagttgt
 301   aagcaaaata gcccagtata agcgggagtg ccgtccatc tttgcttggg aaatccgaga
 361   cagattactg tccgaggggg tctgtaccaa cgataacata ccaagcgtgt catcaataaa
 421   cagagttctt cgcaacctgg ctagcgaaaa gcaacagatg ggcgagacg gcatgtatga
 481   taaactaagg atgttgaacg ggcagacgg aagctgggc accgccctg gttggtatcc
 541   ggggacttcg gtgccagggc aacctacgca agatggctgc cagcaacagg aaggaggggg
 601   agaaatacc aactccatca gttccaacgg agaagattca gatgaggctc aaatgcgact
 661   tcagctgaag cggaag---- ---------- ---------- ---------- ----------
       ---------- ---------- ---------- ---------- ---------- ----------
       ---------- ---------- ---------- ---------- ---------- ----------
 677   ---------- ------aaac tgaggaatca gagaagacag gccagcaaca cacctagtca
 721   tatcctatc agcagtagtt tcagcacag tgtctaccaa ccaattccac aaccaccac
 781   accggttcc tccttcacat ctggctccat gttgggccga acagacacag ccctcacaaa
 841   cacctacagc gctctgccgc ctatgccag cttcaccatg gcaaataacc tgcctatgca
 901   accccagtc ccagccaga cctcctcata ctcctgcatg ctgccacca gccttggt
 961   gaatgggcgg agttatgata cctacaccc ccacatatg cagacacaca tgaacagtca
1021   gccaatgggc acctcgggca cacttcaac aggactcatt tccctggtg tgtcagttcc
1081   agttcaagtt ccggaagtg aacctgatat gtctcaatac tggccaagat tacagtaaaa
```

Fig. 15

Protein Sequence of Pax6ΔPAI (SEQ ID NO:119)

MRVATPEVVSKIAQYKRECPSIFAWEIRDRLLSEGVCTNDNIPSVSSINRVLRNL
ASEKQQMGADGMYDKLRMLNGQTGSWGTRPGWYPGTSVPGQPTQDGCQQ
QEGGGENTNSISSNGEDSDEAQMRLQLKRKLQRNRTSFTQEQIEALEKEFERT
HYPDVFARERLAAKIDLPEARIQVWFSNRRAKWRREEKLRNQRRQASNTPSHI
PISSSFSTSVYQPIPQPTTPVSSFTSGSMLGRTDTALTNTYSALPPMPSFTMAN
NLPMQPPVPSQTSSYSCMLPTSPSVNGRSYDTYTPPHMQTHMNSQPMGTSG
TTSTGLISPGVSVPVQVPGSEPDMSQYWPRLQ

Fig. 16 mRNA Sequence of Pax6ΔPAI (SEQ ID NO:120)

```
   1 cccaatattc gagcccgtg gaatcccgcg gccccagcc agagccagca tg--------
                                                              ----------
                                                              ----------
                                                              ----------
  53 ---------- ---------- ---------- --------aga gtagcgactc cagaagttgt
  76 aagcaaaata gcccagtata agcgggagtg cccgtccatc tttgcttggg aaatccgaga
     136 cagattactg tccgagggg tctgtaccaa cgataacata ccaagcgtgt
catcaataaa
 196 cagagttctt cgcaacctgg ctagcgaaaa gcaacagatg ggcagacg gcatgtatga
 256 taaactaagg atgttgaacg ggcagacgg aagctggggc acccgccctg gttggtatcc
 316 ggggacttcg gtgccagggc aacctacgca agatggctgc cagcaacagg aaggaggggg
 376 agagaatacc aactccatca gttccaacgg agaagattca gatgaggctc aaatgcgact
 436 tcagctgaag cggaagctgc aaagaaatag aacatccttt acccaagagc aaattgaggc
 496 cctggagaaa gagtttgaga gaacccatta tccagatgtg tttgcccgag aaagactagc
 556 agccaaaata gatctacctg aagcaagaat acaggtatgg tttctaatc gaagggccaa
 616 atggagaaga gaagaaaaac tgaggaatca gagaagacag gccagcaaca cacctagtca
 676 tattcctatc agcagtagtt tcagcaccag tgtctaccaa ccaattccac aacccaccac
 736 accggtttcc tccttcacat ctggctccat gttgggccga acagacacag ccctcacaaa
 796 cacctacagc gtctctgccg ctatgcccag cttcaccatg gcaaataacc tgcctatgca
 856 accccagtc ccagccaga cctctcata ctctgcatg ctgccacca gccttcggt
 916 gaatgggcgg agttatgata cctacacccc ccacatgc agacacaca tgaacagtca
 976 gccaatgggc acctcgggca ccacttcaac aggactcatt tccctggtg tgtcagttcc
1036 agtcaagtt ccggaagtg aacctgatat gtctcaatac tggccaagat tacagtaaaa
```

Fig. 17

Protein Sequence of Pax6ΔPD (SEQ ID NO:121)

MRLQLKRKLQRNRTSFTQEQIEALEKEFERTHYPDVFARERLAAKIDLPEARIQV
WFSNRRAKWRREEKLRNQRRQASNTPSHIPISSSFSTSVYQPIPQPTTPVSSFT
SGSMLGRTDTALTNTYSALPPMPSFTMANNLPMQPPVPSQTSSYSCMLPTSPS
VNGRSYDTYTPPHMQTHMNSQPMGTSGTTSTGLISPGVSVPVQVPGSEPDMS
QYWPRLQ

Fig. 18 mRNA Sequence of Pax6ΔPD (SEQ ID NO:122)

```
  1 cccatattc gagcccgtg aatccagcg gccccagcc agagccagc-----------
                                                     ------------
 ... (gaps)
 50 ----------- ----------- ----------- ----------- -----------  --atgcgact
 58 tcagctgaag cggaagctgc aagaaatag aacatccttt acccaagagc aaattgaggc
118 cctggagaaa gagtttgaga gaacccatta tccagatgtg tttgcccgag aagactagc
178 agccaaaata gatctacctg aagcaagaat acaggtatgg ttttctaatc gaagggccaa
238 atggagaaga gaagaaaaac tgaggaatca gagaagacag gccagcaaca cacctagtca
298 tattcctatc agcagtagtt tcagcaccag tgtctaccaa ccaattccac aacccaccac
358 accggtttcc tccttcacat ctggctccat gttgggccga acagacacag ccctcacaaa
418 cacctacagc gctctgccgc ctatgcccag cttcaccatg gcaaataacc tgcctatgca
478 accccccagtc cccagccaga cctcctcata ctcctgcatg ctgcccacca gccttcggt
538 gaatggggcgg agttatgata cctacaccc cccacatatg cagacacaca tgaacagtca
598 gccaatgggc acctcggca ccacttcaac aggactcatt tccctggtg tgtcagttcc
658 agttcaagtt cccggaagtg aacctgatat gtctcaatac tggccaagat tacagtaaaa
```

Fig. 19

Protein Sequence of Pax6bD/N (SEQ ID NO:123)

MQNSHSGVNQLGGVFVNGRPLPDSTRQKIVELAHSGARPCDISRILQTHADAK
VQVLDNQNVSNGCVSKILGRYYETGSIRPRAIGGSKPRVATPEVVSKIAQYKRE
CPSIFAWEIRDRLLSEGVCTNDNIPSVSSINRVLRNLASEKQQMGADGMYDKLR
MLNGQTGSWGTRPGWYPGTSVPGQPTQDGCQQQEGGGENTNSISSNGEDS
DEAQMRLQLKRKLQRNRTSFTQEQIEALEKEFERTHYPDVFARERLAAKIDLPE
ARIQVWFSNRRAKWRREEKLRNQRRQASNTPSHIPISSSFSTSVYQPIPQPTTP
VSSFTSGSMLGRTDTALTNTYSALPPMPSFTMANNLPMQ

Fig. 20 mRNA Sequence of Pax6b D/N (SEQ ID NO:124)

```
   1 ccagccagag ccagcatgca gaacagtcac agcggagtga atcagctggg tggtgtcttt
  61 gtcaacgggc ggccactgcc ggactccacc cggcagaaga ttgtagagct agctcacagc
 121 gggccccggc cgtgcgacat ttcccgaatt ctgcagaccc atgcagatgc aaaagtccaa
 181 gtgctggaca atcaaaacgt gtccaacgga tgtgtgagta aaattctggg caggtattac
 241 gagactggct ccatcagacc cagggcaatc ggtggtagta aacgagagt agcgactcca
 301 gaagttgtaa gcaaatagc ccagtataag cgggagtgcc cgtccatctt tgcttgggaa
 361 atccgagaca gattactgtc cgaggggtc tgtaccaacg ataacatacc aagcgtgtca
 421 tcaataaaca gagttcttcg caacctgggt agcgaaaagc aacagatggg cgcagacggc
 481 atgtatgata aactaaggat gttgaacggg cagaccggaa gtggggcac ccgccctggt
 541 tggtatccgg ggacttcggt gccagggcaa cctacgcaag atggctgcca gcaacaggaa
 601 ggaggggag agaataccaa ctccatcagt tccaacggag aagattcaga tgaggctcaa
 661 atgcgacttc agctgaagcg gaagctgcaa agaaatagaa catcctttac ccaagagcaa
 721 attgaggccc tggagaaaga gtttgagaga accattatc cagatgtgtt tgcccgagaa
 781 agactagcag ccaaaataga tctacctgaa gcaagaatac aggtatggtt ttctaatcga
 841 agggccaaat ggagaagaga agaaaactg aggaatcaga gaagacaggc cagcaacaca
 901 cctagtcata ttcctatcag cagtagtttc agcaccagtg tctaccaacc aattccacaa
 961 cccaccacac cggtttcctc cttcacatct ggctccatgt tgggccgaac agacacagcc
1021 ctcacaaaca cctacagcgc tctgccgcct atgccagct tcaccatggc aaataaacctg
1081 cctatgcaa- ---------- ---------- ---------- ---------- ----------
     ---------- ---------- ---------- ---------- ---------- ----------
     ---------- ---------- ---------- ---------- ---------- ----------
1090 ---taaaaaa
```

Fig. 21

EXOGENOUS PAX6 NUCLEIC ACID EXPRESSION IN PRIMATE NEURAL STEM CELLS MAINTAINS PROLIFERATION WITHOUT DIFFERENTIATION

CROSS-REFERENCE TO RELATED APPLICATION

This application is a continuation of U.S. patent application Ser. No. 12/849,249 filed on Aug. 3, 2010, which claims priority from U.S. provisional patent application Ser. No. 61/273,373, filed on Aug. 3, 2009, and U.S. provisional patent application Ser. No. 61/273,690, filed on Aug. 6, 2009. All of these applications are incorporated by reference herein.

STATEMENT REGARDING FEDERALLY SPONSORED RESEARCH OR DEVELOPMENT

This invention was made with government support under NS045926 awarded by the National Institutes of Health. The government has certain rights in the invention.

BACKGROUND

Somatic stem cells are undifferentiated cells that can renew themselves and can also differentiate to specialized cell types of a tissue or organ, such as neural stem cells and hematopoietic stem cells. While stem cells derived from an early embryo, known as embryonic stem cells (ESCs), can be maintained in culture for an extended period without losing their differentiation potential (Thomson et al., *Science*, 1998, 282: 1145-1147; Evans & Kaufamn, *Nature*, 1981, 5819: 154-156), somatic stem cells like brain (neural) or blood stem cells gradually lose their differentiation potentials when cultured for a long period of time. A brain stem cell can generate all types of cells in the brain and spinal cord but after expansion it can only generate neural cells of a particular brain region or even particular cell types of a brain region (Temple, *Nat. Rev. Neurosci.*, 2001, 2: 513-520; Gage, *Science*, 2000, 287: 1433-1438).

Maintenance of ESCs depends on the transcription network orchestrated by stem cell (pluripotent) transcription factors including Oct4, Nanog, and Sox2. These transcription factors block developmental genes while activating stem cell genes, thus inhibiting differentiation and maintaining the stem cell state (Boyer et al., *Cell*, 2005, 122: 947-956). Activation of this stem cell transcription network reprograms somatic (e.g. skin) cells to stem cells, also known as induced pluripotent stem cells (iPSCs) (Yu et al., *Science*, 2007, 318: 1917-1920; Takahashi et al., *Cell*, 2007, 131: 861-872).

Transplantation of hESC-differentiated neural derivatives often ends up with over-growth of the grafts (Roy et al., *Nat. Med*, 2006, 12: 1259-1268; Sonntag et al., *Stem Cells*, 2007, 25: 411-418). hESC derived neurons and glia are a desirable source of cells for replacement therapy. However, transplantation of stem cell derived neural cells for therapeutic purposes is often confounded by the tumorigenic potential of undifferentiated neuroepithelial cells.

Needed in the art is a method of maintaining primate somatic stem cells, such as brain stem cells, in culture without losing differentiation potential. Like the generation of iPSCs by pluripotent transcription factors, transcription factor(s) critical for maintaining neural stem cells would need to be identified and regulated. Also needed in the art is a method of decreasing the possibility of tumor formation in a transplant.

SUMMARY OF THE INVENTION

In one embodiment, the present invention is a primate primitive neural stem cell (primate pNSC) wherein the cell overexpresses Pax6.

In another embodiment, the present invention is a population of the primate pNSCs described above, wherein the cells overexpress Pax6. In a preferred embodiment, the cells continue to proliferate without differentiating, preferably for at least one week. Most preferably, the cells continue to proliferate without differentiating for at least two weeks. In a preferred embodiment, the cells are human pNSCs.

In yet another embodiment, the present invention is a method of creating a population of primate pNSCs from primate embryonic stem cells (ESCs) or induced pluripotent stem cells (iPSCs) comprising the step of overexpressing Pax6 within a population of ESCs or iPSCs, wherein the expression level of Pax6 is sufficient to suppress the expression of Sox1 and Oct4. In one embodiment, the primate is human.

In a preferred embodiment, the overexpression of Pax6 is via an inducible system. In another preferred embodiment, the overexpression of Pax6 is via a lentiviral vector, preferably an inducible lentiviral vector. In one preferred embodiment, the overexpression of Pax6 is under the control of elongation factor 1α promoter in the lentiviral vector. In yet another preferred embodiment, the overexpression of Pax6 is via adding recombinant Pax6 to the cells directly.

In yet another embodiment, the present invention is method of creating a population of primate regional neural stem cells comprising the steps of overexpressing Pax6 within a population of primate ESCs or iPSCs wherein the expression level of Pax6 is sufficient to suppress the expression of Sox1 and Oct4, and suppressing Pax6 expression and differentiating the cells into regional neural stem cells. Preferably, the regional neural stem cells are selected from the group consisting of forebrain cells, midbrain cells and spinal cells. Preferably, the primate is human.

In yet another embodiment, the present invention is a method of creating a population of primate pNSCs from primate regional neural stem cells comprising the step of overexpressing Pax6 within a population of primate regional neural stem or progenitor cells wherein the expression level of Pax6 is sufficient to reprogram the cells to the primate pNSC stage. Preferably, the primate is human.

In yet another embodiment, the present invention is a method of treating a patient with brain tumor or overgrowth of cell transplants by suppressing Pax6 expression comprising the steps of inhibiting Pax6 expression in the tumor cells or the overgrown cell transplants. Preferably, the suppression of Pax6 expression is through Pax6 RNAi, block of Pax6 transcription or acceleration of Pax6 degradation.

Other objects, advantages and features of the present invention will become apparent from the following specification taken in conjunction with the accompanying drawings.

BRIEF DESCRIPTION OF DRAWINGS

The invention will be better understood and features, aspects and advantages other than those set forth above will become apparent when consideration is given to the following detailed description thereof. Such detailed description makes reference to the following drawings, wherein:

(FIG. 1A and FIG. 1B) Western blotting shows temporal expression of Pax6 and Sox1 along human and mouse ESC differentiation, respectively. Arrowheads, Pax6a (lower) and Pax6b (upper). (FIG. 1C) Pax6 and Sox2, but not Sox1, are expressed in pNSCs in the neural plate of day 18 and day 21 human fetuses and Sox1 is detected in regional NSCs of the brain and neural tube of day 26 human fetus. (FIG. 1D) Sox1 and Sox2 are expressed throughout the mouse neural plate (pNSCs) and neural tube (regional NSCs) from day 8 to 10.5 whereas Pax6 is absent in day 8 embryos but present in the forebrain and neural tube at day 10.5.

(FIG. 4A) hESC lines expressing inducible Pax6 isoforms. (FIG. 4B) GFP (control) is induced 48h after Dox treatment. (FIG. 4C) Pax6-GFP is induced after 48h of Dox treatment. Note Pax6-GPF in nuclei. (FIG. 4D) hESC lines expressing inducible Pax6 RNAi. (FIG. 4E) After differentiation to pNSCs at day 10, induction and maintenance of Pax6 by doxycycline treatment for 2 weeks kept growth factor-independent proliferation and suppressed Sox1 expression. 3 days after Dox removal, many cells began to express Sox1. These data indicate that maintaining of NSCs in a primitive state can be achieved by Pax6 overexpression and driving the cells out of the primitive state can also be achieved by shutting off Pax6 expression. In addition, the inducible transgenic overexpression/knockdown tool represents a useful strategy to control the cell fates.

(FIG. 5A) hESCs were infected with lentiviruses bearing control (Luc) and Pax6b RNAi, and stable lines were established thereafter. Pax6b RNAi cells can not be maintained in a NSC state at day 17 as demonstrated by massive spontaneous differentiation. (FIG. 5B) Transiently infection of Pax6 RNAi lentiviruses targeting both Pax6a and Pax6b in day 14 NSCs caused massive cell death and neuronal differentiation.

(FIG. 6A) Human cortical NSCs are infected with inducible lentiviruses expression of GFP control or Pax6. After withdrawal of Dox and five days of treatment with retinoid acid (RA), the GFP (control) expression regional NSCs stop growing whereas the Pax6-NSCs continue to grow with neurite extension. (FIG. 6B) Many of the Pax6-NSCs were positive for spinal cord marker, HoxB4, after treatment with RA but none of the GFP-NSCs express HoxB4. Since cortical NSCs are fixed to a cortical fate, the fact that Pax6 overexpression endows the cells with spinal cord differentiation potential indicates that the cells are reprogrammed to a primitive stage before RA mediated caudalization.

(FIG. 7A) Pax6-expressing pNSCs were present in the dopamine neuron differentiation cultures (for 35 days) although the numbers gradually decrease over time. Midbrain TH positive neurons are lost in Parkinson's disease and TH neurons are specifically used for replacement therapy for Parkinson's disease. (FIG. 7B) One case of tumor formation after transplantation of the cells containing above mentioned pNSCs. These Pax6 positive cells are proliferating and are tumorigenic if they are transplanted to the brain of host mice. Arrow shows the tumor and the cells within the tumor are Pax6+/Sox1− pNSCs.

FIG. 9 shows the protein sequence of Pax6a (SEQ ID NO: 112).

FIG. 10 shows the mRNA sequence of Pax6 transcription variant 1 (SEQ ID NO: 113), which encodes Pax6a.

FIG. 11 shows the protein sequence of Pax6b (SEQ ID NO: 114).

FIG. 12 shows the mRNA sequence of Pax6 transcription variant 2 (SEQ ID NO: 115), which encodes Pax6b.1

FIG. 13 shows the mRNA sequence of Pax6 transcription variant 3 (SEQ ID NO: 116), which encodes Pax6a.

FIG. 14 shows the protein sequence of Pax6aΔHD (SEQ ID NO: 117), human Pax6a mutant with the homeodomain deleted.

FIG. 15 shows the mRNA sequence of Pax6aΔHD (SEQ ID NO: 118).

FIG. 16 shows the protein sequence of Pax6ΔPAI (SEQ ID NO: 119), human Pax6a mutant with the N-terminal Paired Domain deleted.

FIG. 17 shows the mRNA sequence of Pax6ΔPAI (SEQ ID NO: 120).

FIG. 18 shows the protein sequence of Pax6ΔPD (SEQ ID NO: 121), human Pax6a mutant with the entire Paired Domain deleted.

FIG. 19 shows the mRNA sequence of Pax6ΔPD (SEQ ID NO: 122).

FIG. 20 shows the protein sequence of Pax6bD/N (SEQ ID NO: 123), a Pax6b dominant negative mutant in which the PST transactivation domain is deleted.

FIG. 21 shows the mRNA sequence of Pax6bD/N (SEQ ID NO: 124).

DESCRIPTION OF THE PRESENT INVENTION

The inventors have discovered that the transcription factor Pax6 is necessary and sufficient for induction of primate pNSCs, preferably human pNSCs, from ESCs (hESCs) and iPSCs, a role that does not apply to Pax6 in other non-primate animals (e.g. mice, Simpson and Price, *Bioessays*, 2002, 24: 1041-1051). Additionally, Pax6 is important not just in induction but also in maintenance of stem cells in a primitive undifferentiated state.

Pax6 belongs to the paired box (Pax) gene family that plays a critical role in the development of several organ systems, including eye, pancreas and cerebrum (Chi et al., Trends Genet., 2002, 18: 41-47). Pax6 is highly conserved, with 100% amino acid sequence homology between mouse and human, suggesting important functions across species. There are two main Pax6 isoforms created by alternative mRNA splicing of the fifth exon. Pax6b is produced by insertion of exon5a into the paired domain and is 14 amino acids longer than Pax6a with different DNA binding specificity (Epstein et al., Genes Dev., 1994, 8: 2022-2034; Kozmik et al., EMBO J., 1997, 16: 6793-6803).

The inventors have discovered that the way in which Pax6 acts is similar in function to the way Oct4 acts in ESCs. Pax6 represses stem cell genes, including Oct4 and Nanog, and induces neuroectoderm genes so that the ESCs convert to NSCs. At the same time, Pax6 blocks expression of genes involved in later-stage neural development, including Sox1, thus preventing NSCs from further differentiation. By doing so Pax6-expressing NSCs are in a primitive stage and capable of full-range neural differentiation, including the generation of projection neurons of the brain and spinal cord. During embryo development or expansion in culture, the primitive NSCs gradually down-regulate Pax6 and turn on late-stage neural genes, thus becoming committed neural progenitors that only generate particular types of neurons and glia.

The inventors discovered that the Pax6a isoform upregulates neural genes and directs the cells to primate pNSCs, although both Pax6a and Pax6b isoforms bind to the pluripotent gene promoters and down-regulate pluripotent genes.

Figure 22:
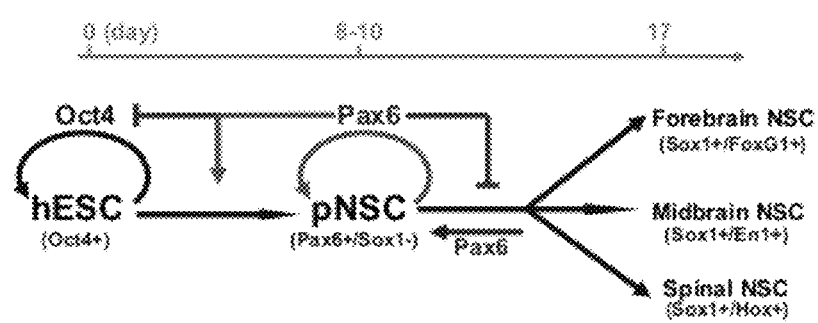
FIG. 22 is a scheme showing Pax6 in induction, maintenance, and reprogramming of primate pNSCs.

FIG. 22 graphically describes the pathway that the inventors have discovered. This path is integral to the present invention. Overexpression of the Pax6 factor in primate pluripotent stem cells, such as hESCs and iPSCs, creates a population of undifferentiated dividing pNSCs. These pNSCs can be differentiated to neurons and supporting cells of the nervous system by decreasing Pax6 and under appropriate differentiation conditions.

FIG. 22 shows Pax6 in induction, maintenance, and reprogramming of primate pNSCs. In one embodiment, hESCs differentiate to regional NSCs via a transient intermediate stage, pNSCs, that express Pax6 at day 8-10. Pax6 induces hESC differentiation towards neural cells partly by inhibiting stem cell genes like Oct4 and keeps the NSCs in the primitive stage partly by inhibiting further differentiation to regional progenitors. Forced Pax6 expression reverses regional progenitors to pNSCs.

hESC derived neurons and glia are a desirable source of cells for replacement therapy. However, transplantation of stem cell derived neurons for therapeutic purposes is often confounded by the tumorigenic potential of undifferentiated neuroepithelial cells and thus ends up with over-growth of the grafts (Roy et al., *Nat. Med*, 2006, 12: 1259-1268; Sonntag et al., *Stem Cells*, 2007, 25: 411-418). These neuroepithelial cells or pNSCs are maintained in their state by the expression of Pax6. Thus, Pax6 downregulation in cultures prior to transplant will ensure that the pNSCs either differentiate or die, thus decreasing the possibility of tumor formation in the transplant.

Yet another embodiment of the invention recognizes that down-regulating Pax6 is also an efficient and safe way to control brain tumors which initiate from transformed pNSCs and show an increased expression of Pax6.

By "stem cell", we mean to include all primate pluripotent stem cells. For example, we include both ESCs, such as hESC line H9, and iPSCs (Yu et al., *Science*, 2007, 318: 1917-1920; Takahashi et al., *Cell*, 2007, 131: 861-872).

By "primitive neural stem cell", we mean Pax6$^+$/Sox1$^-$ cells that are characterized by early rosette morphology and have the full potential to differentiate into all types of neural cells in the body.

By "regional neural stem cell", we mean Sox1$^+$ neural progenitors with limited potential to differentiate into some but not all types of neural cells, including forebrain neural stem cells, midbrain neural stem cells and spinal neural stem cells. We mean to use the terms "progenitors" and "stem cells" interchangeably. For example, we mean to use the terms "regional neural progenitors" and "regional neural stem cells" interchangeably.

In one embodiment, one can separate pNSCs from regional NSCs using the gene panel listed in Table 1 in Example 2. Expressions of these genes are down-regulated at least four folds in regional NSCs compared to pNSCs.

By "Pax6", we mean the transcription factor paired box gene 6, preferably coordination of both isoforms of Pax6, including isoforms a and b of various species, preferably mammalian species. In one embodiment, one can use isoform a. The mRNA and protein sequences of the two isoforms of human Pax6 can be found at NCBI (NM_000280, NM_001127612, NM_001604). The Pax6 gene is conserved among species (Quiring et al., *Science*, 1994; 265: 785-789), but it is more conserved among mammals than it is in non-mammals. The Pax6 gene can be cloned from most mammalian cells expressing Pax6, such as human, rhesus monkey and mouse cells. We cloned Pax6a and Pax6b genes from the human NSCs differentiated from hESCs. Of course, one may make conservative or benign substitutions, deletions or additions to the native Pax6 sequences and we mean to include these substantially identical sequences in our definitions of "Pax6". For example, one can use Pax6EHD (see SEQ ID NO: 117 for the protein sequence) to direct the differentiation from stem cells to pNSCs.

Zhang et al. (*Cell Stem Cell*, 2010, 7: 90-100) is an academic paper which describes one embodiment of the present invention and is incorporated herein by reference. Briefly, by genetic manipulation of ESCs, the inventors discovered that Pax6 is necessary and sufficient for neuroepithelial (NE) specification from human but not mouse ESCs. The inventors also found that cell lineage specification of ESCs not only requires repression of pluripotent genes but also depends on induction of the target lineage genes.

U.S. Pat. No. 7,588,937, US2008/0206865 and US2008/0227137 are patent or patent publications from the inventor's laboratory and disclose directed differentiation of neural cells. These references are also incorporated herein by reference.

Creation of a Population of Primate pNSC Cells

In one embodiment, the present invention is a population of primate pNSCs that overexpress Pax6. By "overexpression" of Pax6, we mean any expression over the amount of native Pax6 that is sufficient to convert stem cells to pNSCs. Overexpression of Pax6 will keep the cells in their primitive state, i.e. any Pax6 level that is sufficient to suppress the expression of Sox1 and Oct4. One can test for expression of Sox1 and Oct4 by methods of determining expression level of a gene through a number of methods, e.g. Western Blotting, immunostaining and polymerase chain reaction, which are well known in the art. Note that one can add exogenous Pax6 protein or recombinant Pax6 protein to the cells directly and keep the cells in the primitive state. This is also "overexpression". By "exogenous" protein, we mean proteins produced outside the cell in question. For example, Pax6 protein might be purified and concentrated from human cells and added to the cell in question so that Pax6 is "overexpressed" in that cell. By "recombinant" protein, we mean a protein produced by genetic engineering.

One may wish to test that the cells remain in the primitive state. A preferable way to do that is to test for the suppressed expression of Sox 1 and Oct4, and the full neural range of differentiation potentials.

In one embodiment, the cells are created as follows: hESCs are incubated with Pax6 lentiviruses as described below, and grown on mouse embryonic fibroblast (MEF) feeder layer. Pax6-overexpressed cells gradually lose stem cell genes such as Oct4 and start to express neural genes except Sox1. Meanwhile, Pax6-expressing cells aggregate together to form early rosettes, a typical morphology of pNSCs. The population of pNSCs can be enriched through drug selection, such as blasticidin, G418 and puromycin, depending on which drug resistant gene is present in the lentiviral vector. One can also select for Pax6-positive pNSCs under a fluorescence microscope if a fluorescent protein is fused to Pax6, such as Pax6-GFP fusion protein.

In one embodiment, overexpression of Pax6 is driven by elongation factor (EF) 1α promoter. However, one can use other promoters as substitutes, for example, cytomegalovirus (CMV) promoter. More preferably, an inducible promoter is used and Pax6 is overexpressed using an inducible lentivirus system. Such inducible lentivirus systems are commercially available, for example, Lenti-X™ Tet-On® Advanced (Clontech, Calif.). In a preferred embodiment, Lenti-X™ Tet-On® Advanced is modified by replacing the CMV promoter driving rtTA-Advanced in the pLVX-Tet-On Advanced vector with the EF1α promoter. In this embodiment, expression of Pax6 is induced by doxycycline treatment, and removing doxycycline from the medium shuts off Pax6 expression from the vector.

In another embodiment, overexpression of Pax6 can also be achieved by viral infection, plasmid transfection or recombinant protein treatment of mutated Pax6.

In one embodiment, hESCs grown on MEF feeder layer are used for generating pNSCs. In another embodiment, ESCs are grown without MEF feeder layers. In yet another embodiment, iPSCs are used for generating pNSCs.

Expressing recombinant protein using lentiviral vector is well known in the art. Briefly, lentiviral transfer vector, lentiviral packaging plasmid and vesicular stomatitis virus G protein (VSV-G) would be cotransfected to packaging cells. Preferably, the packaging cells are HEK 293FT cells. 1-3 days after transfection, cell culture medium containing the viral particles is collected and filtered through a 0.45 μm filter to remove cell debris. Preferably, the viral particles are further concentrated by ultracentrifugation.

Other packaging cell lines are also available as substitutes for HEK 293FT cells. For example, NIH/3T3 cells can also be used for virus packaging.

Other types of viruses, for example, adenoviruses and retroviruses, can be used as substitutes. Expression modulation of Pax6 can also be achieved through transfection with plasmids, adding recombinant Pax6 in the medium, activating endogenous Pax6 expression through signaling molecules or small molecule drugs. Methods of plasmid transfection, purifying recombinant protein and small molecule screening are well known in the art.

In another embodiment, a population of primate pNSCs is created by exposing primate ESCs or iPSCs to an effective amount of Pax6 protein such that a population of primate pNSCs is created. Preferably, recombinant Pax6 can be purified and added into the medium in which the cells are cultured. Methods of purifying recombinant protein are well known in the art. Preferably, cells within the population continue to proliferate without differentiating and have the full differentiation potential to differentiate to all types of neural cells. By "effective amount of Pax6 protein", we mean any amount of Pax6 protein that that is sufficient to convert the ESCs or iPSCs to pNSCs. Preferably, approximately 0.1-10.0 μg/ml of Pax6 protein with short peptide conjugation to help protein permibilization is used. Most preferably, approximately 0.5-8.0 μg/ml of Pax6 protein with short peptide conjugation to help protein permeabilization is used (Zhou et al., Cell Stem Cell, 2009, 5: 381-384).

Differentiation of Regional Neural Stem Cells from pNSC Population

In another embodiment, the present invention is a method of creating regional neural stem cells from a primate pNSC population. In one embodiment, overexpression of Pax6 in primate pNSCs is controlled by an inducible promoter, and overexpression of Pax6 is turned off to induce differentiation from the pNSCs. Pax6$^+$/Sox1$^-$ pNSCs will express Sox1 in response to the down-regulation of Pax6, and further differentiation can be achieved. U.S. application Ser. No. 10/928,805, which has been issued as U.S. Pat. No. 7,588,937, discloses methods for directed differentiation of neural cells from Pax6$^+$/Sox1$^-$ pNSCs (incorporated herein).

Creation of Primitive Primate Neural Stem Cell Population from Regional Neural Stem Cells In another embodiment, the present invention is a method of creating primate pNSCs from regional NSCs.

In one specific embodiment, the cells are created as follows: cortical (regional) NSCs, which do not have the potential to generate spinal cord neurons, are infected with Pax6 inducible lentivirus. Pax6 is then overexpressed in the cells through doxycycline treatment. The cortical NSCs are reprogrammed to pNSCs as the cells re-exhibit the potential to generate spinal cord neurons in response to retinoid acid due to Pax6 overexpression. Of course, one could use the method with any regional NSCs.

In other embodiments, overexpression of Pax6 is achieved by infection with other viruses, plasmid transfection, recombinant protein incubation or signaling/small molecule treatment.

Additional Embodiments

In another embodiment, the present invention is a method of increasing/decreasing Pax6 transcriptional activity, stability and its physiological function for generation, maintaining, reprogramming of pNSCs. In one embodiment, one can increase or decrease Pax6 transcriptional activity via regulation of kinases/phosphatases of Pax6 (Yan et al., *J Biol Chem*, 2007, 282: 13954-13965; Kim et al., *J Biol Chem*, 2006, 281: 7489-7497; Mikkola et al., *J Biol Chem*, 1999, 274: 15115-15126). In addition, it has been reported that Pax6 stability can also be regulated by protesome-degradation pathway and mutation at certain Pax6 residues modulates protein proteolysis sensitivity (Tuoc et al., Genes Dev, 2008, 22: 1972-1986; D'Elia et al., Eur J Hum Genet, 2006, 14: 744-751). The preliminary research through transgenic analysis by the inventors has identified specific amino acid residues in the Pax6 protein which upon phosphorylation will either accelerate or block degradation of Pax6 protein. The inventors envision that one can use Pax6 mutants, kinases or phosphatases to regulate the protein stability of Pax6, thus regulating the stem cell fate.

In another embodiment, the present invention is a method of suppressing tumor formation in stem cell transplants by suppressing Pax6 expression. As mentioned earlier, transplantation of hESC-differentiated neural derivatives often resulted in over-growth of the grafts (Roy et al., *Nat. Med.,* 2006, 12: 1259-1268; Sonntag et al., *Stem Cells,* 2007, 25: 411-418). Because Pax6-expressing pNSCs are present in the culture for transplantation, down-regulating Pax6, e.g. through infection with lentivirus coding Pax6 RNA interference (RNAi) would result in death of pNSCs or differentiation of pNSCs to neurons. Thus, tumorigenic tendency or overgrowth of hESC derivative transplants may be prevented by suppressing Pax6 expression. Suppression of Pax6 expression can be achieved many ways, e.g. through RNAi mediated Pax6 knockdown, blockage of endogenous Pax6 production and accelerating Pax6 degradation. Alternatively, small molecules, proteins or RNAi that interfere with Pax6 activity and its downstream effects can be used. Briefly, corresponding kinases, phosphatases or other proteins related to Pax6 activity or stability modulation can be overexpressed in the cells prior to transplantation to minimize Pax6 function. Alternatively, signaling/small molecules, which regulate those kinases, phosphatases or other proteins, can be applied directly to cells. Similar to overexpression of Pax6, this can be achieved by infection with other viruses, plasmid transfection, recombinant protein incubation or signaling/small molecule treatment.

In another embodiment, the present invention is a method of treating brain tumors by suppressing Pax6 expression or function. It is known that some brain tumors result from overgrowth of pNSCs. Targeting Pax6 would be an efficient and safe way to control these brain tumors by causing cells to die or differentiate to neurons. Suppression of Pax6 can be achieved by viruses, plasmids or synthesized double strand RNA mediated Pax6 knockdown in the brain tumors. Suppression of Pax6 can also be achieved by targeting kinases, phosphatases or other related proteins as well as signaling/small molecules systematically or locally as described above.

EXAMPLES

Example 1

In Example 1, we show that Pax6 is uniformly expressed in pNSCs of human fetuses and those differentiated from human embryonic stem cells (hESCs). This is in contrast to the later expression of Pax6 in restricted mouse brain regions. Knockdown of Pax6 blocks pNSC specification from hESCs. Overexpression of either Pax6a or Pax6b, but not Pax6ΔPD, triggers hESC differentiation. However, only Pax6a converts hESCs to pNSCs. In contrast, neither loss nor gain of function of Pax6 affects mouse pNSC specification. Both Pax6a and Pax6b bind to pluripotent gene promoters but only Pax6a binds to pNSC genes during human pNSC specification. These findings indicate that Pax6 is a transcriptional determinant of the human pNSC and suggest that Pax6a and Pax6b coordinate with each other in determining the transition from pluripotency to the pNSC fate in humans by differentially targeting pluripotent and pNSC genes.

Introduction

In mammals, the stepwise cell fate transition during early embryonic development is orchestrated by sequential activation/inactivation of lineage-determining transcription factors (Yamanaka et al., *Dev. Dyn.*, 2006, 235: 2301-2314). Oct4, Sox2, and Nanog are required for maintaining pluripotency of the inner cell mass (ICM) or the epiblast in a blastocyst embryo (Avilion et al., *Genes Dev.*, 2003, 17: 126-140; Chambers et al., *Cell*, 2003, 113: 643-655; Mitsui et al., *Cell*, 2003, 113: 631-642; Nichols et al., *Cell*, 1998, 95: 379-391). Differentiation of the ICM to extraembryonic tissues is governed by Cdx2 and Gata6, transcription factors that repress pluripotency while inducing genes of the trophectoderm and extraembryonic endoderm, respectively (Jedrusik et al., *Genes Dev.*, 2008, 22: 2692-2706; Koutsourakis et al., *Development*, 1999, 126: 723-732; Niwa et al., *Cell*, 2005, 123: 917-929). After the formation of extraembryonic tissues, the pluripotent epiblasts are converted to three germ layers during gastrulation, but how these processes are regulated remains unknown.

One of the best-studied processes during gastrulation, pNSC specification, is at the center of developmental biology. Studies in lower vertebrates, including frogs and chicks, indicate that many transcription factors are involved in pNSC specification, including zinc finger proteins, Sox family, Otx family, and helix-loop-helix transcription factors (Mizuseki et al., *Development*, 1998, 125: 579-587; Nakata et al., *Proc. Natl. Acad. Sci. USA*, 1997, 94: 11980-11985; Rex et al., *Dev. Biol.*, 1997, 271: 439-466; Sheng et al., *Cell*, 2003, 115: 603-613). To date, it is unclear which transcription factor is responsible for the conversion from pluripotent cells to pNSC in mammals. The most promising factor is Sox1, because its expression pattern parallels pNSC formation in mouse (Bylund et al., *Nat. Neurosci.*, 2003, 6: 1162-1168; Pevny et al., *Development*, 1998, 125: 1967-1978). However, Sox1-knockout mice do not exhibit severe brain deficits, probably because of compensation by other Sox members (Nishiguchi et al., *Genes Dev.*, 1998, 12: 776-781). Similarly, the transcriptional determinant for human pNSC specification is unknown. The failure in identifying mammalian transcriptional determinants underlying pNSC specification is at least partly due to the lack of model systems that permit easy genetic manipulation and direct observation of developmental processes. Embryonic stem cells (ESCs), derived from the ICM or epiblast, differentiate to cells/tissues of the three germ layers according to developmental principles (Murry and Keller, *Cell*, 2008, 132: 661-680; Stern, *Development*, 2005, 132: 2007-2021; Zhang, *Brain Pathol.*, 2006, 16: 132-142). When human ESCs (hESCs) are differentiated toward the neural fate under a chemically defined medium in the absence of growth factors, pNSCs appear around day 6-8 and form neural tube-like rosettes at day 14 with corresponding gene expression patterns (Li et al., *Nat. Biotechnol.*, 2005, 23: 215-221; Pankratz et al., *Stem Cells*, 2007, 25: 1511-1520; Zhang et al., *Nat. Biotechnol.*, 2001, 19: 1129-1133; Zhang and Zhang, *Methods Mol. Biol.*, 2010, 584: 355-366). This differentiation process resembles in vivo development of the neural plate and neural tube, and it therefore represents a useful tool for studying the molecular underpinnings of human pNSC specification (Zhang, *Brain Pathol.*, 2006, 16: 132-142).

During hESC neural differentiation, the pNSCs do not express Sox1, the earliest marker of pNSC in mouse embryos or in pNSC differentiated from mouse ESCs (mESCs) (Li et al., *Nat. Biotechnol.*, 2005, 23: 215-221; Pankratz et al., *Stem Cells*, 2007, 25: 1511-1520; Pevny et al., *Development*, 1998, 125: 1967-1978; Suter et al., *Stem Cells*, 2008, 27: 49-58; Ying et al., *Nat. Biotechnol.*, 2003, 21: 183-186). Instead, Pax6, a paired box (Pax) transcription factor expressed in region-specific neural progenitors after neural tube closure in mouse (Schmahl et al., *Acta Neuropathol.*, 1993, 86: 126-135; Walther and Gruss, *Development*, 1991, 113: 1435-1449), is uniformly expressed in hESC-derived pNSCs (Li et al., *Nat. Biotechnol.*, 2005, 23: 215-221; Pankratz et al., *Stem Cells*, 2007, 25: 1511-1520). These observations raise an intriguing possibility that Pax6 may play a novel role in human pNSC specification. Three isoforms of Pax6 have been identified. The canonical Pax6a harbors two DNA binding domains, the paired domain (PD) and homeodomain (HD), and a prolineserine-threonine (PST)-rich transactivation domain. Pax6b is a spliced variant of Pax6, which is produced by insertion of 14 amino acids (exon5a) into the PD, thus conferring different DNA binding specificity (Epstein et al., *Genes Dev.*, 1994, 8: 2022-2034; Kozmik et al., *EMBO J.*, 1997, 16: 6793-6803; Walther and Gruss, *Development*, 1991, 113: 1435-1449). The third isoform of Pax6 (Pax6ΔPD) lacks the paired domain. Both Pax6a and Pax6b are expressed in the brain, whereas Pax6ΔPD is identified only in eye and olfactory bulb (Kim and Lauderdale, *Dev. Biol.*, 2006, 292: 486-505). In rodents, Pax6 is essential for the development of several organ systems, including eye, pancreas, and cerebrum (Chi and Epstein, *Trends Genet.*, 2002, 18: 41-47).

Results

Pax6 is Uniformly Expressed in Early Human, but not Mouse, pNSCs.

During mouse development, Pax6 is first detected in neural progenitors of the developing forebrain at E8.5-E9.5, 1 day after the formation of Sox1-expressing neuroectoderm (NE) cells within the neural plate/tube (Bylund et al., *Nat. Neurosci.*, 2003, 6: 1162-1168; Pevny et al., *Development*, 1998, 125: 1967-1978; Walther and Gruss, *Development*, 1991, 113: 1435-1449). However, NE cells differentiated from various hESC lines (H1, H9, H13, HSF1, HSF6) and induced pluripotent stem cells (iPSCs) under different conditions uniformly express Pax6 while Sox1 are still negative (Gerrard et al., *Stem Cells*, 2005, 23: 1234-1241; Hu et al., *Proc. Natl. Acad. Sci. USA*, 2010, 107: 4335-4340; Li et al., *Nat. Biotechnol.*, 2005, 23: 215-221; Pankratz et al., *Stem Cells*, 2007, 25: 1511-1520; Wu et al., *Proc. Natl. Acad. Sci. USA*, 2010, 107: 5254-5259; Yao et al., *Proc. Natl. Acad. Sci. USA*, 2006, 103: 6907-6912). Importantly, the Pax6-expressing NE cells can be readily patterned to region-specific, Sox1-expressing neural progenitors, which will give rise to various neuronal subtypes, including dorsal and ventral forebrain, midbrain, spinal cord, and retinal cells (Li et al., *Nat. Biotechnol.*, 2005, 23: 215-221, Li et al., *Development*, 2009, 136: 4055-4063; Meyer et al., *Proc. Natl. Acad. Sci. USA*, 2009, 106: 16698-16703; Pankratz et al., *Stem Cells*, 2007, 25: 1511-1520; Yan et al., *Stem Cells*, 2005, 23: 781-790; Zhang et al., *Nat. Biotechnol.*, 2001, 19: 1129-1133). This suggests that the early Pax6-expressing human NE cells represent a primitive state, i.e., the early Pax6-expressing human NE cells are pNSCs.

Figure 1:
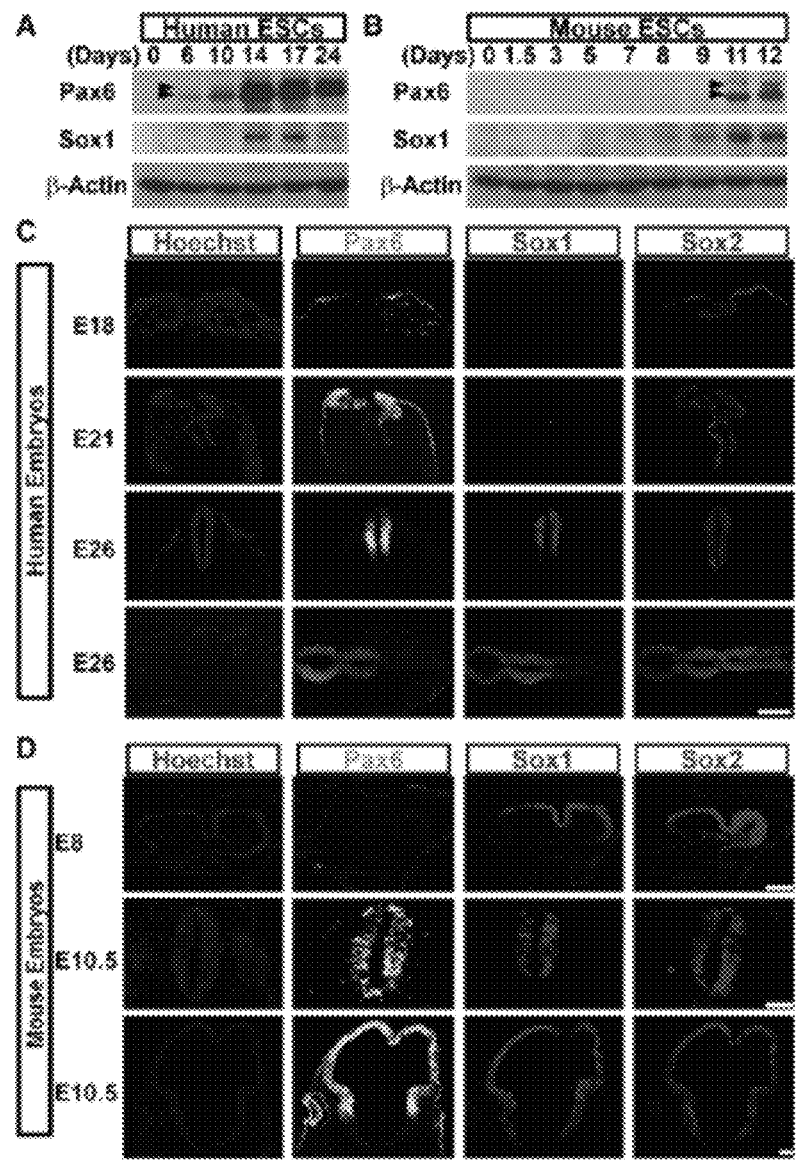
FIG. 1A-D show expression of neural transcription factors in fetuses and along ESC differentiation.
Figure 2:
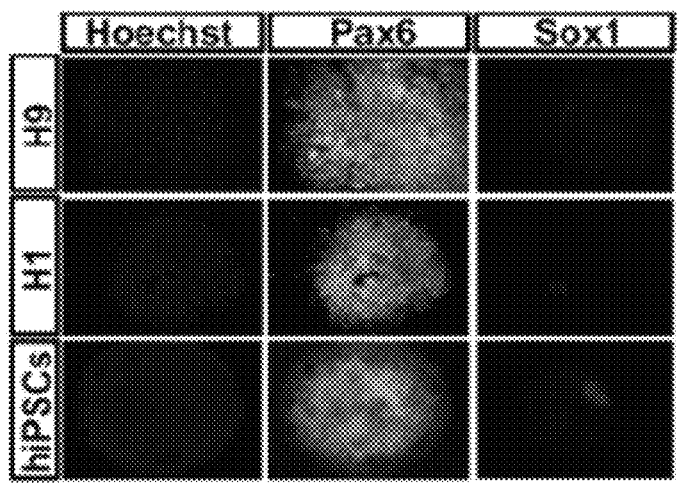
FIG. 2 demonstrates that hESCs and iPSCs use identical mechanisms for neural specification. H9 hESCs, H1 hESCs and human iPSCs are differentiated to pNSCs cells for 8 days, which are Pax6+/Sox1−. This demonstrated that hESCs and human iPSCs employ identical transcriptional networks for pNSCs specification and Pax6 represents an efficient way to convert human iPSCs to pNSCs, given their lower differentiation potential as compared to hESCs (Hu et al., *Proc Natl Acad Sci USA*, 2010, 107: 4335-4340).

We thus hypothesized that Pax6 may play a unique role in NE specification besides regional patterning in human. Western blotting analysis revealed that Pax6 was detectable six days after hESC differentiation, whereas Sox1 started to be detected around day 14 (FIG. 1A). This was confirmed by immunostaining, showing that Pax6, but not Sox1, was expressed in pNSCs at day 8 of differentiation from the H1 and H9 hESC lines as well as a human iPSC line (FIG. 2). In contrast, Pax6 was not detected until 2-3 days after Sox1 expression during mouse ESC neural differentiation (FIG. 1B), consistent with previous reports (Bylund et al., *Nat. Neurosci.*, 2003, 6: 1162-1168; Suter et al., *Stem Cells*, 2008, 27: 49-58). It is also noteworthy that both Pax6a and Pax6b, but not Pax6ΔPD, were expressed in human pNSCs, as confirmed by an antibody recognizing the C-terminus of Pax6 (shown in Figures S1B-S1D in Zhang et al. 2010, which is incorporated by reference; Kim and Lauderdale, *Dev. Biol.*, 2006, 292: 486-505).

Figure 3:
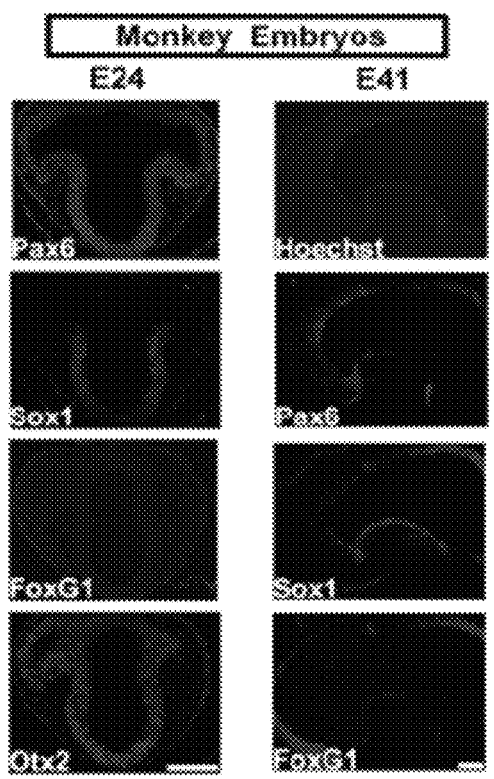
FIG. 3 shows expressions of Otx2, Pax6, Sox1 and FoxG1 in early monkey embryos. Similar to that of humans, rhesus monkey pNSCs are also Pax6+/Sox1− and Sox1 is only expressed in regional NSCs. This suggests that the transcriptional networks along pNSC specification are conserved within primates.

Validation analysis in human fetal tissues (shown in Figure S1E in Zhang et al. 2010, which is incorporated by reference) revealed that at E18 (Carnegie stage 8-9), when the neural plate begins to form, Pax6, but not Sox1, was detected in the single-layered NE cells that were also Sox2 positive (FIG. 1C). This expression pattern was retained at E21 (Carnegie stage 10), in which the neural plate becomes pseudo-multiple layered. By the time that forebrain and midbrain have already been clearly demarcated at E26 (Carnegie stage 11-12), Pax6 was now restricted to the forebrain and part of the spinal cord but absent in the midbrain whereas both Sox1 and Sox2 were expressed in all NE cells (FIG. 1C). Our previous study showed that pNSCs differentiated from rhesus monkey ESCs also exhibited Pax6 expression (Pankratz et al., *Stem Cells*, 2007, 25: 1511-1520). Consistent with the in vitro observations, pNSCs of rhesus monkey fetuses uniformly expressed Pax6, but not Sox1 (FIG. 3).

In contrast to primates, Sox1 and Sox2 were highly expressed in the mouse neural plate at E8 whereas Pax6 was not expressed (FIG. 1D). At E10.5, Pax6 was expressed in the dorsal forebrain and spinal cord, but not in the midbrain, whereas Sox1 and Sox2 were ubiquitously expressed in all NE cells (FIG. 1D).

Thus, Pax6 is expressed by human pNSCs but not mouse pNSCs, suggesting a potential distinct role of Pax6 in human NE specification.

Pax6 is Required for NE Specification from hESCs.

Figure 7:
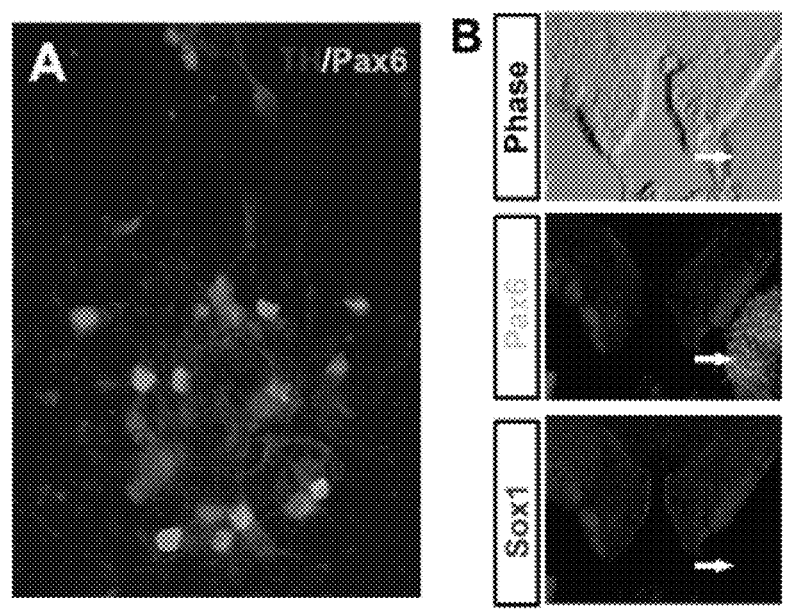
FIG. 7A-B shows that Pax6 expressing pNSCs within transplants are origins of tumor formation.

We then built ESC lines that constitutively express RNAi for Pax6 (targeting the homeodomain sequence and thus all three isoforms) or luciferase (Luc, as a control) through lentiviral infection (shown in Figure S2A in Zhang et al. 2010, which is incorporated by reference), and the knockdown efficacy was confirmed by western blotting (shown in FIG. 2A in Zhang et al. 2010, which is incorporated by reference) and RT-PCR (shown in FIGS. 7A and 7B in Zhang et al. 2010, which is incorporated by reference).

After ten days of neural differentiation under our chemically defined conditions, hESC-derived pNSCs with Luc RNAi presented typical columnar pNSC morphology and organized into early rosettes (Pankratz et al., *Stem Cells*, 2007, 25: 1511-1520; Zhang et al., *Nat. Biotechnol.*, 2001, 19: 1129-1133). Noticeably, differentiating hESCs with Pax6 RNAi remained as round aggregates formed by round cells but not migrating columnar cells (shown in FIG. 2C in Zhang et al. 2010, which is incorporated by reference). Consistent results were obtained with different lines (with or without GFP) and different batches of differentiation, indicating that the knockdown phenotype was not due to asynchronized differentiation or different viral integration.

The lack of columnar pNSCs after Pax6 knockdown indicates failure of NE differentiation. Microarray analyses, by means of mRNA pooled from different transgenic lines, showed that about 500 genes were up- or down-regulated more than 5-fold in the Luc RNAi control line after 6 days of differentiation (shown in FIG. 2D in Zhang et al. 2010, which is incorporated by reference). Consistent with our previous report (Pankratz et al., Stem Cells, 2007, 25: 1511-1520), the down-regulated genes were related to ESC/epiblast (e.g., Oct4, Nanog, and Myc) and the up-regulated genes (Lhx2, Six3, Six6, Lmo3, Meis2, N-cadherin, FGF8, FGF9, Delta like 1 homolog, and Wnt5b) were associated with the early NE (summarized in Tables S1 and S2 in Zhang et al. 2010, which is incorporated by reference). In contrast, fewer genes were up- or down-regulated in the Pax6 knockdown cells no matter what threshold (fold change) was set (shown in FIG. 2D in Zhang et al. 2010, which is incorporated by reference). The 50 most up- and down-regulated genes during differentiation of the control ESCs were less changed in the Pax6 knockdown lines (shown in FIG. 2E in Zhang et al. 2010, which is incorporated by reference), which were confirmed by qRT-PCR (shown in FIG. 7B in Zhang et al., 2010). Thus, cells with Pax6 knockdown largely retained pluripotent gene expression and had much less NE gene expression. Cell cycle analyses revealed no differential cell death or proliferation after Pax6 knockdown (shown in Figures S6A-S6C in Zhang et al., 2010). Therefore, Pax6 knockdown prevents hESCs from differentiation, thus trapping them in the pluripotent state.

After another 1-2 weeks of differentiation, NE cells from the Luc RNAi group readily formed NE aggregates and generated βIII-tubulin-positive neurons. In contrast, cells with Pax6 knockdown under the same conditions rarely formed NE spheres and they failed to differentiate into neurons in adherent culture (shown in FIGS. 2B and 2C in Zhang et al., 2010). These data also suggest that cells derived from Pax6 RNAi lines are not properly developed to the NE stage.

To exclude the possibility that the requirement of Pax6 in NE specification was due to our differentiation protocol, we adopted a new neural differentiation protocol through dual SMAD signaling inhibition (Chambers et al., Nat. Biotechnol., 2009, 27: 275-280). Again, knockdown of Pax6 severely blocked pluripotent gene down-regulation and NE gene up-regulation even with the addition of BMP inhibitors (shown in Figure S2B in Zhang et al., 2010).

To further exclude the possibility of cell culture artifact, undifferentiated hESCs were injected subcutaneously into severe combined immunodeficient (SCID) mice to produce teratomas, an in vivo system allowing ESC to differentiate into multi-lineages including neural tissues. Teratoma generation efficiency and size were comparable in both control and Pax6 knockdown groups. NE rosettes, revealed by hematoxylin and eosin (H&E) staining and confirmed by immunostaining for Sox1 and Sox2, were frequently observed in teratomas formed by hESCs with Luc RNAi but rarely in the Pax6 RNAi group (shown in FIGS. 3A and 3B in Zhang et al., 2010). Nevertheless, mesoderm (cartilage) and endoderm (gut epithelium) derivatives were observed in both Luc and Pax6 knockdown tumors (shown in FIG. 3A in Zhang et al., 2010). Western blotting analyses of individual teratomas validated that the levels of neural transcription factors Sox1 and Sox2 drastically decreased in the Pax6 knockdown tumors, whereas the endodermal marker, alpha-fetoprotein (AFP), and epidermal marker, cytokeratin, were expressed at similar levels in both groups (shown in FIG. 3C in Zhang et al., 2010). These data indicate that the requirement of Pax6 for human NE specification is not a culture artifact and Pax6 is probably a potential downstream factor of extracellular neural inducers during human NE specification.

Pax6 is Not Required for Mouse NE Specification.

The opposite temporal expression pattern of Pax6 and Sox1 in human versus mouse suggests a differential role of Pax6 in NE specification in these two species. To test this hypothesis, we infected the D3 and Sox1/GFP reporter (Ying et al., Nat. Biotechnol., 2003, 21: 183-186) mESCs with Pax6 or Luc RNAi lentiviruses (the RNAi targeting sequence is identical between human and mouse) and confirmed the knockdown efficiency by western blotting (shown in Figure S2E in Zhang et al., 2010). Differentiation to Sox1-expressing mouse NE cells, indicated by GFP, was readily observable at day 6 and reached a peak at day 9-10, consistent with western blotting analyses (FIG. 1B). However, knockdown of Pax6 did not affect the Sox1 level as evaluated by fluorescent microscopy or FACS, suggesting that Pax6 is not necessary for mouse NE specification (shown in Figures S2C and S2D in Zhang et al., 2010). Western blotting with the naive mESCs (D3 line) confirmed that neither Pax6 nor Luc RNAi altered the expression of Sox1 (shown in Figure S2E in Zhang et al., 2010). The Pax6 RNAi-expressing mouse NE cells further differentiated to neurons with similar efficiency as the Luc RNAi control (shown in Figure S2F in Zhang et al., 2010).

The side-by-side comparison of Pax6 RNAi effects on human versus mouse ESC neural differentiation strongly suggests that Pax6 is a crucial transcription factor for NE specification in human, but not mouse.

Overexpression of Pax6 in hESCs Down-Regulates Pluripotent Gene Expression.

Figure 4:
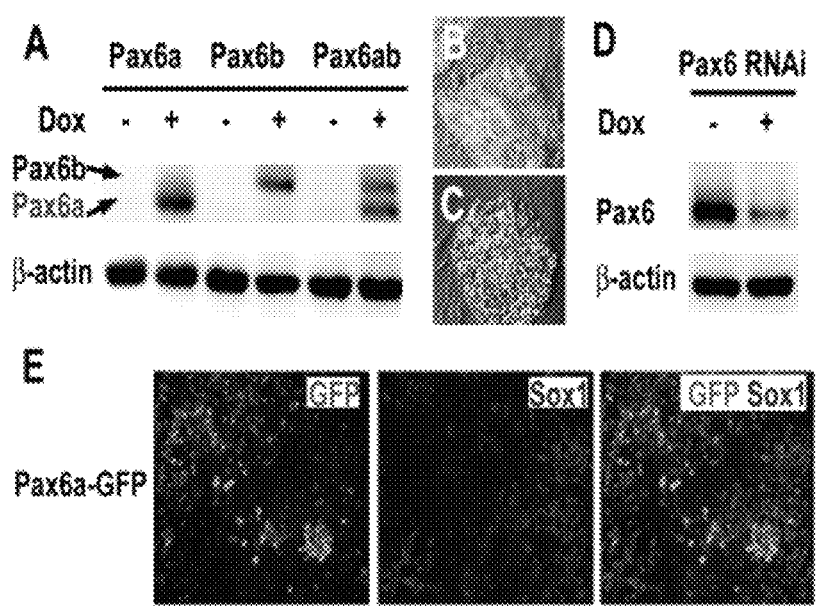
FIGS. 4A-E demonstrate with transgenic hESC lines that Pax6 overexpression maintains cells in pNSC state.

We next expressed Pax6a and Pax6b (with GFP fusion to the C terminus) in hESCs under the elongation factor (EF) 1α promoter through lentiviral infection (see Figure S1B in Zhang et al., 2010 for diagrams demonstrating the constructs). GFP expression was visible 30-40 hr after viral infection in both GFP- and Pax6-GFP-overexpressing cells with the highest GFP expression at day 4-5. Three days after infection, forced expression of GFP alone had no effect on Oct4 or Nanog expression, whereas overexpression of either Pax6a-GFP or Pax6b-GFP resulted in loss of Oct4 and Nanog expression even under the culture conditions that favored ESC maintenance (see FIGS. 4A and 4B in Zhang et al., 2010 for examples).

Pax6 is a transcription factor with three key functional domains. The paired domain (PD) and homeodomain (HD) are for DNA binding and the P/S/T-rich transactivation domain (PST) holds the transcriptional activity. Within the paired domain, there also includes two sub-domains, the PAI and RED domains. It is reasonable to hypothesize that Pax6 employ different DNA binding domains for different target gene promoter occupancy and the PST domain regulates the transcriptional activity of those genes. Through this, Pax6 can thus fulfill its various physiological functions, such as brain, eye and pancreas development.

Except for the HD, all of the major parts of the Pax6 molecule, including the paired domain and the PST domain, are required for the effect of Pax6 on hESC differentiation. Specifically, overexpression of Pax6ΔPD (FIG. 18) did not affect Oct4 or Nanog expression, indicating the requirement of the paired domain in down-regulating pluripotent genes. Further experiments with Pax6 mutants indicated that deletion of the N-terminal PAI domain (FIG. 16) or the PST transactivation domain (FIG. 20), but not the HD of Pax6 (FIG. 14), abrogated the effect of Pax6 in repressing Oct4 and Nanog. See Figure S3 in Zhang et al., 2010 for examples.

Overexpression of Pax6a but not Pax6b Directs hESCs to NE.

Although both Pax6a and Pax6b down-regulated pluripotent genes, it was not known whether the two Pax6 isoforms acted similarly on NE specification. By monitoring the hESC cultures daily, we discovered that, unlike the GFP control cells, the initially scattered Pax6a-GFP cells gradually aggregated in the hESC colonies (see FIG. 4C in Zhang et al., 2010 for demonstrations). Similar aggregation was observed in Pax6aΔHD mutant (see Figure S3 in Zhang et al., 2010 for demonstrations). Eight days after lentiviral infection, Pax6a-positive cells exhibited an elongated columnar morphology and formed rosettes (see FIG. 4D in Zhang et al., 2010 for demonstrations), indicative of their neural identity. Interestingly, the inventors found that Pax6b-GFP-expressing cells migrated to the edge of the hESC colonies and eventually became large flat cells, giving a membranous appearance outside of the hESC colonies (see FIGS. 4C and 4D in Zhang et al., 2010 for demonstrations). By fluorescent microscopy, the inventors noticed kidney-like or horseshoe-shape large nuclei with two or more lobes in most Pax6b-GFP-positive cells (see FIG. 4D in Zhang et al., 2010 for demonstrations). The migration property, cell morphology, and multiploid nuclei suggest that the Pax6b-expressing cells have adopted a trophoblast-like fate.

Figure 5:
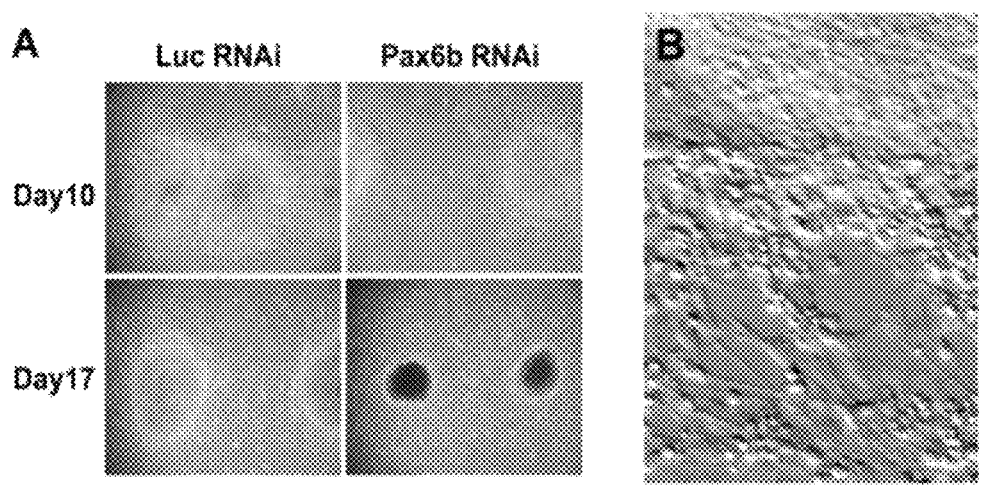
FIG. 5A-B shows that downregulation of Pax6 in NSCs causes cell death and terminal differentiation.

Although forced expression of Pax6a down-regulated Oct4 and Nanog quickly, expression of another pluripotent factor, Sox2 (also a NE transcription factor), was retained (see FIG. 5A in Zhang et al., 2010 for demonstrations). The Pax6a-overexpressing cells also expressed fatty acid binding protein 7 (Fabp7) and N-cadherin (see FIGS. 5B and 5C in Zhang et al., 2010 for demonstrations), which are specifically expressed in NE cells. It should be noted that N-cadherin was distributed evenly on the membrane of the Pax6a-expressing cells. It is known that the pNSCs express N-cadherin evenly on the cell membrane whereas regional neural progenitors that express Sox1 and are polarized express N-cadherin on the lumen side (Pankratz et al., *Stem Cells*, 2007, 25: 1511-1520). Hence, the specific expression pattern of N-cadherin in Pax6a-overexpressing cells indicates their pNSC state, which coincides with our finding that most Pax6a-positive cells were negative for Sox1. Occasionally, Sox1 was found in the Pax6a-positive cells. Interestingly, the Sox1-expressing cells always had lower Pax6a expression (see FIG. 5D in Zhang et al., 2010 for demonstrations).

In contrast to Pax6a, Pax6b-overexpressing cells showed no expression of any neural marker tested, confirming their nonneural identity. Furthermore, both Pax6a and Pax6b cells lacked expression of Brachyury and AFP, mesodermal and endodermal markers, respectively, or Gata6, an extraembryonic endodermal maker (data not shown).

Thus, although both Pax6a and Pax6b triggered hESC differentiation through down-regulation of pluripotent genes, only Pax6a directed the cells to a neural fate.

In contrast to the results seen with hESCs, overexpression of either Pax6a or Pax6b in mESCs neither changed the ESC morphology nor induced the formation of early rosettes. Overexpression of Pax6a or Pax6b in mESCs did not decrease Oct4 expression and the mESCs could be passaged continuously as normal ESCs (see Figures S4A and S4B in Zhang et al., 2010 for demonstrations). Therefore, the prominent ESC-differentiation and neural-inducing effects of Pax6 are unique to human ESCs.

Pax6a but not Pax6b Induces NE Gene Expression.

Expression of either Pax6a or Pax6b differentiates hESCs rapidly and this prevented us from establishing stable transgenic lines for biochemical studies. We therefore built inducible Pax6a, Pax6a-GFP, Pax6b-GFP, and GFP clonal hESC lines by using a lentivirus-based inducible system (Xia et al., *Stem Cells,* 2008, 26: 525-533). Doxycycline treatment or induction of GFP expression did not alter the morphology and growth of hESCs. In contrast, induction of Pax6a-GFP expression in hESCs for 3-4 days trigged neural rosette formation in the ESC colony. We again found that Pax6b-GFP-overexpressing cells tended to localize in the periphery of the colony and they possessed the same kidney-like or horseshoe-shape nuclei as seen previously (data not shown). These results confirmed the observations made with constitutive Pax6-expressing cells that Pax6a, but not Pax6b, promotes pNSC specification.

Figure 6:
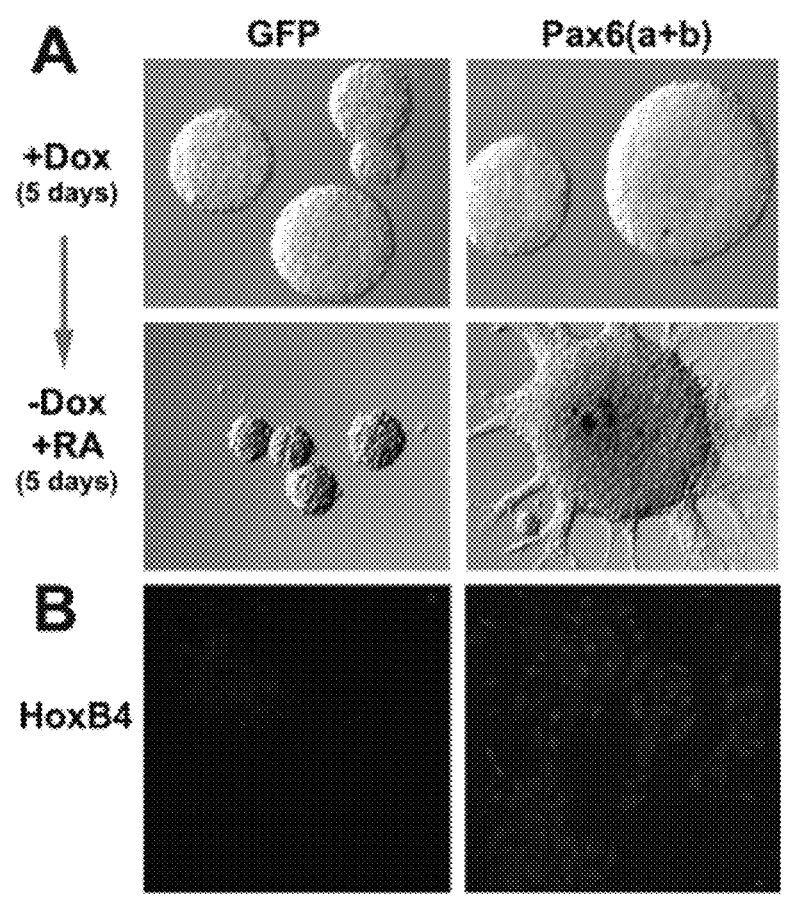
FIG. 6A-B shows that overexpression of Pax6 reprograms regional NSCs to pNSCs.

To examine the dynamics of Pax6 effects, we performed qRT-PCR analyses after Pax6 was induced for 1, 3, or 5 days in ESC culture conditions. Consistent with microarray data (see FIG. 2E and Table S1 in Zhang et al., 2010, for demonstrations), neural differentiation of normal hESCs was accompanied by up-regulation of neural transcription factors including Lhx2, Six3, Six6, Lmo3, and Meis2 as well as neural-related signaling molecules, such as Fabp7, Lix1, Dlk1, Dach1, and N-cadherin at days 6 and 10 (see FIG. 6A in Zhang et al., 2010, for demonstrations). Induction of GFP expression did not alter the gene expression pattern in hESCs. Pax6a or Pax6a-GFP expression greatly induced those neural genes within 1-3 days, but not genes of extraembryonic lineages, mesoderm, endoderm, or epidermal tissues (see FIG. 6B in Zhang et al., 2010, for demonstrations). These results suggest that Pax6a induces neural gene expression and the fusion of GFP to Pax6 does not interfere with its function.

In animal studies, Pax6 is important for eye and pancreas development and brain patterning. RT-PCR analysis indicated that retinal (Crx, Chx10, and RPE65), mesoendodermal (Brachyury), and pancreatic (Sox17, Hnf1b, and Pdx1) genes or regional patterning genes (FoxG1, En1, Hoxb4, and Nkx2.1) were not induced by Pax6a (see Figures S5A-S5C in Zhang et al., 2010, for demonstrations), further supporting the pNSC specification effect of Pax6a. In contrast, overexpression of Pax6b-GFP did not induce NE gene expression or characteristic genes from other germ layers except Cdx2 (see FIG. 6B in Zhang et al., 2010, for demonstrations), a key factor for trophectoderm development. In this case, Cdx2 was not increased until 5 days after induction of Pax6b.

It is noteworthy that the pNSC-inducing effect of Pax6a is quick and robust. Even in the presence of Activin A and Bio (a GSK3β inhibitor), a condition that favors mesoendoderm differentiation (Kroon et al., *Nat. Biotechnol.,* 2008, 26: 443-452), Pax6a overexpression induced neural rosette formation within hESC colonies with concomitant elevated expression of NE genes and repressed mesoendodermal transcripts (see Figures S5D-S5F in Zhang et al., 2010, for demonstrations). These data suggest that Pax6 is an intrinsic regulator of human pNSC specification.

Pax6a and Pax6b Coordinate with Each Other to Specify the NE Fate.

Because both Pax6a and Pax6b were expressed during hESC NE differentiation (FIG. 1A) but overexpression of Pax6a alone was sufficient to convert hESCs to pNSC, we asked whether Pax6b was needed for pNSC specification. We selected one RNAi sequence targeting exon5a that can specifically knock down Pax6b (see FIG. 7A and Figure S2A in Zhang et al., 2010, for demonstrations). qRT-PCR showed that similar to knock down of both isoforms, specific knockdown of Pax6b reduced pluripotent gene down-regulation and neural gene up-regulation during normal NE differentiation, although at a modest level (see FIG. 7B in Zhang et al., 2010, for demonstrations). These results suggest that Pax6b is also required for human pNSC specification. Because overexpression of Pax6b cannot induce neural genes, this result suggests that the way Pax6b functions in human pNSC specification is through coordinating with Pax6a in down-regulation of pluripotent genes, which is a prerequisite for subsequent up-regulation of neural genes. In addition, the neural blocking effect was reproduced with two Pax6 RNAi constructs, ensuring that the phenotype was due to knock down of Pax6, but not off-target effects.

We then asked whether Pax6 can regulate lineage genes directly. Pax6a-GFP, Pax6b-GFP, and GFP lines were induced with doxycycline for 1 and 3 days, and chromatin immunoprecipitation (ChIP) analysis was performed to examine the binding of Pax6 to promoters of lineage-specific genes. GFP protein did not show any binding to the pluripotent genes or neural genes (data not shown). Both Pax6a and Pax6b were found to localize to the Oct4 and Nanog promoters (see FIG. 7C in Zhang et al., 2010 for demonstrations). Pax6 bound to the Nanog promoter one day after Pax6 was induced, earlier than it bound to the Oct4 promoter. This is consistent with the observation that Nanog was down-regulated earlier than Oct4 in normally differentiated cells. As expected, only Pax6a bound to the promoters of neural genes that were up-regulated after Pax6a expression, mostly at day three. In summary, both Pax6a and Pax6b bound to the promoters of pluripotent genes, corresponding to the downregulation of Oct4 and Nanog. Pax6a, but not Pax6b, occupied the promoters of neural genes, coinciding with the NE fate mediated by Pax6a.

Pax6 Overexpression Maintains Cells in pNSC State and Blocking Pax6 Expression in NSCs Leads to Cell Death pr Differentiation into Neurons.

Maintaining of NSCs in a primitive state can be achieved by Pax6 overexpression and driving the cells out of the primitive state can also be achieved by shutting off Pax6 expression. As demonstrated by transgenic hESC lines in FIG. 4, after differentiation to pNSCs at day 10, induction and maintenance of Pax6 by doxycycline treatment for two weeks kept growth factor-independent proliferation and suppressed Sox1 expression. Three days after Dox removal, many cells began to express Sox1. In addition, the inducible transgenic overexpression/knockdown tool represents a useful strategy to control the cell fates.

It is noteworthy that Pax6b is also required for maintaining pNSCs. In forebrain dorsal NSCs, low level of Pax6 is also expressed together with Sox1. When we differentiate hESCs toward a neural fate, they will be faulted to a forebrain dorsal identity (Li et al., *Development*, 2009, 136: 4055-4063). However, if Pax6b is knocked down as demonstrated by Pax6b RNAi hESC lines, these NSCs cannot be maintained in a primitive state and they terminally differentiate to certain migrating flat cells and neurons with some dead cells starting to detach from the culture surface (FIG. 5A). In another experiment where day 14 NSCs were transiently infected with Pax6 RNAi lentiviruses (targeting both Pax6a and Pax6b), we also found massive cell death and neuronal differentiation 3-4 days after virus infection (FIG. 5B). These data demonstrate that Pax6 (probably both a and b isoforms) is crucial for maintaining NSCs. Downregulation of Pax6 will thus drive NSCs to leave the primitive stage, and then drive neural progenitors to differentiate to neurons.

Discussion

Since the groundbreaking work by Spemann and Mangold, signaling pathways that lead to NE induction, including BMP inhibition and FGF activation, are now well established (Levine and Brivanlou, *Dev. Biol.*, 2007, 308: 247-256; Munoz-Sanjuán and Brivanlou, *Nat. Rev. Neurosci.*, 2002, 3: 271-280; Stern, *Development*, 2005, 132: 2007-2021, Stern, *Curr. Opin. Cell Biol.*, 2006, 18: 692-697). However, transcriptional networks that control NE specification are not well defined. Our present study provides evidence that Pax6 is both necessary and sufficient for pNSC specification from human but not mouse ESCs. This finding raises a question of how such a well-conserved protein acquired the novel function in human brain development over evolution. Furthermore, we discovered that the neural inductive function of Pax6 is achieved by its repression of pluripotent genes and activation of NE genes. Taken together with the unique differential effects of Pax6a and Pax6b, we propose that specification of epiblast or ESCs to an embryonic germ layer depends upon induction of the target germ layer genes and repression of pluripotent genes and possibly also genes of other germ layers (see FIG. 7D in Zhang et al., 2010 for demonstrations). This proposition opens the possibility for the existence of a determinant gene(s) for mesoderm and endoderm.

Pax6 is Necessary and Sufficient for Human pNSC Specification.

In this study, we have demonstrated that overexpression of Pax6, either constitutively or conditionally, converts hESCs to pNSCs, even under conditions that favor hESC maintenance or mesoendoderm differentiation. The pNSC identity was verified by the characteristic columnar cells that organize into early rosettes, loss of pluripotent gene expression, upregulation of NE genes, and lack of other germ layer markers. Knockdown of Pax6 blocks pNSC specification from hESCs not only in the teratoma assay, which allows spontaneous three-germ-layer differentiation in vivo, but also in our chemically defined NE differentiation system and a newly developed dual SMAD inhibition culture, both of which strongly promote hESC neural differentiation. These results, gathered from both gain of function and loss of function of Pax6 under opposing conditions, strongly indicate that Pax6 is an intrinsic determinant for the human pNSC fate. The fact that overexpression of Pax6 does not induce mesoendoderm and that knockdown of Pax6 does not inhibit mesoendodermal lineage differentiation excludes the possibility that Pax6 first promotes mesoendodermal differentiation which in turn induces neural differentiation. This is further supported by the result that dual SMAD inhibition by Noggin and SB431542 does not rescue the neural blocking effect when Pax6 is knocked down. Therefore, Pax6 is most probably a crucial downstream effector of neural inducers, such as BMP inhibitors.

Pax6-Mediated pNSC Specification Depends on Both Repression of Pluripotent Genes and Induction of NE Genes.

It is quite remarkable that a single transcription factor, Pax6, can act as a switch from proliferating hESCs to differentiating pNSCs. This is a direct cell fate conversion rather than an indirect process through promoting cell proliferation or survival of existing pNSCs in the hESCs (Schroeder, *Nature*, 2008, 453: 345-351). First, hESCs, maintained under standard culture conditions, do not express Pax6, an early marker of human pNSCs now widely used. Second, overexpression or knockdown of Pax6 does not alter cell proliferation or survival (see Figure S6 in Zhang et al., 2010 for demonstrations). Third, time-lapse tracking reveals that once Pax6 is turned on, the cells become columnar pNSCs, migrate, and aggregate to form early rosettes (see Movies S1 and S2 in Zhang et al., 2010 for examples). Furthermore, at the molecular level, Pax6 binds to pluripotent genes and NE genes directly.

Removal of either the PAI domain, the whole PD or PST domain, all abrogates the function of Pax6 to differentiate hESCs to pNSC. However, the HD is not required for Pax6 induced pNSC specification, as deleting of this HD domain does not affect stem cell genes downregulation and pNSC generation. The same phenomenon has also been observed in a zebrafish study, which shows the HD is dispensable for Pax6 mediated pancreatic endocrine cell differentiation (Verbruggen et al., *J Biol Chem*, 2010, 285: 13863-13873). In addition, it has been reported widely about a large number of Pax6 mutations, which caused aniridia and brain dysfunctions in humans. Furthermore, biochemistry analysis also demonstrates that phosphorylation/dephosphorylation of certain S/T amino acids can regulate Pax6 transcriptional activity (Yan et al., *J Biol Chem*, 2007, 282: 13954-13965; Kim et al., *J Biol Chem*, 2006, 281: 7489-7497; Mikkola et al., *J Biol Chem*, 1999, 274: 15115-15126). These suggest that regulation of kinases/phosphatases of Pax6, mutating certain key residues of Pax6 or deleting certain Pax6 protein domains can be efficiently used to increase/decrease Pax6 transcriptional activity, stability and its physiological function. And these strategies can also be used for generation, maintaining, reprogramming of pNSCs and controlling brain tumors.

Both Pax6a and Pax6b bind to promoters of pluripotent genes, including Oct4 and Nanog, and repress their expression whereas only Pax6a binds to NE gene promoters and activates NE genes. Therefore, the pNSC fate-determining role of Pax6 is achieved through coordination of Pax6a and Pax6b in preventing hESC self-renewal, thus initiating their differentiation and inducing the cells toward the pNSC fate by Pax6a. Suppression of pluripotent factors alone is not sufficient for differentiating ESC/epiblast to pNSCs. This is demonstrated by the fact that overexpression of Pax6b, which does not possess neural-inducing activity, drives hESCs out of the stem cell state but these cells turn into trophoblast. This phenomenon is reminiscent of the extraembryonic outcome of ESCs with knockdown of Oct4, Nanog, or Sox2 (Chew et al., *Mol. Cell. Biol.*, 2005, 25: 6031-6046; Fong et al., *Stem Cells*, 2008, 26: 1931-1938; Hay et al., *Stem Cells*, 2004, 22: 225-235; Hyslop et al., *Stem Cells*, 2005, 23: 1035-1043; Matin et al., *Stem Cells*, 2004, 22: 659-668; Zaehres et al., *Stem Cells*, 2005, 23: 299-305). Thus, repression of pluripotent genes initiates the differentiation process but it alone is not sufficient for embryonic germ layer differentiation. Pax6a is probably the key inductive signal for the pNSC fate. Indeed, Pax6a binds to a set of downstream neural genes, which corresponds to the neural phenotypes. Pax6b, though by itself not a direct neural inducer, potentiates the neural inductive effect of Pax6a through collaboration with Pax6a for sufficient repression of pluripotent genes, which is a prerequisite for induction of neural genes (see FIG. 7D in Zhang et al., 2010 for demonstrations).

The pNSC Specification Role of Pax6 is Unique to Primates.

The Pax6 protein is highly conserved. It plays critical roles in the development of eyes and pancreas and patterning of neural progenitors across species (Chi and Epstein, *Trends Genet.*, 2002, 18: 41-47). Indeed, the expression pattern of Pax6 in the developing human nervous system (after brain regions are formed) is very similar to that in other model systems, including mouse, frog, chick, and fish (Amirthalingam et al., *Biochem. Biophys. Res. Commun.*, 1995, 215: 122-128; Goulding et al., *Development*, 1993, 117: 1001-1016; Schlosser and Ahrens, *Dev. Biol.*, 2004, 271: 439-466; Walther and Gruss, *Development*, 1991, 113: 1435-1449). We have also confirmed that Pax6 is essential for patterning human NE cells to ventral spinal progenitors and dorsal telencephalic progenitors (Li et al., *Nat. Biotechnol.*, 2005, 23: 215-221; Li et al., *Development*, 2009, 136: 4055-4063). Our side-by-side comparison of Pax6 expression and function between mouse and human revealed a novel role of Pax6 in early human, but not mouse, pNSC specification. Considering the similar expression pattern of Pax6 in early rhesus monkey fetuses, this pNSC specification role of Pax6 probably is unique to primates. This finding raises a question as to why the classical transcription factor, with 100% amino acid sequence homology between mouse and human, acquires a new role in human brain development. The brain, especially the forebrain, is the most highly evolved structure in either size or complexity among species (Dorus et al., *Cell*, 2004, 119: 1027-1040; Kaas, *Curr. Biol.*, 2006, 16:R910-R914; Rakic, *Nat. Rev. Neurosci.*, 2009, 10: 724-735). Correspondingly to the increasing size of the forebrain, some neural transcription factors, especially anterior transcription factors Sox2 and Otx2 whose expression is restricted to the neural lineage in lower vertebrates, are now found at earlier developmental stages in mammals, even in the inner cell mass and the epiblast of the embryo (Avilion et al., *Genes Dev.*, 2003, 17: 126-140; Simeone et al., *EMBO J.*, 1993, 12: 2735-2747). The cerebrum in primates, especially in human, is proportionally larger and more complex in neural circuitry than in rodents (Dorus et al., *Cell*, 2004, 119: 1027-1040; Kaas, *Curr. Biol.*, 2006, 16:R910-R914; Rakic, *Nat. Rev. Neurosci.*, 2009, 10: 724-735). We and others have also found that under similar culture conditions without exogenous morphogens, hESC-derived NE cells tend to generate cortical glutamatergic neurons whereas mouse NE are inclined to generate ventral GABAergic neurons (Gaspard et al., *Nature*, 2008, 455: 351-357; Li et al., *Development*, 2009, 136: 4055-4063). We speculate that early Pax6 expression might be the first step to ensure a large cerebrum in primates. Further studies to identify target genes of Pax6 during NE specification may well shed light on the evolutionary complexities of our human brain. Our finding also raises the question of what would be the determinant gene for the NE fate in mouse or other animals. Comparison of our gene profiles with available database of mouse NE (Aiba et al., *Stem Cells*, 2006, 24: 889-895) revealed profound differences in gene expression between human and mouse NE, some of which are presented in Figure S1G in Zhang et al., 2010. While this comparison corroborates our present finding, it indicates a need of uncovering the long-sought NE determinant in animals.

Significance of Pax6 Overexpression in iPSCs

Overexpression of Pax6 or its derivatives will be an efficient way to convert human iPSCs to pNSCs. It is known that hESCs and human iPSCs employ identical transcriptional programs during neural differentiation (Zhang et al., *Cell Stem Cell*, 2010, 7: 90-100; Hu et al., *Proc Natl Acad Sci USA*, 2010, 107: 4335-4340). Not only do human iPSCs use the same transcriptional factors as hESCs to generate neuroepithelia and functionally appropriate neuronal types, iPSCs also follow the same developmental time course as hESCs in response to the same set of morphogens (Zhang et al., *Cell Stem Cell*, 2010, 7: 90-100). Consistent with what is known, we showed above, with various human ESC lines and human iPSCs, that pNSCs differentiated from both hESCs and iPSCs are Pax6+/Sox1−.

Overexpression of Pax6 or its derivatives may be an efficient way to convert human iPSCs to pNSCs. When applied with hESC differentiation protocol, human iPSCs do show lower efficiency in neural differentiation than hESCs. Using our neural differentiation protocol, human ESCs always end up with over 90% pNSCs after 8-10 days of differentiation, while neural differentiation efficiency of human iPSCs, in most cases, is less than 50%) (Hu et al., *Proc Natl Acad Sci USA*, 2010, 107: 4335-4340). We note lack of Pax6 expression at the initiation stage of pNSCs specification in iPSCs (data not shown) and believe the low neural differentiation efficiency of human iPSCs is rooted from inefficient activation of endogenous Pax6 expression when hESC neural differentiation protocol is used.

Example 2

Genes Highly Enriched in pNSCs but Down-Regulated in Regional NSCs pNSCs differ from regional NSCs in several aspects. For example, pNSCs are Pax6+/Sox1−, while regional NSCs are Sox1+. In addition, pNSCs have the potency to be patterned to all kinds of neural cells with different regional identities, but regional NSCs are fixed to certain regional identities. In order to further characterize the differences between pNSCs and regional NSCs, we compared the gene expression profiles of day10 pNSCs and day17 forebrain dorsal NSCs using an affymetrix mircroarray (Pankratz et al., *Stem Cells*, 2007, 25: 1511-1520; Li et al., *Development*, 2009, 136: 4055-4063). Genes which were expressed in pNSCs but their expression was down-regulated for at least 4 fold in regional NSCs are listed below in Table 1. These genes will thus be served as representative genes to separate pNSCs and regional NSCs. They are also candidate genes potentially useful for pNSCs reprogramming.

TABLE 1

| Affymetrix Probes | Genes | Physisological Functions |
|---|---|---|
| 211267_at | HESX homeobox 1 (HESX1) | transcription and DNA binding |
| 208449_s_at | fibroblast growth factor 8 (FGF8) | signal transduction and growth factor activity |

TABLE 1-continued

| Affymetrix Probes | Genes | Physiological Functions |
|---|---|---|
| 220448_at | potassium channel, subfamily K, member 12 (KCNK12) | ion channel activity |
| 213661_at | peptidase domain containing associated with muscle regeneration 1 (PAMR1) | proteolysis |
| 219545_at | potassium channel tetramerisation domain containing 14 (KCTD14) | ion channel activity |
| 204951_at | ras homolog gene family, member H (RHOH) | small GTPase mediated signal transduction |
| 206209_s_at | carbonic anhydrase IV (CA4) | carbonate dehydratase activity |
| 1552520_at | transmembrane protein 74 (TMEM74) | autophagy |
| 208893_s_at | dual specificity phosphatase 6 (DUSP6) | inactivation of MAPK activity |
| 205578_at | receptor tyrosine kinase-like orphan receptor 2 (ROR2) | nucleotide binding and kinase activity |
| 228335_at | claudin 11 (CLDN11) | cell adhesion |
| 219955_at | LINE-1 type transposase domain containing 1 (L1TD1) | N/A |
| 209466_x_at | pleiotrophin (PTN) | phosphoprotein phosphatase inhibitor activity and growth factor activity |
| 243161_x_at | zinc finger protein 42 homolog (ZFP42) | DNA binding and transcriptional activity |
| 213201_s_at | troponin T type 1 (TNNT1) | protein binding |

Example 3

Overexpression of Pax6 in Regional Neural Stem Cells Reverts the Regional NSCs to pNSCs.

Transcription factors have the potential to reverse the cell differentiation programs or trans-convert one cell fate to another. For example, Oct4, Sox2, Klf4 and c-Myc are the four typical transcription factors for reprogramming iPSCs (Yu et al., *Science*, 2007, 318: 1917-1920; Takahashi et al., *Cell*, 2007, 131: 861-872). In addition, Ascl1, Brn2 (also called Pou3f2) and Myt1l are sufficient to directly convert fibroblasts to neurons (Vierbuchen et al., *Nature*, 2010, 463: 1035-1041).

We hypothesized that regional NSCs can also be reprogrammed to pNCSs through forced expression of transcription factor(s) and Pax6 may be the critical factor given its unique role in specifying pNSCs. To test this hypothesis, we derived cortical NSCs from human fetal cortex (Schneider et al., Hum Mol Genet, 2007, 16: 651-666; Wright et al., Exp Cell Res, 2006, 312: 2107-2120). These regional NSCs are fate-restricted and do not have the potential to generate spinal cord progenitors (Wright et al., Exp Cell Res, 2006, 312: 2107-2120). As demonstrated in FIG. 6, the cortical NSCs with GFP overexpression do not grow well after retinoid acid challenging for five days. This indicates that these regional NSCs are fixed to the cortical fate and that they do not accommodate to the caudalization signal. This result is further supported by the fact that retinoid acid treatment failed to up-regulate HoxB4, a classic spinal cord gene, in the cortical NSCs.

In contrast, infecting the cortical NSCs with inducible lentiviruses, Pax6a and Pax6b followed by doxycycline treatment to overexpress both isoforms of Pax6 in these regional NSCs endows the cells with multi-potency. These cortical-fate fixed regional NSCs are now responsive to retinoid acid. They expand well and express HoxB4 after five days of retinoid acid treatment.

These data suggest that Pax6 expression reprograms regional NSCs to an earlier pNSC state, because only pNSCs are multi-potent and can be directed to different regional fates, such as responding to retinol acid and generating spinal cord NSCs.

Example 4

Overexpansion of pNSCs in Transplants Causes Tumor Formation.

hESCs and human iPSCs derived tissues or cell types are invaluable sources for replacement therapy. However, transplantation of stem cell derived neural cells is often ends up with over-growth of the grafts (Roy et al., *Nat. Med*, 2006, 12: 1259-1268; Sonntag et al., *Stem Cells*, 2007, 25: 411-418).

We checked our cultures used for future transplantation in Parkinson's disease animal models and found that there always were some Pax6 positive NSCs (FIG. 7A). After transplantation, we frequently identified tumors surrounding the cell injection spots. As demonstrated by FIG. 7B, the tumors were comprised of Pax6+/Sox1– pNSCs. These data suggest that the pNSCs within the transplants gradually lost of control and over-expand to form tumors. Down-regulation of Pax6 to drive the cells out of primitive state and ultimately differentiate the cells to neurons would be an efficient and safe way to eliminate tumor occurrence.

Example 5

A Non-Genetic Means to Regulate Pax6 Expression

The inventors envision that development of non-genetic strategies to regulate Pax6 expression may facilitate future clinical translation. One way to regulate transcription factors like Pax6 is to modulate protein degradation. We discovered that phosphorylation of certain serine residue blocks or enhances Pax6 degradation.

Figure 8:
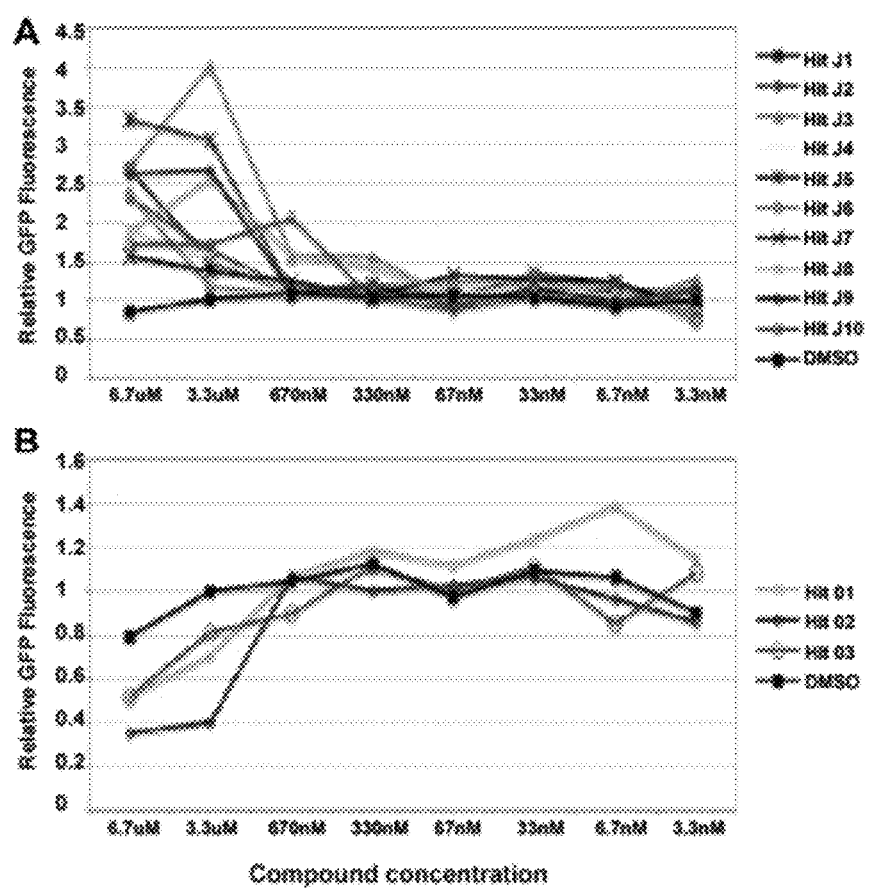
FIG. 8 demonstrates a non-genetic means to regulate Pax6 expression.

Using the HEK cells that express the mutant Pax6 constructs with a GFP tag, the inventors identified molecules that block Pax6 degradation (aiming at maintaining Pax6 level and the primitive state of NSCs, FIG. 8A) or promote Pax6 degradation (thus removing Pax6 and exiting cell cycle of NSCs, FIG. 8B) in their initial screening on library of pharmaceutically active compounds (LOPAC, 64,000 compounds), which were verified by dose-dependent effect. This will allow one to regulate Pax6 by non-genetic means, thus controlling the maintenance of and reprogramming of differentiated neural cells to the primitive state of NSCs or promote NSC differentiation thus lower the risk of tumor formation after transplantation.

Example 6

Experimental Procedures for the Previous Examples
Culture and Maintenance of Mouse and Human ESCs Protocols for culturing and maintenance of mouse and human ESCs are well known in the art. Briefly, hESCs (H9 and H1 lines, passages 18-35) were provided by the WiCell Institute (Madison, Wis.) and were cultured on irradiated mouse embryonic fibroblasts (MEFs) as previously described (Zhang et al., *Nat. Biotechnol.*, 2001, 19: 1129-1133; Zhang and Zhang, *Methods Mol. Biol.*, 2010, 584: 355-366).

Similarly, methods to generate iPSCs are also well-known in the art. In examples disclosed above, human iPSCs were generated from skin fibroblasts by overexpressing Oct4, Sox2, Klf4, and c-Myc through retroviral infection (Hu et al., *Proc. Natl. Acad. Sci. USA,* 2010, 107: 4335-4340). The standard protocol was also described by Park et al. (*Nat Protoc,* 2008, 3: 1180-1186).

Mouse ESCs (D3 line and Sox1/GFP reporter line 46C) were cultured on MEF supplemented with 50% medium conditioned by Buffalo rat liver cells (BRL-CM).

Neural Differentiation from Human and Mouse ESCs

Neural differentiation of hESCs was performed according to a published protocol (Zhang et al., *Nat. Biotechnol.,* 2001, 19: 1129-1133; Zhang and Zhang, *Methods Mol. Biol.,* 2010, 584: 355-366). For mESC neural differentiation, half a million cells were suspended in DMEM-F12/neurobasal medium (1:1 DMEM-F12/neurobasal medium, 13 N2 neural supplement, 13 lipid concentrate, 1 mM L-glutamine, 0.1 mM b-mercaptoethanol, and 40 mg/ml N-acetyl cysteine). For the first 2 days, 2 ng/ml of LIF was supplied. After another 7 days of culture in suspension without LIF, neruoepithelial aggregates were dissociated and plated in the same way as for human ESCs.

Tissue Collection

The human fetal tissues used in this study were from patients requesting termination of pregnancy. All the procedures were approved by the institutional review board (Ethics Committee) of Fudan University Shanghai Medical School and the Shanghai Institute of Biological Sciences, Chinese Academy of Science, Shanghai and with the informed consent of the patients. Fetal tissues were obtained within 4 hr after abortion and the developmental stages of fetus specimens were identified according to the anatomy established by Carnegie Institute in Washington, USA. Fetal monkey tissues were obtained from animals at the Wisconsin National Primate Research Center in early pregnancy as previously described (Bondarenko et al., *J. Immunol.,* 2007, 179: 8042-8050). The tissues were cut into 15-20 mm frozen sections for immunostaining.

Generation and Analysis of Teratomas

Human ESCs were injected subcutaneously into the backs of severe combined immnodeficient (SCID) mice (Jackson Laboratory) (Xia et al., *Stem Cells,* 2008, 26: 525-533). All animal experiments were performed according to the protocols approved by the Institutional Animal Care and Use Committee, University of Wisconsin.

Statistical Analysis

Data are presented as mean±SEM. Student's tests were used for statistical analysis. $P<0.05$ was considered significant.

DNA Construction

Pax6 and its mutants were constructed into pLenti vector with a FUGW backbone and an inducible lentiviral vector (Clontech) (Xia et al., *Stem Cells,* 2008, 26: 525-533). Primers for amplifying Pax6a (1-422) and Pax6b (1-436) are as follows: Forward, CATATTCGAGCCCCGTGGAATCC (SEQ ID NO: 1); Reverse, TTACTGTAATCTTGGCCAG-TATTG (SEQ ID NO: 2). Forward primer for amplifying Pax6 ΔPAI (77-422) is ATGAGAGTAGCGACTCCA-GAAGTTG (SEQ ID NO: 3) and forward primer for Pax6 ΔPD (202-422) is ATGCGACTTCAGCTGAAGCGG (SEQ ID NO: 4). For deleting HD in Pax6 (delete 210-269 in Pax6a and 224-283 in Pax6b), two step PCR is used with two additional primers: Forward, CGACTTCAGCTGAAGCGGAA-GAAACTGAGGAATCAGAGA (SEQ ID NO: 5); Reverse, GTCTTCTCTGATTCCTCAGTTTCTTC-CGCTTCAGCTGAAGTCG (SEQ ID NO: 6). For subcloning Pax6 dominant negative mutants (D/N), the last 78 amino acids of the PST transactivation domain are removed by the reverse primer, TTGCATAGGCAGGTTATTTGC (SEQ ID NO: 7). All the constructs have been verified by DNA sequencing.

Lentivirus Production and Transduction of ESCs

The constructs of lentiviral vectors for knockdown of Pax6 are shown in Figure S2 in Zhang et al., 2010 and lentivirus production was described previously (Xia et al., *Stem Cells,* 2008, 26: 525-533). For transduction of ESCs, human H9 ESCs or mouse ESCs (D3 and 46 C) were collected by brief centrifugation. Cell pellets were then incubated with 100 µl of concentrated virus (106 transducing units/ml) at 37° C. for 30 minutes. The virus and cell mixture was then transferred to the MEF feeder layer overnight before changing medium on the next day. Forty-eight hours after infection, blasticidin or puromycin was added to the cells for selecting drug-resistant clones. The final concentration of blasticidin or puromycin was 5 µg/ml for elongation factor-1 α (EF1α) promoter and 2 µg/ml for phosphoglycerate kinase (PGK) promoter. To make stable transduced monoclonal lines, ESCs were pretreated with ROCK inhibitor and then typsinized to single cells before plating on the MEF feeder (Watanabe et al., *Nat. Biotechnol.,* 2007, 25: 681-686).

The inducible lentivirus system, purchased from Clontech (Mountain View, Calif.), was modified by replacing the CMV promoter driving rtTA-Advanced in the pLVX-Tet-On Advanced vector with the EF1α promoter to optimize transgene expression in human ESCs.

Western Blotting

Cell pellets were lysed in a lysis buffer (1% Nonidet P-40, 50 mM Tris-HCl, pH 8.0, 0.5% sodium deoxycholate, 150 mM NaCl, 5 mM EDTA, with 10 mM NaF, 10 mM disodium pyrophosphate, and 1× protease inhibitor cocktail, Sigma) and passed through a 281/2 gauge needle several times. The particulate fraction was removed by centrifugation, and 30 µg of proteins in the supernatant were boiled in SDS-PAGE sample buffer and separated by SDS-PAGE.

Microarray Analysis

Luc RNAi and Pax6 RNAi human ESC lines were differentiated to NE cells for 6 days. Total RNA was extracted using Trizol (Invitrogen) and mRNA pooled from two individual lines of each group was hybridized on Affymetrix GeneChip Human Genome HG-U133 Plus 2.0 arrays according to the manufacturer's instructions. The data were deposited in the ArrayExpress database (accession number E-MEXP-2668).

mRNA Extraction and RT-PCR

Total RNA was isolated using the Trizol kit (Invitrogen). 1 µg of total RNA from each sample was reverse transcribed into cDNA and subjected to real-time PCR using the Power SYBR Green kit (Applied Biosystems, UK). Primer oligonucleotides used for real-time PCR were shown in Table 2 (most primers target both human and mouse genes except when they are specifically labeled):

TABLE 2

| Gene | Forward primer | Reverse primer |
| --- | --- | --- |
| Pax6 | TCTTTGCTTGGGAAATCCG (SEQ ID NO: 8) | CTGCCCGTTCAACATCCTTAG (SEQ ID NO: 9) |

TABLE 2-continued

| Gene | Forward primer | Reverse primer |
|---|---|---|
| Oct4 (human) | ACATCAAAGCTCTGCAGAAAGAACT (SEQ ID NO: 10) | CTGAATACCTTCCCAAATAGAACCC (SEQ ID NO: 11) |
| Oct4 (mouse) | ACATGAAAGCCCTGCAGAAGGAGCT (SEQ ID NO: 12) | GAGAACGCCCAGGGTGAGCC (SEQ ID NO: 13) |
| Nanog | ATTCTTCCACCAGTCCCAAA (SEQ ID NO: 14) | ATCTGCTGGAGGCTGAGGTA (SEQ ID NO: 15) |
| Sox2 | GCCCTGCAGTACAACTCCAT (SEQ ID NO: 16) | TGGAGTGGGAGGAAGAGGTA (SEQ ID NO: 17) |
| Fabp7 | TGTGACCAAACCAACGGTAAT (SEQ ID NO: 18) | CTTTGCCATCCCATTTCTGTA (SEQ ID NO: 19) |
| Lhx2 | TTACGGCAGGAAAACACGG (SEQ ID NO: 20) | TGCCAGGCACAGAAGTTAAG (SEQ ID NO: 21) |
| Six3 | ACTACCAGGAGGCCGAGAAG (SEQ ID NO: 22) | CAGTTCGCGTTTCTTGCTG (SEQ ID NO: 23) |
| Six6 | AACAAGAATGAGTCGGTGCT (SEQ ID NO: 24) | CAGCGGGAACTTCTTCCTTA (SEQ ID NO: 25) |
| Map2 | GGTCACAGGGCACCTATTCA (SEQ ID NO: 26) | TGTTCACCTTTCAGGACTGC (SEQ ID NO: 27) |
| Lmo3 | AAGGCACTGGACAAATACTGG (SEQ ID NO: 28) | CACGCATCACCATCTCAAAG (SEQ ID NO: 29) |
| Lix1 | GGAATTTTGGGAAAGCAAGC (SEQ ID NO: 30) | CAGCACTGAAAGTTGCCAAA (SEQ ID NO: 31) |
| Dlk1 | TCCTGAAGGTGTCCATGAAAG (SEQ ID NO: 32) | GTGGTTGTAGCGCAGGTTG (SEQ ID NO: 33) |
| Meis2 | CCAGGGGACTACGTTTCTCA (SEQ ID NO: 34) | TAACATTGTGGGGCTCTGTG (SEQ ID NO: 35) |
| Dach1 | GGTGGTGTGCAATGTGGA (SEQ ID NO: 36) | ATGCGGCATGATGTGAGAG (SEQ ID NO: 37) |
| N-Cad | TCCTGATATATGCCCAAGACAA (SEQ ID NO: 38) | TGACCCAGTCTCTCTTCTGC (SEQ ID NO: 39) |
| Sox1 | GTTTTTTGTAGTTGTTACCGC (SEQ ID NO: 40) | GCATTTACAAGAAATAATAC (SEQ ID NO: 41) |
| Nedd9 | CCCATCCAGATACCAAAAGG (SEQ ID NO: 42) | TCTCTCCCACTGGAACTGAA (SEQ ID NO: 43) |
| Nr2f2 | AAGCACTACGGCCAGTTCAC (SEQ ID NO: 44) | GTCTCATGCCCACTTTGAGG (SEQ ID NO:45) |
| Fezf2 | CGGCGAGAAGCAGTACAAAT (SEQ ID NO: 46) | GTTTGCGCACATGTTTCTTT (SEQ ID NO: 47) |
| Zic1 | AGCCACGATGCTCCTGGACGC (SEQ ID NO: 48) | TGGCCCAGGGCCGCAGCAGC (SEQ ID NO: 49) |
| Meis1 | GATGATTCAAGCCATACAAG (SEQ ID NO: 50) | GGGGTTCCTCCTGAACGAGT (SEQ ID NO: 51) |
| Mash1 | AACGAGCGCGAGCGCAACCG (SEQ ID NO: 52) | TTGGAGTAGTTGGGGGAGATG (SEQ ID NO: 53) |
| Pax3 | GCTGTGCCCAGGATGATGC (SEQ ID NO: 54) | CTGGTACCTGCACAGGATCT (SEQ ID NO: 55) |
| Lmo1 | ACGGAGCGCCCGAGATGATG (SEQ ID NO: 56) | GGCACAGGATGAGGTTGGCC (SEQ ID NO: 57) |
| Pou3f2 | CCGCAGCGTCTAACCACTAC (SEQ ID NO: 58) | GTGGGACAGCGCGGTGATCC (SEQ ID NO: 59) |
| Crx (human) | TATTCTGTCAACGCCTTGGCCCTA (SEQ ID NO: 60) | TGCATTTAGCCCTCCGGTTCTTGA (SEQ ID NO: 61) |

TABLE 2-continued

| Gene | Forward primer | Reverse primer |
|---|---|---|
| RPE65 (human) | GCCCTCCTGCACAAGTTTGACTTT (SEQ ID NO: 62) | AGTTGGTCTCTGTGCAAGCGTAGT (SEQ ID NO: 63) |
| Chx10 (human) | ATTCAACGAAGCCCACTACCCAGA (SEQ ID NO: 64) | ATCCTTGGCTGACTTGAGGATGGA (SEQ ID NO: 65) |
| FoxG1 (human) | AGAAGAACGGCAAGTACGAGA (SEQ ID NO: 66) | TGTTGAGGGACAGATTGTGGC (SEQ ID NO: 67) |
| En1 (human) | GGACAATGACGTTGAAACGCAGCA (SEQ ID NO: 68) | AAGGTCGTAAGCGGTTTGGCTAGA (SEQ ID NO: 69) |
| Hoxb4 | AAAGAGCCCGTCGTCTACC (SEQ ID NO: 70) | GTGTAGGCGGTCCGAGAG (SEQ ID NO: 71) |
| Nkx2.1 (human) | AACCAAGCGCATCCAATCTCAAGG (SEQ ID NO: 72) | TGTGCCCAGAGTGAAGTTTGGTCT (SEQ ID NO: 73) |
| Cdx2 | TGGAGCTGGAGAAGGAGTTT (SEQ ID NO: 74) | CTGCTGCTGCTGTTGCTG (SEQ ID NO: 75) |
| Gata6 | GTGAACTGCGGCTCCATC (SEQ ID NO: 76) | GTGTGACAGTTGGCACAGGA (SEQ ID NO: 77) |
| K18 | ATGCGCCAGTCTGTGGAG (SEQ ID NO: 78) | CCTGAGATTTGGGGGCATC (SEQ ID NO: 79) |
| Lama3 | TGTTAATCGGGCAACACAAA (SEQ ID NO: 80) | GGTGCTTTCCAAAGTTCCTG (SEQ ID NO: 81) |
| Brachyury (human) | ACAGCCAGCAACCTGGGTA (SEQ ID NO: 82) | CATGCAGGTGAGTTGTCAGAA (SEQ ID NO: 83) |
| Sox17 | ATACGCCAGTGACGACCAG (SEQ ID NO: 84) | GCGGCCGGTACTTGTAGTT (SEQ ID NO: 85) |
| Hnf1b | AGAGGGAGGTGGTCGATGTC (SEQ ID NO: 86) | AGCTGATCCTGACTGCTTTTG (SEQ ID NO: 87) |
| Pdx1 | CAAAGCTCACGCGTGGAAAG (SEQ ID NO: 88) | TGATGTGTCTCTCGGTCAAG (SEQ ID NO: 89) |
| Vegfr2 | TAGAAGGTGCCCAGGAAAAG (SEQ ID NO: 90) | CAAGTAGCCTGTCTTCAGTTC (SEQ ID NO: 91) |
| Gapdh | GAAGGTGAAGGTCGGAGTC (SEQ ID NO: 92) | GAAGATGGTGATGGGATTTC (SEQ ID NO: 93) |

For separating Pax6a and Pax6b, primer sets spanning exon5a (Forward: CGGAGTGAATCAGCTCGGTG (SEQ ID NO: 94); Reverse: CCGCTTATACTGGGCTATTTGC (SEQ ID NO: 95) were used for regular PCR and analyzed by 2.5% gel.

Chromatin Immunoprecipitation (ChIP)

Inducible GFP, Pax6a-GFP and Pax6b-GFP human ESC lines were treated with 2 µg/ml doxycycline for 1 or 3 days to induce transgene expression. After cross-linking with 1% formaldehyde at 37° C. for 10 min, the cells were harvested by scraping. The fixed cells were then washed and prepared with the EZ-ChIP™ (a kit for performing ChIP) kit according to the manufacturer's suggestions (Millipore). The chromatin was sheared by sonication and incubated with GFP antibody (Chemicon, rabbit IgG). The immunoprecipitates were then washed five times, crosslinks were reversed and immunoprecipitated DNA was subjected to qRT-PCR analysis. Primer pairs against promoter regions of the pluripotent and NE genes were shown in Table 4:

TABLE 4

| Targets | Forward primer | Reverse primer |
|---|---|---|
| Oct4 | ACCAGGCCCCATAATCTACC (SEQ ID NO: 96) | TTCCCCCACTCTTATGTTGC (SEQ ID NO: 97) |
| Nanog | GGGGGATACTCGGGATACTC (SEQ ID NO: 98) | GGAAAAGCAGGGTGACATTC (SEQ ID NO: 99) |
| Fabp7 | CGGACATACTTCTGACTTTTTGG (SEQ ID NO: 100) | GATGCTCTGTGGCAAGATGA (SEQ ID NO: 101) |
| Six3 | ACGGCTGTCTCTGGCTAAGT (SEQ ID NO: 102) | GGGAAACCTAACGTGACTGG (SEQ ID NO: 103) |
| Lmo3 | CCAGCGAGGGGTAACAGAT (SEQ ID NO: 104) | CAGCCAATGCACTGAGAAGA (SEQ ID NO: 105) |

TABLE 4-continued

| Targets | Forward primer | Reverse primer |
|---|---|---|
| Meis2 | GCCAAACTGAGGCTCT TCAA (SEQ ID NO: 106) | CCCCCTTTCCTGGTAG GTAT (SEQ ID NO: 107) |
| Dach1 | GTGGAAAACACCCCTC AGAA (SEQ ID NO: 108) | CTTGTTCCACATTGCA CACC (SEQ ID NO: 109) |
| N-Cad | AAAAGCCTAGCCAGCA ACAG (SEQ ID NO: 110) | GCTTTTCTGCTTTGGG TGAC (SEQ ID NO: 111) |

Immunostaining

Antibodies used in this study for immunostaining were Pax6 (1:5,000, mouse IgG, Developmental Studies Hybridoma Bank), Sox1 (1:1,000, goat IgG, R&D), Otx2 (1:2,000, goat IgG, R&D), FoxG1 (1:1,500; gift from Dr. Y. Sasai), Sox2 (1:1,000, goat IgG, R&D), Fabp7 (1:1,000, rabbit IgG, Chemicon), N-cadherin (1:1,000, mouse IgG, Santa Cruz Biotechnology), Brachyury (1:50, goat IgG, R&D), AFP (1:500, rabbit IgG, NeoMarkers) and Gata6 (1:500, rabbit IgG, Santa Cruz Biotechnology).

Proliferation Analysis

Proliferation of Pax6 knockdown lines or Pax6 overexpression lines was assessed using a "Click-iT EdU" kit purchased from Invitrogen according to the manufacturer's instructions (Weick et al., *Stem Cells,* 2009, 27: 2906-2916). For Luc RNAi and Pax6 RNAi lines, cells were differentiated for 8 days and 10 μM EdU was added to the cells and allowed for 6 hours of incorporation before fixation and EdU detection. For inducible overexpression lines, cells were treated with doxycycline for 1, 2 and 3 days. The cells were then labeled with EdU for another 6 hours in the presence of doxycycline.

Cell Cycle Analysis

Cells were trypsinized into single cells and fixed in 75% ethanol/PBS overnight. Cells were then washed with PBS and stained with propidium iodide solution (3.8 mM sodium citrate, 50 μg/ml propidium iodide, 0.5 μg/ml RNase A) for 3 hours before analyzed by flow cytometry.

We claim:

1. An isolated primate primitive neural stem cell (primate pNSC) that overexpresses an exogenous Pax6 nucleic acid sequence, wherein said Pax6 expression is sufficient to maintain proliferating Pax6+/Sox1 primate pNSCs in vitro without differentiation.

2. A population of the primate pNSCs of claim 1, wherein said Pax6 expression is sufficient to maintain proliferating Pax6+/Sox1 primate pNSCs in vitro without differentiation.

3. The population of primate pNSCs in claim 2, wherein the cells continue to proliferate without differentiating.

4. The population of primate pNSCs in claim 3, wherein the cells continue to proliferate without differentiating for at least a week.

5. The population of primate pNSCs in claim 3, wherein the cells continue to proliferate without differentiating for at least two weeks.

6. The population of claim 2, wherein the primate is human.

7. The primate primitive neural stem cell (pNSC) of claim 1, wherein the cell is capable of differentiating into a neuron, an astrocyte, or an oligodendrocyte.

8. The primate pNSC of claim 7, wherein the neuron is a projection neuron of the brain or spinal cord.

9. The primate pNSC of claim 1, wherein the primate pNSC is derived from a pluripotent stem cell.

10. The primate pNSC of claim 9, wherein the pluripotent stem cell is an embryonic stem cell.

11. The primate pNSC of claim 9, wherein the pluripotent stem cell is an induced pluripotent stem cell.

* * * * *

SEQUENCE LISTING

```
<160> NUMBER OF SEQ ID NOS: 124

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
catattcgag ccccgtggaa tcc                                            23

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
ttactgtaat cttggccagt attg                                           24

<210> SEQ ID NO 3
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 3
atgagagtag cgactccaga agttg                                          25

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
atgcgacttc agctgaagcg g                                              21

<210> SEQ ID NO 5
```

```
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
cgacttcagc tgaagcggaa gaaactgagg aatcagaga                               39

<210> SEQ ID NO 6
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 6
gtcttctctg attcctcagt ttcttccgct tcagctgaag tcg                         43

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
ttgcataggc aggttatttg c                                                  21

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 8
tctttgcttg ggaaatccg                                                     19

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
ctgcccgttc aacatcctta g                                                  21

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
acatcaaagc tctgcagaaa gaact                                              25

<210> SEQ ID NO 11
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 11
```

```
ctgaatacct tcccaaatag aaccc                                            25

<210> SEQ ID NO 12
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 12
acatgaaagc cctgcagaag gagct                                            25

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
gagaacgccc agggtgagcc                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
attcttccac cagtcccaaa                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
atctgctgga ggctgaggta                                                  20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
gccctgcagt acaactccat                                                  20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tggagtggga ggaagaggta                                                  20

<210> SEQ ID NO 18
<211> LENGTH: 21
<212> TYPE: DNA
```

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
tgtgaccaaa ccaacggtaa t                                    21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
ctttgccatc ccatttctgt a                                    21

<210> SEQ ID NO 20
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 20
ttacggcagg aaaacacgg                                       19

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tgccaggcac agaagttaag                                      20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
actaccagga ggccgagaag                                      20

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
cagttcgcgt ttcttgctg                                       19

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
aacaagaatg agtcggtgct                                      20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
cagcgggaac ttcttcctta                                        20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
ggtcacaggg cacctattca                                        20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tgttcacctt tcaggactgc                                        20

<210> SEQ ID NO 28
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 28
aaggcactgg acaaatactg g                                      21

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
cacgcatcac catctcaaag                                        20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
ggaattttgg gaaagcaagc                                        20

<210> SEQ ID NO 31
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 31
cagcactgaa agttgccaaa                           20

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
tcctgaaggt gtccatgaaa g                         21

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
gtggttgtag cgcaggttg                            19

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ccaggggact acgtttctca                           20

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
taacattgtg gggctctgtg                           20

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 36
ggtggtgtgc aatgtgga                             18

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
atgcggcatg atgtgagag                            19

```
<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
tcctgatata tgcccaagac aa                                               22

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
tgacccagtc tctcttctgc                                                  20

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 40 gtttttgta gttgttaccg c                                                 21

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
gcatttacaa gaaataatac                                                  20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
cccatccaga taccaaaagg                                                  20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
tctctcccac tggaactgaa                                                  20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 44
aagcactacg gccagttcac                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
gtctcatgcc cactttgagg                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
cggcgagaag cagtacaaat                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gtttgcgcac atgtttcttt                                              20

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
agccacgatg ctcctggacg c                                            21

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
tggcccaggg ccgcagcagc                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gatgattcaa gccatacaag                                              20

<210> SEQ ID NO 51
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 51
ggggttcctc ctgaacgagt                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
aacgagcgcg agcgcaaccg                                               20

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
ttggagtagt tgggggagat g                                             21

<210> SEQ ID NO 54
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 54
gctgtgccca ggatgatgc                                                19

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
ctggtacctg cacaggatct                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
acggagcgcc cgagatgatg                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
```

```
ggcacaggat gaggttggcc                                              20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
ccgcagcgtc taaccactac                                              20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
gtgggacagc gcggtgatcc                                              20

<210> SEQ ID NO 60
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 60
tattctgtca acgccttggc ccta                                         24

<210> SEQ ID NO 61
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 61
tgcatttagc cctccggttc ttga                                         24

<210> SEQ ID NO 62
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 62
gccctcctgc acaagtttga cttt                                         24

<210> SEQ ID NO 63
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 63
agttggtctc tgtgcaagcg tagt                                         24

<210> SEQ ID NO 64
<211> LENGTH: 24
<212> TYPE: DNA
<213> ORGANISM: Artificial Sequence
```

```
<220> FEATURE:
<223> OTHER INFORMATION: Synthetic oligonucleotide

<400> SEQUENCE: 64
attcaacgaa gcccactacc caga                                              24

<210> SEQ ID NO 65
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 65
atccttggct gacttgagga tgga                                              24

<210> SEQ ID NO 66
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 66
agaagaacgg caagtacgag a                                                 21

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 67
tgttgaggga cagattgtgg c                                                 21

<210> SEQ ID NO 68
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 68
ggacaatgac gttgaaacgc agca                                              24

<210> SEQ ID NO 69
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 69
aaggtcgtaa gcggtttggc taga                                              24

<210> SEQ ID NO 70
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 70
aaagagcccg tcgtctacc                                                    19
```

```
<210> SEQ ID NO 71
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 71
gtgtaggcgg tccgagag                                                 18

<210> SEQ ID NO 72
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 72
aaccaagcgc atccaatctc aagg                                          24

<210> SEQ ID NO 73
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 73
tgtgcccaga gtgaagtttg gtct                                          24

<210> SEQ ID NO 74
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 74
tggagctgga gaaggagttt                                               20

<210> SEQ ID NO 75
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 75
ctgctgctgc tgttgctg                                                 18

<210> SEQ ID NO 76
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 76
gtgaactgcg gctccatc                                                 18

<210> SEQ ID NO 77
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 77
gtgtgacagt tggcacagga                                           20

<210> SEQ ID NO 78
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 78
atgcgccagt ctgtggag                                             18

<210> SEQ ID NO 79
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 79
cctgagattt gggggcatc                                            19

<210> SEQ ID NO 80
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 80
tgttaatcgg gcaacacaaa                                           20

<210> SEQ ID NO 81
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 81
ggtgctttcc aaagttcctg                                           20

<210> SEQ ID NO 82
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 82
acagccagca acctgggta                                            19

<210> SEQ ID NO 83
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 83
catgcaggtg agttgtcaga a                                         21

<210> SEQ ID NO 84

```
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 84
atacgccagt gacgaccag                                                    19

<210> SEQ ID NO 85
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 85
gcggccggta cttgtagtt                                                    19

<210> SEQ ID NO 86
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 86
agagggaggt ggtcgatgtc                                                   20

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 87
agctgatcct gactgctttt g                                                 21

<210> SEQ ID NO 88
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 88
caaagctcac gcgtggaaag                                                   20

<210> SEQ ID NO 89
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 89
tgatgtgtct ctcggtcaag                                                   20

<210> SEQ ID NO 90
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 90
```
tagaaggtgc ccaggaaaag                                               20

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
caagtagcct gtcttcagtt c                                             21

<210> SEQ ID NO 92
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 92
gaaggtgaag gtcggagtc                                                19

<210> SEQ ID NO 93
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 93
gaagatggtg atgggatttc                                               20

<210> SEQ ID NO 94
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 94
cggagtgaat cagctcggtg                                               20

<210> SEQ ID NO 95
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 95
ccgcttatac tgggctattt tgc                                           23

<210> SEQ ID NO 96
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 96
accaggcccc ataatctacc                                               20

<210> SEQ ID NO 97
<211> LENGTH: 20
<212> TYPE: DNA

```
<213> ORGANISM: Artificial Sequence
<220> FEATURE:
<223> OTHER INFORMATION: Synthetic oligonucleotide

<400> SEQUENCE: 97
ttcccccact cttatgttgc                                             20

<210> SEQ ID NO 98
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 98
gggggatact cgggatactc                                             20

<210> SEQ ID NO 99
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 99
ggaaaagcag ggtgacattc                                             20

<210> SEQ ID NO 100
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 100
cggacatact tctgactttt tgg                                         23

<210> SEQ ID NO 101
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 101
gatgctctgt ggcaagatga                                             20

<210> SEQ ID NO 102
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 102
acggctgtct ctggctaagt                                             20

<210> SEQ ID NO 103
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 103
gggaaaccta acgtgactgg                                             20
```

<210> SEQ ID NO 104
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 104
ccagcgaggg gtaacagat                                                    19

<210> SEQ ID NO 105
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 105
cagccaatgc actgagaaga                                                   20

<210> SEQ ID NO 106
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 106
gccaaactga ggctcttcaa                                                   20

<210> SEQ ID NO 107
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 107
cccccttccc tggtaggtat                                                   20

<210> SEQ ID NO 108
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 108
gtggaaaaca cccctcagaa                                                   20

<210> SEQ ID NO 109
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 109
cttgttccac attgcacacc                                                   20

<210> SEQ ID NO 110
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 110
aaaagcctag ccagcaacag                                                     20

<210> SEQ ID NO 111
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 111
gcttttctgc tttgggtgac                                                     20

<210> SEQ ID NO 112
<211> LENGTH: 422
<212> TYPE: PRT
<213> ORGANISM: Homo sapiens

<400> SEQUENCE: 112

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Leu Gln Arg Asn Arg Thr Ser Phe Thr Gln Glu Gln Ile Glu Ala
    210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
        275                 280                 285

```
Ser Ser Phe Ser Thr Ser Val Tyr Gln Pro Ile Pro Gln Pro Thr Thr
        290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
                340                 345                 350

Ser Tyr Ser Cys Met Leu Pro Thr Ser Pro Ser Val Asn Gly Arg Ser
        355                 360                 365

Tyr Asp Thr Tyr Thr Pro Pro His Met Gln Thr His Met Asn Ser Gln
    370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
            420

<210> SEQ ID NO 113
<211> LENGTH: 6947
<212> TYPE: DNA
<213> ORGANISM: Homo sapiens

<400> SEQUENCE: 113
ggtgcatttg catgttgcgg agtgattagt gggtttgaaa agggaaccgt ggctcggcct      60
catttcccgc tctggttcag gcgcaggagg aagtgttttg ctggaggatg atgacagagg     120
tcaggcttcg ctaatgggcc agtgaggagc ggtggaggcg aggccgggcg ccggcacaca     180
cacattaaca cacttgagcc atcaccaatc agcataggaa tctgagaatt gctctcacac     240
accaacccag caacatccgt ggagaaaact ctcaccagca actcctttaa acaccgtca      300 tttcaaacca ttgtggtctt caagcaacaa cagcagcaca aaaaacccca accaaacaaa     360
actcttgaca gaagctgtga caaccagaaa ggatgcctca taaggggga agactttaac      420 taggggcgcg cagatgtgtg aggcctttta ttgtgagagt ggacagacat ccgagatttc     480
agagccccat attcgagccc cgtggaatcc cgcggccccc agccagagcc agcatgcaga     540
acagtcacag cggagtgaat cagctcggtg gtgtctttgt caacgggcgg ccactgccgg     600
actccacccg gcagaagatt gtagagctag ctcacagcgg ggcccggccg tgcgacattt     660
cccgaattct gcaggtgtcc aacggatgtg tgagtaaaat tctgggcagg tattacgaga     720
ctggctccat cagacccagg gcaatcggtg gtagtaaacc gagagtagcg actccagaag     780
ttgtaagcaa aatagcccag tataagcggg agtgcccgtc catctttgct tgggaaatcc     840
gagacagatt actgtccgag gggtctgta ccaacgataa cataccaagc gtgtcatcaa      900
taaacagagt tcttcgcaac ctggctagcg aaaagcaaca gatgggcgca gacggcatgt     960
atgataaact aaggatgttg aacgggcaga ccggaagctg gggcacccgc cctggttggt    1020
atccggggac ttcggtgcca gggcaaccta cgcaagatgg ctgccagcaa caggaaggag    1080
ggggagagaa taccaactcc atcagttcca acggagaaga ttcagatgag gctcaaatgc    1140
gacttcagct gaagcggaag ctgcaaagaa atagaacatc ctttacccaa gagcaaattg    1200
aggccctgga gaaagagttt gagagaaccc attatccaga tgtgtttgcc cgagaaagac    1260
tagcagccaa aatagatcta cctgaagcaa gaatacaggt atggttttct aatcgaaggg    1320
```

```
ccaaatggag aagagaagaa aaactgagga atcagagaag acaggccagc aacacaccta    1380
gtcatattcc tatcagcagt agtttcagca ccagtgtcta ccaaccaatt ccacaaccca    1440
ccacaccggt ttcctccttc acatctggct ccatgttggg ccgaacagac acagccctca    1500
caaacaccta cagcgctctg ccgcctatgc ccagcttcac catggcaaat aacctgccta    1560
tgcaaccccc agtccccagc cagacctcct catactcctg catgctgccc accagccctt    1620
cggtgaatgg gcggagttat gatacctaca ccccccaca tatgcagaca cacatgaaca    1680
gtcagccaat gggcacctcg ggcaccactt caacaggact catttcccct ggtgtgtcag    1740
ttccagttca agtccccgga agtgaacctg atatgtctca atactggcca agattacagt    1800 aaaaaaaaa aaaaaaaaa aaaggaaagg aaatattgtg ttaattcagt cagtgactat    1860
ggggacacaa cagttgagct ttcaggaaag aaagaaaaat ggctgttaga gccgcttcag    1920
ttctacaatt gtgtcctgta ttgtaccact ggggaaggaa tggacttgaa acaaggacct    1980
ttgtatacag aaggcacgat atcagttgga acaaatcttc attttggtat ccaaactttt    2040
attcattttg gtgtattatt tgtaaatggg catttgtatg ttataatgaa aaaagaaca    2100 atgtagactg gatggatgtt tgatctgtgt tggtcatgaa gttgttttt ttttttttaa    2160 aaagaaaacc atgatcaaca agctttgcca cgaatttaag agttttatca agatatatcg    2220
aatacttcta cccatctgtt catagtttat ggactgatgt tccaagtttg tatcattcct    2280
ttgcatataa ttaaacctgg aacaacatgc actagattta tgtcagaaat atctgttggt    2340
tttccaaagg ttgttaacag atgaagttta tgtgcaaaaa agggtaagat ataaattcaa    2400
ggaagaaaaa aagttgatag ctaaaaggta gagtgtgtct tcgatataat ccaatttgtt    2460
ttatgtcaaa atgtaagtat ttgtcttccc tagaaatcct cagaatgatt tctataataa    2520
agttaatttc atttatattt gacaagaata tagatgtttt atacacattt tcatgcaatc    2580
atacgtttct tttttggcca gcaaaagtta attgttctta gatatagttg tattactgtt    2640
cacggtccaa tcattttgtg catctagagt tcattcctaa tcaattaaaa gtgcttgcaa    2700
gagttttaaa cttaagtgtt ttgaagttgt tcacaactac atatcaaaat taaccattgt    2760
tgattgtaaa aaaccatgcc aaagcctttg tatttccttt attatacagt tttcttttta    2820 acctttatagt gtggtgttac aaattttatt tccatgttag atcaacattc taaaccaatg    2880
gttactttca cacacactct gttttacatc ctgatgatcc ttaaaaaata atccttatag    2940
ataccataaa tcaaaacgt gttagaaaaa aattccactt acagcagggt gtagatctgt    3000
gcccatttat acccacaaca tatatacaaa atggtaacat ttcccagtta gccatttaat    3060
tctaaagctc aaagtctaga ataatttaa aaatgcaaca agcgattagc taggaattgt    3120
tttttgaatt aggactggca ttttcaatct gggcagattt ccattgtcag cctatttcaa    3180
caatgatttc actgaagtat attcaaaagt agatttctta aaggagactt tctgaaagct    3240
gttgcctttt tcaaataggc cctctcccctt ttctgtctcc ctcccctttg cacaagaggc    3300
atcatttccc attgaaccac tacagctgtt cccatttgaa tcttgctttc tgtgcggttg    3360
tggatggttg gagggtggag gggggatgtt gcatgtcaag gaataatgag cacagacaca    3420
tcaacagaca acaacaaagc agactgtgac tggccggtgg gaattaaagg ccttcagtca    3480
ttggcagctt aagccaaaca ttcccaaatc tatgaagcag ggcccattgt tggtcagttg    3540
ttatttgcaa tgaagcacag ttctgatcat gtttaaagtg gaggcacgca gggcaggagt    3600
gcttgagccc aagcaaagga tggaaaaaaa taagcctttg ttgggtaaaa aaggactgtc    3660
```

```
tgagactttc atttgttctg tgcaacatat aagtcaatac agataagtct tcctctgcaa      3720
acttcactaa aaagcctggg ggttctggca gtctagatta aaatgcttgc acatgcagaa      3780
acctctgggg acaaagacac acttccactg aattatactc tgctttaaaa aaatcccaa      3840 aagcaaatga tcagaaatgt agaaattaat ggaaggattt aaacatgacc ttctcgttca      3900
atatctactg ttttttagtt aaggaattac ttgtgaacag ataattgaga ttcattgctc      3960
cggcatgaaa tatactaata attttattcc accagagttg ctgcacattt ggagacacct      4020
tcctaagttg cagttttttgt atgtgtgcat gtagttttgt tcagtgtcag cctgcactgc      4080
acagcagcac atttctgcag gggagtgagc acacatacgc actgttggta caattgccgg      4140
tgcagacatt tctacctcct gacattttgc agcctacatt ccctgagggc tgtgtgctga      4200
gggaactgtc agagaagggc tatgtgggag tgcatgccac agctgctggc tggcttactt      4260
cttccttctc gctggctgta atttccacca cggtcaggca gccagttccg gcccacggtt      4320
ctgttgtgta gacagcagag actttggaga cccggatgtc gcacgccagg tgcaagaggt      4380
gggaatggga gaaaaggagt gacgtgggag cggagggtct gtatgtgtgc acttgggcac      4440
gtatatgtgt gctctgaagg tcaggattgc cagggcaaag tagcacagtc tggtatagtc      4500
tgaagaagcg gctgctcagc tgcagaagcc ctctggtccg gcaggatggg aacggctgcc      4560
ttgccttctg cccacaccct agggacatga gctgtccttc caaacagagc tccaggcact      4620
ctcttgggga cagcatggca ggctctgtgt ggtagcagtg cctgggagtt ggccttttac      4680
tcattgttga ataatttttt gtttattatt tatttaacga tacatatatt tatatattta      4740
tcaatggggt atctgcaggg atgttttgac accatcttcc aggatggaga ttatttgtga      4800
agacttcagt agaatcccag gactaaacgt ctaaattttt tctccaaact tgactgactt      4860
gggaaaacca ggtgaataga ataagagctg aatgttttaa gtaataaacg ttcaaactgc      4920
tctaagtaaa aaaatgcatt ttactgcaat gaatttctag aatattttttc ccccaaagct      4980 atgcctccta acccttaaat ggtgaacaac tggtttcttg ctacagctca ctgccatttc      5040
ttcttactat catcactagg tttcctaaga ttcactcata cagtattatt tgaagattca      5100
gctttgttct gtgaatgtca tcttaggatt gtgtctatat tcttttgctt atttcttttt      5160
actctgggcc tctcatacta gtaagatttt aaaaagcctt ttcttctctg tatgtttggc      5220
tcaccaaggc gaaatatata ttcttctctt tttcatttct caagaataaa cctcatctgc      5280 tttttttgttt ttctgtgttt tggcttggta ctgaatgact caactgctcg gttttaaagt      5340
tcaaagtgta agtacttagg gttagtactg cttatttcaa taatgttgac ggtgactatc      5400
tttggaaagc agtaacatgc tgtcttagaa atgcattaa taatgggctt aaacaaatga      5460
ataggggggt ccccccactc tccttttgta tgcctatgtg tgtctgattt gttaaaagat      5520
ggacagggaa ttgattgcag agtgtcgctt ccttctaaag tagttttatt ttgtctactg      5580
ttagtattta aagatcctgg aggtggacat aaggaataaa tggaagagaa aagtagatat      5640
tgtatggtgg ctactaaaag gaaattcaaa aagtcttaga acccgagcac ctgagcaaac      5700
tgcagtagtc aaaatatttta tctcatgtta aagaaaggca aatctagtgt aagaaatgag      5760
taccatatag ggttttgaag ttcatatact agaaacactt aaaagatatc atttcagata      5820
ttacgtttgg cattgttctt aagtatttat atctttgagt caagctgata attaaaaaaa      5880
atctgttaat ggagtgtata tttcataatg tatcaaaatg gtgtctatac ctaaggtagc      5940
attattgaag agagatatgt ttatgtagta agttattaac ataatgagta acaaataatg      6000
tttccagaag aaaggaaaac acattttcag agtgcgtttt tatcagagga agacaaaaat      6060
```

```
acacacccct ctccagtagc ttattttttac aaagccggcc cagtgaatta gaaaaacaaa    6120
gcacttggat atgattttgg gaaagcccag gtacacttat tattcaaaat gcacttttac    6180
tgagtttgaa aagtttcttt tatatttaaa ataagggttc aaatatgcat attcaatttt    6240
tatagtagtt atctatttgc aaagcatata ttaactagta attggctgtt aattttatag    6300
acatggtagc cagggaagta tatcaatgac ctattaagta ttttgacaag caatttacat    6360
atctgatgac ctcgtatctc ttttcagca agtcaaatgc tatgtaattg ttccattgtg    6420
tgttgtataa aatgaatcaa cacggtaaga aaaaggttag agttattaaa ataataaact    6480
gactaaaata ctcatttgaa tttattcaga atgttcataa tgctttcaaa ggacatagca    6540
gagcttttgt ggagtatccg cacaacatta tttattatct atggactaaa tcaattttttt    6600 gaagttgctt taaaatttaa aagcaccttt gcttaatata aagccctttta attttaactg    6660 acagatcaat tctgaaactt tattttgaaa agaaaatggg gaagaatctg tgtctttaga    6720
attaaaagaa atgaaaaaaa taaacccgac attctaaaaa aatagaataa gaaacctgat    6780
ttttagtact aatgaaatag cgggtgacaa aatagttgtc tttttgattt tgatcacaaa    6840
aaataaactg gtagtgacag gatatgatgg agagatttga catcctggca aatcactgtc    6900
attgattcaa ttattctaat tctgaataaa agctgtatac agtaaaa                  6947
```

<210> SEQ ID NO 114
<211> LENGTH: 436
<212> TYPE: PRT
<213> ORGANISM: Homo sapiens

<400> SEQUENCE: 114

```
Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45

His Ala Asp Ala Lys Val Gln Val Leu Asp Asn Gln Asn Val Ser Asn
    50                  55                  60

Gly Cys Val Ser Lys Ile Leu Gly Arg Tyr Tyr Glu Thr Gly Ser Ile
65                  70                  75                  80

Arg Pro Arg Ala Ile Gly Gly Ser Lys Pro Arg Val Ala Thr Pro Glu
                85                  90                  95

Val Val Ser Lys Ile Ala Gln Tyr Lys Arg Glu Cys Pro Ser Ile Phe
            100                 105                 110

Ala Trp Glu Ile Arg Asp Arg Leu Leu Ser Glu Gly Val Cys Thr Asn
        115                 120                 125

Asp Asn Ile Pro Ser Val Ser Ser Ile Asn Arg Val Leu Arg Asn Leu
    130                 135                 140

Ala Ser Glu Lys Gln Gln Met Gly Ala Asp Gly Met Tyr Asp Lys Leu
145                 150                 155                 160

Arg Met Leu Asn Gly Gln Thr Gly Ser Trp Gly Thr Arg Pro Gly Trp
                165                 170                 175

Tyr Pro Gly Thr Ser Val Pro Gly Gln Pro Thr Gln Asp Gly Cys Gln
            180                 185                 190

Gln Gln Glu Gly Gly Gly Glu Asn Thr Asn Ser Ile Ser Ser Asn Gly
        195                 200                 205

Glu Asp Ser Asp Glu Ala Gln Met Arg Leu Gln Leu Lys Arg Lys Leu
```

```
                210                 215                 220

Gln Arg Asn Arg Thr Ser Phe Thr Gln Glu Gln Ile Glu Ala Leu Glu
225                 230                 235                 240

Lys Glu Phe Glu Arg Thr His Tyr Pro Asp Val Phe Ala Arg Glu Arg
                245                 250                 255

Leu Ala Ala Lys Ile Asp Leu Pro Glu Ala Arg Ile Gln Val Trp Phe
                260                 265                 270

Ser Asn Arg Arg Ala Lys Trp Arg Arg Glu Glu Lys Leu Arg Asn Gln
                275                 280                 285

Arg Arg Gln Ala Ser Asn Thr Pro Ser His Ile Pro Ile Ser Ser Ser
290                 295                 300

Phe Ser Thr Ser Val Tyr Gln Pro Ile Pro Gln Pro Thr Thr Pro Val
305                 310                 315                 320

Ser Ser Phe Thr Ser Gly Ser Met Leu Gly Arg Thr Asp Thr Ala Leu
                325                 330                 335

Thr Asn Thr Tyr Ser Ala Leu Pro Pro Met Pro Ser Phe Thr Met Ala
                340                 345                 350

Asn Asn Leu Pro Met Gln Pro Pro Val Pro Ser Gln Thr Ser Ser Tyr
                355                 360                 365

Ser Cys Met Leu Pro Thr Ser Pro Ser Val Asn Gly Arg Ser Tyr Asp
                370                 375                 380

Thr Tyr Thr Pro Pro His Met Gln Thr His Met Asn Ser Gln Pro Met
385                 390                 395                 400

Gly Thr Ser Gly Thr Thr Ser Thr Gly Leu Ile Ser Pro Gly Val Ser
                405                 410                 415

Val Pro Val Gln Val Pro Gly Ser Glu Pro Asp Met Ser Gln Tyr Trp
                420                 425                 430

Pro Arg Leu Gln
            435

<210> SEQ ID NO 115
<211> LENGTH: 6891
<212> TYPE: DNA
<213> ORGANISM: Homo sapiens

<400> SEQUENCE: 115
ggtgcatttg catgttgcgg agtgattagt gggtttgaaa agggaaccgt ggctcggcct      60
catttcccgc tctggttcag gcgcaggagg aagtgttttg ctggaggatg atgacagagg     120
aatctgagaa ttgctctcac acaccaaccc agcaacatcc gtggagaaaa ctctcaccag     180
caactccttt aaaacaccgt catttcaaac cattgtggtc ttcaagcaac aacagcagca     240
caaaaaaccc caaccaaaca aaactcttga cagaagctgt gacaaccaga aaggatgcct     300
cataaagggg gaagacttta actaggggcg cgcagatgtg tgaggccttt tattgtgaga     360
gtggacagac atccgagatt tcagagcccc atattcgagc cccgtggaat cccgcgccc      420 ccagccagag ccagcatgca gaacagtcac agcggagtga atcagctcgg tggtgtcttt     480
gtcaacgggc ggccactgcc ggactccacc cggcagaaga ttgtagagct agctcacagc     540
ggggcccggc cgtgcgacat tcccgaattc tgcagaccc atgcagatgc aaaagtccaa      600
gtgctggaca atcaaaacgt gtccaacgga tgtgtgagta aaattctggg caggtattac     660
gagactggct ccatcagacc cagggcaatc ggtggtagta accgagagt agcgactcca      720 gaagttgtaa gcaaaatagc ccagtataag cgggagtgcc cgtccatctt tgcttgggaa     780
atccgagaca gattactgtc cgaggggtc tgtaccaacg ataacatacc aagcgtgtca     840
```

```
tcaataaaca gagttcttcg caacctggct agcgaaaagc aacagatggg cgcagacggc    900
atgtatgata aactaaggat gttgaacggg cagaccggaa gctggggcac ccgccctggt    960
tggtatccgg ggacttcggt gccagggcaa cctacgcaag atggctgcca gcaacaggaa   1020
ggaggggag agaataccaa ctccatcagt tccaacggaa agattcaga tgaggctcaa     1080
atgcgacttc agctgaagcg gaagctgcaa agaaatagaa catcctttac caagagcaa    1140
attgaggccc tggagaaaga gtttgagaga acccattatc cagatgtgtt tgcccgagaa   1200
agactagcag ccaaaataga tctacctgaa gcaagaatac aggtatggtt ttctaatcga   1260
agggccaaat ggagaagaga agaaaaactg aggaatcaga gaagacaggc cagcaacaca   1320
cctagtcata ttcctatcag cagtagtttc agcaccagtg tctaccaacc aattccacaa   1380
cccaccacac cggtttcctc cttcacatct ggctccatgt tgggccgaac agacacagcc   1440
ctcacaaaca cctacagcgc tctgccgcct atgcccagct tcaccatggc aaataacctg   1500
cctatgcaac ccccagtccc cagccagacc tcctcatact cctgcatgct gcccaccagc   1560
ccttcggtga atgggcggag ttatgatacc tacaccccc cacatatgca gacacacatg    1620
aacagtcagc caatgggcac ctcgggcacc acttcaacag gactcatttc ccctggtgtg   1680
tcagttccag ttcaagttcc cggaagtgaa cctgatatgt ctcaatactg gccaagatta   1740
cagtaaaaaa aaaaaaaaa aaaaaaagga aggaaatat tgtgttaatt cagtcagtga    1800
ctatggggac acaacagttg agctttcagg aaagaaagaa aaatggctgt tagagccgct   1860
tcagttctac aattgtgtcc tgtattgtac cactggggaa ggaatggact tgaaacaagg   1920
acctttgtat acagaaggca cgatatcagt tggaacaaat cttcatttg gtatccaaac    1980
ttttattcat tttggtgtat tatttgtaaa tgggcatttg tatgttataa tgaaaaaaag   2040
aacaatgtag actggatgga tgtttgatct gtgttggtca tgaagttgtt ttttttttt    2100
ttaaaagaa aaccatgatc aacaagcttt gccacgaatt taagagtttt atcaagatat    2160
atcgaatact tctacccatc tgttcatagt ttatggactg atgttccaag tttgtatcat   2220
tcctttgcat ataattaaac ctggaacaac atgcactaga tttatgtcag aaatatctgt   2280
tggttttcca aaggttgtta acagatgaag tttatgtgca aaaagggta agatataaat     2340
tcaaggaaga aaaaagttg atagctaaaa ggtagagtgt gtcttcgata taatccaatt    2400
tgttttatgt caaaatgtaa gtatttgtct tccctagaaa tcctcagaat gatttctata   2460
ataaagttaa tttcatttat atttgacaag aatatagatg ttttatacac attttcatgc   2520
aatcatacgt ttctttttg gccagcaaaa gttaattgtt cttagatata gttgtattac    2580
tgttcacggt ccaatcattt tgtgcatcta gagttcattc ctaatcaatt aaaagtgctt   2640
gcaagagttt taaacttaag tgttttgaag ttgttcacaa ctacatatca aaattaacca   2700
ttgttgattg taaaaaacca tgccaaagcc tttgtatttc ctttattata cagttttctt   2760
tttaaccta tagtgtggtg ttacaaattt tatttccatg ttagatcaac attctaaacc   2820
aatggttact ttcacacaca ctctgtttta catcctgatg atccttaaaa aataatcctt   2880
atagatacca taaatcaaaa acgtgttaga aaaaaattcc acttacagca gggtgtagat   2940
ctgtgcccat ttatacccac aacatatata caaaatggta acatttccca gttagccatt   3000
taattctaaa gctcaaagtc tagaaataat ttaaaaatgc aacaagcgat tagctaggaa   3060
ttgttttttg aattaggact ggcattttca atctgggcag atttccattg tcagcctatt   3120
tcaacaatga tttcactgaa gtatattcaa aagtagattt cttaaaggag actttctgaa   3180
```

```
agctgttgcc ttttcaaat aggccctctc ccttttctgt ctccctcccc tttgcacaag    3240
aggcatcatt tcccattgaa ccactacagc tgttcccatt tgaatcttgc tttctgtgcg    3300
gttgtggatg gttggagggt ggaggggga tgttgcatgt caaggaataa tgagcacaga    3360
cacatcaaca gacaacaaca aagcagactg tgactggccg gtgggaatta aaggccttca    3420
gtcattggca gcttaagcca aacattccca aatctatgaa gcagggccca ttgttggtca    3480
gttgttattt gcaatgaagc acagttctga tcatgtttaa agtggaggca cgcagggcag    3540
gagtgcttga gcccaagcaa aggatggaaa aaataagcc tttgttgggt aaaaaaggac    3600
tgtctgagac tttcatttgt tctgtgcaac atataagtca atacagataa gtcttcctct    3660
gcaaacttca ctaaaaagcc tggggttct ggcagtctag attaaaatgc ttgcacatgc    3720
agaaacctct ggggacaaag acacacttcc actgaattat actctgcttt aaaaaaatcc    3780
ccaaaagcaa atgatcagaa atgtagaaat taatggaagg atttaaacat gaccttctcg    3840
ttcaatatct actgtttttt agttaaggaa ttacttgtga acagataatt gagattcatt    3900
gctccggcat gaaatatact aataatttta ttccaccaga gttgctgcac atttggagac    3960
accttcctaa gttgcagttt ttgtatgtgt gcatgtagtt ttgttcagtg tcagcctgca    4020
ctgcacagca gcacatttct gcaggggagt gagcacacat acgcactgtt ggtacaattg    4080
ccggtgcaga catttctacc tcctgacatt ttgcagccta cattccctga gggctgtgtg    4140
ctgagggaac tgtcagagaa gggctatgtg ggagtgcatg ccacagctgc tggctggctt    4200
acttcttcct tctcgctggc tgtaatttcc accacggtca ggcagccagt tccggcccac    4260
ggttctgttg tgtagacagc agagactttg gagacccgga tgtcgcacgc caggtgcaag    4320
aggtgggaat gggagaaaag gagtgacgtg ggagcggagg gtctgtatgt gtgcacttgg    4380
gcacgtatat gtgtgctctg aaggtcagga ttgccagggc aaagtagcac agtctggtat    4440
agtctgaaga agcggctgct cagctgcaga agccctctgg tccggcagga tgggaacggc    4500
tgccttgcct tctgcccaca ccctagggac atgagctgtc cttccaaaca gagctccagg    4560
cactctcttg gggacagcat ggcaggctct gtgtggtagc agtgcctggg agttggcctt    4620
ttactcattg ttgaaataat ttttgtttat tatttattta acgatacata tatttatata    4680
tttatcaatg gggtatctgc agggatgttt tgacaccatc ttccaggatg gagattattt    4740
gtgaagactt cagtagaatc ccaggactaa acgtctaaat tttttctcca aacttgactg    4800
acttgggaaa accaggtgaa tagaataaga gctgaatgtt ttaagtaata aacgttcaaa    4860
ctgctctaag taaaaaaatg cattttactg caatgaattt ctagaatatt tttcccccaa    4920
agctatgcct cctaaccctt aaatggtgaa caactggttt cttgctacag ctcactgcca    4980
tttcttctta ctatcatcac taggtttcct aagattcact catacagtat tatttgaaga    5040
ttcagctttg ttctgtgaat gtcatcttag gattgtgtct atattctttt gcttatttct    5100
ttttactctg ggcctctcat actagtaaga ttttaaaaag cctttcttc tctgtatgtt    5160 tggctcacca aggcgaaata tatattcttc tcttttcat ttctcaagaa taaacctcat    5220
ctgctttttt gttttctgt gtttggctt ggtactgaat gactcaactg ctcggtttta    5280
aagttcaaag tgtaagtact tagggttagt actgcttatt tcaataatgt tgacggtgac    5340
tatctttgga aagcagtaac atgctgtctt agaaatgaca ttaataatgg gcttaaacaa    5400
atgaataggg gggtccccc actctccttt tgtatgccta tgtgtgtctg atttgttaaa    5460
agatggacag ggaattgatt gcagagtgtc gcttccttct aaagtagttt tattttgtct    5520
actgttagta tttaaagatc ctggaggtgg acataaggaa taaatggaag agaaaagtag    5580
```

```
atattgtatg gtggctacta aaaggaaatt caaaaagtct tagaacccga gcacctgagc    5640
aaactgcagt agtcaaaata tttatctcat gttaaagaaa ggcaaatcta gtgtaagaaa    5700
tgagtaccat atagggtttt gaagttcata tactagaaac acttaaaaga tatcatttca    5760
gatattacgt ttggcattgt tcttaagtat ttatatcttt gagtcaagct gataattaaa    5820
aaaaatctgt taatggagtg tatatttcat aatgtatcaa aatggtgtct atacctaagg    5880
tagcattatt gaagagagat atgtttatgt agtaagttat taacataatg agtaacaaat    5940
aatgtttcca gaagaaagga aaacacattt tcagagtgcg ttttttatcag aggaagacaa    6000 aaatacacac ccctctccag tagcttattt ttacaaagcc ggcccagtga attagaaaaa    6060
caaagcactt ggatatgatt tttggaaagc ccaggtacac ttattattca aaatgcactt    6120
ttactgagtt tgaaaagttt cttttatatt taaaataagg gttcaaatat gcatattcaa    6180
tttttatagt agttatctat ttgcaaagca tatattaact agtaattggc tgttaattttt   6240 atagacatgg tagccaggga agtatatcaa tgacctatta agtattttga caagcaattt    6300
acatatctga tgacctcgta tctctttttc agcaagtcaa atgctatgta attgttccat    6360
tgtgtgttgt ataaaatgaa tcaacacggt aagaaaaagg ttagagttat taaaataata    6420
aactgactaa aatactcatt tgaatttatt cagaatgttc ataatgcttt caaaggacat    6480
agcagagctt tgtggagta tccgcacaac attatttatt atctatggac taaatcaatt    6540
ttttgaagtt gctttaaaat ttaaaagcac ctttgcttaa tataaagccc tttaatttta    6600
actgacagat caattctgaa actttatttt gaaagaaaa tggggaagaa tctgtgtctt    6660
tagaattaaa agaaatgaaa aaaataaacc cgacattcta aaaaaataga ataagaaacc    6720
tgatttttag tactaatgaa atagcgggtg acaaaatagt tgtcttttttg attttgatca    6780 caaaaaataa actggtagtg acaggatatg atggagagat ttgacatcct ggcaaatcac    6840
tgtcattgat tcaattattc taattctgaa taaaagctgt atacagtaaa a             6891
```

<210> SEQ ID NO 116
<211> LENGTH: 6883
<212> TYPE: DNA
<213> ORGANISM: Homo sapiens

<400> SEQUENCE: 116

```
accctctttt cttatcattg acatttaaac tctggggcag gtcctcgcgt agaacgcggc      60
tgtcagatct gccacttccc ctgccgagcg gcggtgagaa gtgtgggaac cggcgctgcc     120
aggctcacct gcctccccgc cctccgctcc caggaatctg agaattgctc tcacacacca     180
acccagcaac atccgtggag aaaactctca ccagcaactc ctttaaaaca ccgtcatttc     240
aaaccattgt ggtcttcaag caacaacagc agcacaaaaa accccaacca aacaaaactc     300
ttgacagaag ctgtgacaac cagaaaggat gcctcataaa gggggaagac tttaactagg     360
ggcgcgcaga tgtgtgaggc cttttattgt gagagtggac agacatccga gatttcagag    420
ccccatattc gagccccgtg gaatcccgcg gcccccagcc agagccagca tgcagaacag    480
tcacagcgga gtgaatcagc tcggtggtgt ctttgtcaac gggcggccac tgccggactc    540
cacccggcag aagattgtag agctagctca cagcggggcc cggccgtgcg acatttcccg    600
aattctgcag gtgtccaacg gatgtgtgag taaaattctg ggcaggtatt acgagactgg    660
ctccatcaga cccagggcaa tcggtggtag taaaccgaga gtagcgactc cagaagttgt    720
aagcaaaata gcccagtata agcgggagtg cccgtccatc tttgcttggg aaatccgaga    780
```

```
cagattactg tccgaggggg tctgtaccaa cgataacata ccaagcgtgt catcaataaa    840
cagagttctt cgcaacctgg ctagcgaaaa gcaacagatg ggcgcagacg gcatgtatga    900
taaactaagg atgttgaacg ggcagaccgg aagctggggc acccgccctg gttggtatcc    960
ggggacttcg gtgccagggc aacctacgca agatggctgc cagcaacagg aaggaggggg   1020
agagaatacc aactccatca gttccaacgg agaagattca gatgaggctc aaatgcgact   1080
tcagctgaag cggaagctgc aaagaaatag aacatccttt acccaagagc aaattgaggc   1140
cctggagaaa gagtttgaga gaacccatta tccagatgtg tttgcccgag aaagactagc   1200
agccaaaata gatctacctg aagcaagaat acaggtatgg ttttctaatc gaagggccaa   1260
atggagaaga gaagaaaaac tgaggaatca gagaagacag gccagcaaca cacctagtca   1320
tattcctatc agcagtagtt tcagcaccag tgtctaccaa ccaattccac aacccaccac   1380
accggtttcc tccttcacat ctggctccat gttgggccga acagacacag ccctcacaaa   1440
cacctacagc gctctgccgc ctatgccag cttcaccatg gcaaataacc tgcctatgca   1500
accccccagtc cccagccaga cctcctcata ctcctgcatg ctgcccacca gcccttcggt   1560
gaatgggcgg agttatgata cctacacccc cccacatatg cagacacaca tgaacagtca   1620
gccaatgggc acctcgggca ccacttcaac aggactcatt tcccctggtg tgtcagttcc   1680
agttcaagtt cccggaagtg aacctgatat gtctcaatac tggccaagat tacagtaaaa   1740
aaaaaaaaaa aaaaaaaaag gaaggaaat attgtgttaa ttcagtcagt gactatgggg   1800
acacaacagt tgagctttca ggaaagaaag aaaaatggct gttagagccg cttcagttct   1860
acaattgtgt cctgtattgt accactgggg aaggaatgga cttgaaacaa ggaccttttgt  1920
atacagaagg cacgatatca gttggaacaa atcttcattt tggtatccaa actttattc    1980
attttggtgt attatttgta aatgggcatt tgtatgttat aatgaaaaaa agaacaatgt   2040
agactggatg gatgtttgat ctgtgttggt catgaagttg ttttttttt ttttaaaaag    2100
aaaaccatga tcaacaagct ttgccacgaa tttaagagtt ttatcaagat atatcgaata   2160
cttctaccca tctgttcata gtttatggac tgatgttcca agtttgtatc attccttgc    2220
atataattaa acctggaaca acatgcacta gatttatgtc agaaatatct gttggttttc   2280
caaaggttgt taacagatga agtttatgtg caaaaaggg taagatataa attcaaggaa    2340
gaaaaaaagt tgatagctaa aaggtagagt gtgtcttcga tataatccaa tttgttttat   2400
gtcaaaatgt aagtatttgt cttccctaga atcctcaga atgatttcta taataaagtt    2460
aatttcatt tatatttgaca agaatataga tgttttatac acatttttcat gcaatcatac  2520
gtttctttt tggccagcaa aagttaattg ttcttagata tagttgtatt actgttcacg    2580
gtccaatcat tttgtgcatc tagagttcat tcctaatcaa ttaaaagtgc ttgcaagagt   2640
tttaaactta agtgttttga agttgttcac aactacatat caaaattaac cattgttgat   2700
tgtaaaaaac catgccaaag cctttgtatt tccttatta tacagttttc ttttaacct     2760
tatagtgtgg tgttacaaat tttatttcca tgttagatca acattctaaa ccaatggtta   2820
ctttcacaca cactctgttt tacatcctga tgatccttaa aaaataatcc ttatagatac   2880
cataaatcaa aaacgtgtta gaaaaaaatt ccacttacag cagggtgtag atctgtgccc   2940
atttataccc acaacatata tacaaaatgg taacatttcc cagttagcca tttaattcta   3000
aagctcaaag tctagaaata atttaaaaat gcaacaagcg attagctagg aattgttttt   3060
tgaattagga ctggcatttt caatctgggc agatttccat tgtcagccta tttcaacaat   3120
gatttcactg aagtatattc aaaagtagat ttcttaaagg agactttctg aaagctgttg   3180
```

```
ccttttcaa ataggccctc tcccttttct gtctccctcc cctttgcaca agaggcatca    3240
tttcccattg aaccactaca gctgttccca tttgaatctt gctttctgtg cggttgtgga    3300
tggttggagg gtggagggg gatgttgcat gtcaaggaat aatgagcaca gacacatcaa    3360
cagacaacaa caaagcagac tgtgactggc cggtgggaat taaaggcctt cagtcattgg    3420
cagcttaagc caaacattcc caaatctatg aagcagggcc cattgttggt cagttgttat    3480
ttgcaatgaa gcacagttct gatcatgttt aaagtggagg cacgcagggc aggagtgctt    3540
gagcccaagc aaaggatgga aaaaataag cctttgttgg gtaaaaaagg actgtctgag    3600
actttcattt gttctgtgca acatataagt caatacagat aagtcttcct ctgcaaactt    3660
cactaaaaag cctgggggtt ctggcagtct agattaaaat gcttgcacat gcagaaacct    3720
ctggggacaa agacacactt ccactgaatt atactctgct ttaaaaaaat ccccaaaagc    3780
aaatgatcag aaatgtagaa attaatggaa ggatttaaac atgaccttct cgttcaatat    3840
ctactgtttt ttagttaagg aattacttgt gaacagataa ttgagattca ttgctccggc    3900
atgaaatata ctaataattt tattccacca gagttgctgc acatttggag acaccttcct    3960
aagttgcagt ttttgtatgt gtgcatgtag ttttgttcag tgtcagcctg cactgcacag    4020
cagcacattt ctgcagggga gtgagcacac atacgcactg ttggtacaat tgccggtgca    4080
gacatttcta cctcctgaca ttttgcagcc tacattccct gagggctgtg tgctgaggga    4140
actgtcagag aagggctatg tgggagtgca tgccacagct gctggctggc ttacttcttc    4200
cttctcgctg gctgtaattt ccaccacggt caggcagcca gttccggccc acggttctgt    4260
tgtgtagaca gcagagactt tggagacccg gatgtcgcac gccaggtgca agaggtggga    4320
atgggagaaa aggagtgacg tgggagcgga gggtctgtat gtgtgcactt gggcacgtat    4380
atgtgtgctc tgaaggtcag gattgccagg gcaaagtagc acagtctggt atagtctgaa    4440
gaagcggctg ctcagctgca gaagccctct ggtccggcag gatgggaacg gctgccttgc    4500
cttctgccca caccctaggg acatgagctg tccttccaaa cagagctcca ggcactctct    4560
tggggacagc atggcaggct ctgtgtggta gcagtgcctg ggagttggcc ttttactcat    4620
tgttgaaata attttgttt attatttatt taacgataca tatatttata tatttatcaa    4680
tggggtatct gcaggatgt tttgacacca tcttccagga tggagattat ttgtgaagac    4740
ttcagtagaa tcccaggact aaacgtctaa attttttctc caaacttgac tgacttggga    4800
aaaccaggtg aatagaataa gagctgaatg ttttaagtaa taaacgttca aactgctcta    4860
agtaaaaaaa tgcattttac tgcaatgaat ttctagaata ttttttccccc aaagctatgc    4920 ctcctaaccc ttaaatggtg aacaactggt ttcttgctac agctcactgc catttcttct    4980
tactatcatc actaggtttc ctaagattca ctcatacagt attatttgaa gattcagctt    5040
tgttctgtga atgtcatctt aggattgtgt ctatattctt ttgcttattt cttttttactc    5100 tgggcctctc atactagtaa gattttaaaa agccttttct tctctgtatg tttggctcac    5160
caaggcgaaa tatatattct tctcttttc atttctcaag aataaacctc atctgctttt    5220 ttgttttct gtgttttggc ttggtactga atgactcaac tgctcggttt taaagttcaa    5280
agtgtaagta cttagggtta gtactgctta tttcaataat gttgacggtg actatctttg    5340
gaaagcagta acatgctgtc ttagaaatga cattaataat gggcttaaac aaatgaatag    5400
gggggtcccc ccactctcct tttgtatgcc tatgtgtgtc tgatttgtta aaagatggac    5460
agggaattga ttgcagagtg tcgcttcctt ctaaagtagt tttattttgt ctactgttag    5520
```

```
tatttaaaga tcctggaggt ggacataagg aataaatgga agagaaaagt agatattgta    5580
tggtggctac taaaaggaaa ttcaaaaagt cttagaaccc gagcacctga gcaaactgca    5640
gtagtcaaaa tatttatctc atgttaaaga aaggcaaatc tagtgtaaga aatgagtacc    5700
atatagggtt ttgaagttca tatactagaa acacttaaaa gatatcattt cagatattac    5760
gtttggcatt gttcttaagt atttatatct ttgagtcaag ctgataatta aaaaaaatct    5820
gttaatggag tgtatatttc ataatgtatc aaaatggtgt ctatacctaa ggtagcatta    5880
ttgaagagag atatgtttat gtagtaagtt attaacataa tgagtaacaa ataatgtttc    5940
cagaagaaag gaaaacacat tttcagagtg cgtttttatc agaggaagac aaaaatacac    6000 accccctctcc agtagcttat ttttacaaag ccggcccagt gaattagaaa aacaaagcac    6060
ttggatatga ttttttggaaa gcccaggtac acttattatt caaaatgcac ttttactgag    6120
tttgaaaagt ttcttttata tttaaaataa gggttcaaat atgcatattc aatttttata    6180
gtagttatct atttgcaaag catatattaa ctagtaattg gctgttaatt ttatagacat    6240
ggtagccagg gaagtatatc aatgacctat taagtatttt gacaagcaat ttacatatct    6300
gatgacctcg tatctctttt tcagcaagtc aaatgctatg taattgttcc attgtgtgtt    6360
gtataaaatg aatcaacacg gtaagaaaaa ggttagagtt attaaaataa taaactgact    6420
aaaatactca tttgaattta ttcagaatgt tcataatgct ttcaaaggac atagcagagc    6480
ttttgtggag tatccgcaca acattattta ttatctatgg actaaatcaa ttttttgaag    6540
ttgctttaaa atttaaaagc acctttgctt aatataaagc cctttaattt taactgacag    6600
atcaattctg aaactttatt ttgaaaagaa atggggaag aatctgtgtc tttagaatta    6660
aaagaaatga aaaaaataaa cccgacattc taaaaaaata gaataagaaa cctgattttt    6720
agtactaatg aaatagcggg tgacaaaata gttgtctttt tgattttgat cacaaaaaat    6780
aaactggtag tgacaggata tgatggagag atttgacatc ctggcaaatc actgtcattg    6840
attcaattat tctaattctg aataaaagct gtatacagta aaa                      6883
```

<210> SEQ ID NO 117
<211> LENGTH: 362
<212> TYPE: PRT
<213> ORGANISM: Homo sapiens

<400> SEQUENCE: 117

```
Met Gln Asn Ser His Ser Gly Val Asn Gln Leu Gly Gly Val Phe Val
 1               5                  10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Val
        35                  40                  45

Ser Asn Gly Cys Val Ser Lys Ile Leu Gly Arg Tyr Tyr Glu Thr Gly
    50                  55                  60

Ser Ile Arg Pro Arg Ala Ile Gly Gly Ser Lys Pro Arg Val Ala Thr
65                  70                  75                  80

Pro Glu Val Val Ser Lys Ile Ala Gln Tyr Lys Arg Glu Cys Pro Ser
                85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
```

```
        130                 135                 140
Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175

Cys Gln Gln Gln Glu Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Lys Leu Arg Asn Gln Arg Gln Ala Ser Asn Thr Pro Ser His
        210                 215                 220

Ile Pro Ile Ser Ser Ser Phe Ser Thr Ser Val Tyr Gln Pro Ile Pro
225                 230                 235                 240

Gln Pro Thr Thr Pro Val Ser Ser Phe Thr Ser Gly Ser Met Leu Gly
                245                 250                 255

Arg Thr Asp Thr Ala Leu Thr Asn Thr Tyr Ser Ala Leu Pro Pro Met
                260                 265                 270

Pro Ser Phe Thr Met Ala Asn Asn Leu Pro Met Gln Pro Pro Val Pro
            275                 280                 285

Ser Gln Thr Ser Ser Tyr Ser Cys Met Leu Pro Thr Ser Pro Ser Val
        290                 295                 300

Asn Gly Arg Ser Tyr Asp Thr Tyr Thr Pro Pro His Met Gln Thr His
305                 310                 315                 320

Met Asn Ser Gln Pro Met Gly Thr Ser Gly Thr Thr Ser Thr Gly Leu
                325                 330                 335

Ile Ser Pro Gly Val Ser Val Pro Val Gln Val Pro Gly Ser Glu Pro
            340                 345                 350

Asp Met Ser Gln Tyr Trp Pro Arg Leu Gln
        355                 360

<210> SEQ ID NO 118
<211> LENGTH: 1140
<212> TYPE: DNA
<213> ORGANISM: Homo sapiens

<400> SEQUENCE: 118
ccccatattc gagcccgtg gaatcccgcg gcccccagcc agagccagca tgcagaacag    60
tcacagcgga gtgaatcagc tcggtggtgt ctttgtcaac gggcggccac tgccggactc   120
cacccggcag aagattgtag agctagctca cagcggggcc cggccgtgcg acatttcccg   180
aattctgcag gtgtccaacg gatgtgtgag taaaattctg ggcaggtatt acgagactgg   240
ctccatcaga cccagggcaa tcggtggtag taaaccgaga gtagcgactc cagaagttgt   300
aagcaaaata gcccagtata gcgggagtg cccgtccatc tttgcttggg aaatccgaga   360
cagattactg tccgagggg tctgtaccaa cgataacata ccaagcgtgt catcaataaa   420
cagagttctt cgcaacctgg ctagcgaaaa gcaacagatg ggcgcagacg gcatgtatga   480
taaactaagg atgttgaacg ggcagaccgg aagctgggc acccgccctg ttggtatcc   540 ggggacttcg gtgccaggc aacctacgca agatggctgc cagcaacagg aaggagggg   600 agagaatacc aactccatca gttccaacgg agaagattca gatgaggctc aaatgcgact   660
tcagctgaag cggaagaaac tgaggaatca gagaagacag gccagcaaca cacctagtca   720
tattcctatc agcagtagtt tcagcaccag tgtctaccaa ccaattccac aacccaccac   780
accggtttcc tccttcacat ctggctccat gttgggccga acagacacag ccctcacaaa   840
```

-continued

```
cacctacagc gctctgccgc ctatgcccag cttcaccatg gcaaataacc tgcctatgca      900
accccccagtc cccagccaga cctcctcata tcctgcatg ctgcccacca gcccttcggt      960
gaatgggcgg agttatgata cctacacccc ccacatatg cagacacaca tgaacagtca     1020
gccaatgggc acctcgggca ccacttcaac aggactcatt tccctggtg tgtcagttcc     1080
agttcaagtt cccggaagtg aacctgatat gtctcaatac tggccaagat tacagtaaaa     1140
```

<210> SEQ ID NO 119
<211> LENGTH: 347
<212> TYPE: PRT
<213> ORGANISM: Homo sapiens

<400> SEQUENCE: 119

```
Met Arg Val Ala Thr Pro Glu Val Val Ser Lys Ile Ala Gln Tyr Lys
1               5                   10                  15

Arg Glu Cys Pro Ser Ile Phe Ala Trp Glu Ile Arg Asp Arg Leu Leu
            20                  25                  30

Ser Glu Gly Val Cys Thr Asn Asp Asn Ile Pro Ser Val Ser Ser Ile
        35                  40                  45

Asn Arg Val Leu Arg Asn Leu Ala Ser Glu Lys Gln Gln Met Gly Ala
    50                  55                  60

Asp Gly Met Tyr Asp Lys Leu Arg Met Leu Asn Gly Gln Thr Gly Ser
65                  70                  75                  80

Trp Gly Thr Arg Pro Gly Trp Tyr Pro Gly Thr Ser Val Pro Gly Gln
                85                  90                  95

Pro Thr Gln Asp Gly Cys Gln Gln Glu Gly Gly Glu Asn Thr
            100                 105                 110

Asn Ser Ile Ser Ser Asn Gly Glu Asp Ser Asp Glu Ala Gln Met Arg
        115                 120                 125

Leu Gln Leu Lys Arg Lys Leu Gln Arg Asn Arg Thr Ser Phe Thr Gln
    130                 135                 140

Glu Gln Ile Glu Ala Leu Glu Lys Glu Phe Glu Arg Thr His Tyr Pro
145                 150                 155                 160

Asp Val Phe Ala Arg Glu Arg Leu Ala Ala Lys Ile Asp Leu Pro Glu
                165                 170                 175

Ala Arg Ile Gln Val Trp Phe Ser Asn Arg Arg Ala Lys Trp Arg Arg
            180                 185                 190

Glu Glu Lys Leu Arg Asn Gln Arg Gln Ala Ser Asn Thr Pro Ser
        195                 200                 205

His Ile Pro Ile Ser Ser Ser Phe Ser Thr Ser Val Tyr Gln Pro Ile
    210                 215                 220

Pro Gln Pro Thr Thr Pro Val Ser Ser Phe Thr Ser Gly Ser Met Leu
225                 230                 235                 240

Gly Arg Thr Asp Thr Ala Leu Thr Asn Thr Tyr Ser Ala Leu Pro Pro
                245                 250                 255

Met Pro Ser Phe Thr Met Ala Asn Asn Leu Pro Met Gln Pro Pro Val
            260                 265                 270

Pro Ser Gln Thr Ser Ser Tyr Ser Cys Met Leu Pro Thr Ser Pro Ser
        275                 280                 285

Val Asn Gly Arg Ser Tyr Asp Thr Tyr Thr Pro Pro His Met Gln Thr
    290                 295                 300

His Met Asn Ser Gln Pro Met Gly Thr Ser Gly Thr Thr Ser Thr Gly
305                 310                 315                 320
```

Leu Ile Ser Pro Gly Val Ser Val Pro Val Gln Val Pro Gly Ser Glu
              325                 330                 335

Pro Asp Met Ser Gln Tyr Trp Pro Arg Leu Gln
          340                 345

<210> SEQ ID NO 120
<211> LENGTH: 1095
<212> TYPE: DNA
<213> ORGANISM: Homo sapiens

<400> SEQUENCE: 120
ccccatattc gagccccgtg gaatcccgcg gccccccagcc agagccagca tgagagtagc        60
gactccagaa gttgtaagca aaatagccca gtataagcgg gagtgcccgt ccatctttgc       120
ttgggaaatc cgagacagat tactgtccga gggggtctgt accaacgata acataccaag       180
cgtgtcatca ataaacagag ttcttcgcaa cctggctagc gaaaagcaac agatgggcgc       240
agacggcatg tatgataaac taaggatgtt gaacgggcag accggaagct ggggcacccg       300
ccctggttgg tatccgggga cttcggtgcc agggcaacct acgcaagatg gctgccagca       360
acaggaagga gggggagaga ataccaactc catcagttcc aacggagaag attcagatga       420
ggctcaaatg cgacttcagc tgaagcggaa gctgcaaaga aatagaacat cctttaccca       480
agagcaaatt gaggccctgg agaaagagtt tgagagaacc cattatccag atgtgtttgc       540
ccgagaaaga ctagcagcca aaatagatct acctgaagca gaatacagg tatggttttc       600 taatcgaagg gccaaatgga agagaagaa aaactgagg atcagagaa acaggccag         660 caacacacct agtcatattc ctatcagcag tagtttcagc accagtgtct accaaccaat       720
tccacaaccc accacaccgg tttcctcctt cacatctggc tccatgttgg gccgaacaga       780
cacagccctc acaaacacct acagcgctct gccgcctatg cccagcttca ccatggcaaa       840
taacctgcct atgcaaccc cagtccccag ccagacctcc tcatactcct gcatgctgcc       900
caccagcccc tcggtgaatg ggcggagtta tgatacctac accccccac atatgcagac       960 acacatgaac agtcagccaa tgggcacctc gggcaccact tcaacaggac tcatttcccc      1020
tggtgtgtca gttccagttc aagttcccgg aagtgaacct gatatgtctc aatactggcc      1080
aagattacag taaaa                                                       1095

<210> SEQ ID NO 121
<211> LENGTH: 221
<212> TYPE: PRT
<213> ORGANISM: Homo sapiens

<400> SEQUENCE: 121

Met Arg Leu Gln Leu Lys Arg Lys Leu Gln Arg Asn Arg Thr Ser Phe
1               5                   10                  15

Thr Gln Glu Gln Ile Glu Ala Leu Glu Lys Glu Phe Glu Arg Thr His
            20                  25                  30

Tyr Pro Asp Val Phe Ala Arg Glu Arg Leu Ala Ala Lys Ile Asp Leu
        35                  40                  45

Pro Glu Ala Arg Ile Gln Val Trp Phe Ser Asn Arg Arg Ala Lys Trp
    50                  55                  60

Arg Arg Glu Glu Lys Leu Arg Asn Gln Arg Arg Gln Ala Ser Asn Thr
65                  70                  75                  80

Pro Ser His Ile Pro Ile Ser Ser Ser Phe Ser Thr Ser Val Tyr Gln
                85                  90                  95

Pro Ile Pro Gln Pro Thr Thr Pro Val Ser Ser Phe Thr Ser Gly Ser

```
            100                 105                 110
Met Leu Gly Arg Thr Asp Thr Ala Leu Thr Asn Thr Tyr Ser Ala Leu
            115                 120                 125

Pro Pro Met Pro Ser Phe Thr Met Ala Asn Asn Leu Pro Met Gln Pro
        130                 135                 140

Pro Val Pro Ser Gln Thr Ser Ser Tyr Ser Cys Met Leu Pro Thr Ser
145                 150                 155                 160

Pro Ser Val Asn Gly Arg Ser Tyr Asp Thr Tyr Thr Pro Pro His Met
                165                 170                 175

Gln Thr His Met Asn Ser Gln Pro Met Gly Thr Ser Gly Thr Thr Ser
            180                 185                 190

Thr Gly Leu Ile Ser Pro Gly Val Ser Val Pro Val Gln Val Pro Gly
        195                 200                 205

Ser Glu Pro Asp Met Ser Gln Tyr Trp Pro Arg Leu Gln
    210                 215                 220

<210> SEQ ID NO 122
<211> LENGTH: 717
<212> TYPE: DNA
<213> ORGANISM: Homo sapiens

<400> SEQUENCE: 122 cccatattc gagccccgtg aatcccgcg gccccagcc agagccagca tgcgacttca      60
gctgaagcgg aagctgcaaa gaaatagaac atcctttacc aagagcaaa ttgaggccct    120 ggagaaagag tttgagagaa cccattatcc agatgtgttt gcccgagaaa gactagcagc    180
caaaatagat ctacctgaag caagaataca ggtatggttt tctaatcgaa gggccaaatg    240
gagaagagaa gaaaaactga ggaatcgag aagacaggcc agcaacacac ctagtcatat    300
tcctatcagc agtagtttca gcaccagtgt ctaccaacca attccacaac ccaccacacc    360
ggtttcctcc ttcacatctg gctccatgtt gggccgaaca gacacagccc tcacaaacac    420
ctacagcgct ctgccgccta tgcccagctt caccatggca ataacctgc ctatgcaacc    480 cccagtcccc agccagacct cctcatactc ctgcatgctg cccaccagcc cttcggtgaa    540
tgggcggagt tatgataccct acacccccc acatatgcag acacacatga acagtcagcc    600
aatgggcacc tcgggcacca cttcaacagg actcattttcc cctggtgtgt cagttccagt    660
tcaagttccc ggaagtgaac ctgatatgtc tcaatactgg ccaagattac agtaaaa      717

<210> SEQ ID NO 123
<211> LENGTH: 358
<212> TYPE: PRT
<213> ORGANISM: Homo sapiens

<400> SEQUENCE: 123

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45

His Ala Asp Ala Lys Val Gln Val Leu Asp Asn Gln Asn Val Ser Asn
    50                  55                  60

Gly Cys Val Ser Lys Ile Leu Gly Arg Tyr Tyr Glu Thr Gly Ser Ile
65                  70                  75                  80

Arg Pro Arg Ala Ile Gly Gly Ser Lys Pro Arg Val Ala Thr Pro Glu
```

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |

Val Val Ser Lys Ile Ala Gln Tyr Lys Arg Glu Cys Pro Ser Ile Phe
            100                 105                 110

Ala Trp Glu Ile Arg Asp Arg Leu Leu Ser Glu Gly Val Cys Thr Asn
            115                 120                 125

Asp Asn Ile Pro Ser Val Ser Ser Ile Asn Arg Val Leu Arg Asn Leu
            130                 135                 140

Ala Ser Glu Lys Gln Gln Met Gly Ala Asp Gly Met Tyr Asp Lys Leu
145                 150                 155                 160

Arg Met Leu Asn Gly Gln Thr Gly Ser Trp Gly Thr Arg Pro Gly Trp
                165                 170                 175

Tyr Pro Gly Thr Ser Val Pro Gly Gln Pro Thr Gln Asp Gly Cys Gln
                180                 185                 190

Gln Gln Glu Gly Gly Gly Glu Asn Thr Asn Ser Ile Ser Ser Asn Gly
                195                 200                 205

Glu Asp Ser Asp Glu Ala Gln Met Arg Leu Gln Leu Lys Arg Lys Leu
            210                 215                 220

Gln Arg Asn Arg Thr Ser Phe Thr Gln Glu Gln Ile Glu Ala Leu Glu
225                 230                 235                 240

Lys Glu Phe Glu Arg Thr His Tyr Pro Asp Val Phe Ala Arg Glu Arg
                245                 250                 255

Leu Ala Ala Lys Ile Asp Leu Pro Glu Ala Arg Ile Gln Val Trp Phe
            260                 265                 270

Ser Asn Arg Arg Ala Lys Trp Arg Arg Glu Glu Lys Leu Arg Asn Gln
            275                 280                 285

Arg Arg Gln Ala Ser Asn Thr Pro Ser His Ile Pro Ile Ser Ser Ser
    290                 295                 300

Phe Ser Thr Ser Val Tyr Gln Pro Ile Pro Gln Pro Thr Thr Pro Val
305                 310                 315                 320

Ser Ser Phe Thr Ser Gly Ser Met Leu Gly Arg Thr Asp Thr Ala Leu
                325                 330                 335

Thr Asn Thr Tyr Ser Ala Leu Pro Pro Met Pro Ser Phe Thr Met Ala
            340                 345                 350

Asn Asn Leu Pro Met Gln
            355

```
<210> SEQ ID NO 124
<211> LENGTH: 1096
<212> TYPE: DNA
<213> ORGANISM: Homo sapiens

<400> SEQUENCE: 124
```

| | | |
|---|---|---|
| ccagccagag ccagcatgca gaacagtcac agcggagtga atcagctcgg tggtgtcttt | 60 |
| gtcaacgggc ggccactgcc ggactccacc cggcagaaga ttgtagagct agctcacagc | 120 |
| ggggcccggc cgtgcgacat ttcccgaatt ctgcagaccc atgcagatgc aaaagtccaa | 180 |
| gtgctggaca atcaaaacgt gtccaacgga tgtgtgagta aaattctggg caggtattac | 240 |
| gagactggct ccatcagacc cagggcaatc ggtggtagta aaccgagagt agcgactcca | 300 |
| gaagttgtaa gcaaaatagc ccagtataag cgggagtgcc cgtccatctt tgcttgggaa | 360 |
| atccgagaca gattactgtc gagggggtc tgtaccaacg ataacatacc aagcgtgtca | 420 |
| tcaataaaca gagttcttcg caacctggct agcgaaaagc aacagatggg cgcagacggc | 480 |
| atgtatgata aactaaggat gttgaacggg cagaccggaa gctggggcac ccgccctggt | 540 |

```
tggtatccgg ggacttcggt gccagggcaa cctacgcaag atggctgcca gcaacaggaa      600 ggaggggag agaataccaa ctccatcagt tccaacggag aagattcaga tgaggctcaa       660
atgcgacttc agctgaagcg gaagctgcaa agaaatagaa catcctttac ccaagagcaa     720
attgaggccc tggagaaaga gtttgagaga acccattatc cagatgtgtt tgcccgagaa     780
agactagcag ccaaaataga tctacctgaa gcaagaatac aggtatggtt ttctaatcga     840
agggccaaat ggagaagaga agaaaaactg aggaatcaga gaagacaggc cagcaacaca     900
cctagtcata ttcctatcag cagtagtttc agcaccagtg tctaccaacc aattccacaa     960
cccaccacac cggtttcctc cttcacatct ggctccatgt tgggccgaac agacacagcc    1020
ctcacaaaca cctacagcgc tctgccgcct atgcccagct tcaccatggc aaataacctg    1080
cctatgcaat aaaaaa                                                    1096
```